US008507657B2

(12) United States Patent
Nicolaides et al.

(10) Patent No.: US 8,507,657 B2
(45) Date of Patent: Aug. 13, 2013

(54) ANTI-GD2 ANTIBODIES

(75) Inventors: Nicholas C. Nicolaides, Garnett Valley, PA (US); Philip M. Sass, Audubon, PA (US); Luigi Grasso, Bryn Mawr, PA (US); Wolfgang Ebel, Plymouth Meeting, PA (US); Yuhong Zhou, Phoenixville, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 13/593,057

(22) Filed: Aug. 23, 2012

(65) Prior Publication Data

US 2012/0328524 A1 Dec. 27, 2012

Related U.S. Application Data

(62) Division of application No. 12/494,631, filed on Jun. 30, 2009, now Pat. No. 8,278,065.

(60) Provisional application No. 61/077,041, filed on Jun. 30, 2008, provisional application No. 61/097,034, filed on Sep. 15, 2008.

(51) Int. Cl.
*C07K 16/00* (2006.01)
*C12P 21/08* (2006.01)

(52) U.S. Cl.
USPC ............... 530/388.1; 530/387.1; 530/388.15

(58) Field of Classification Search
None
See application file for complete search history.

(56) References Cited

U.S. PATENT DOCUMENTS

| | | | |
|---|---|---|---|
| 5,419,904 | A | 5/1995 | Irie |
| 6,309,636 | B1 | 10/2001 | do Couto et al. |
| 6,777,540 | B1 | 8/2004 | Okumura et al. |

FOREIGN PATENT DOCUMENTS

| | | |
|---|---|---|
| EP | 1652925 | 5/2006 |
| WO | WO 93/10221 | 5/1993 |
| WO | WO 94/19457 | 9/1994 |
| WO | WO 97/34634 | 9/1997 |
| WO | WO 2004/055056 | 7/2004 |
| WO | WO 2008/043777 | 4/2008 |
| WO | WO 2010/002822 | 1/2010 |

OTHER PUBLICATIONS

Bolesta et al. DNA vaccine expressing the mimotope of GD2 ganglioside induces protective GD2 cross-reactive antibody responses. Cancer Res. Apr. 15, 2005;65(8): 3410-8.*
Birklé et al. Role of tumor-associated gangliosides in cancer progression. Biochimie. Mar.-Apr. 2003;85(3-4):455-63.*
"FY2009 Product Creation Meeting, Dramatic Leap Plan 2011", Eisai Co., Ltd., Power Point Presentation, 121 pages, Dec. 18, 2009.
Alvarez-Rueda et al., "Binding Activities and Antitumor Properties of a New Mouse/Human Chimeric Antibody Specific for GD2 Ganglioside Antigen", Clinical Cancer Research, Sep. 15, 2007, 13(18), Part 2, 5613s-5620s.
Azuma et al., "Recombinant Human Hexamer-domain IgM Monoclonal Antibody to Ganglioside GM3 for Treatment of Melanoma", Clin. Cancer Res., May 1, 2007, 13(9), 2745-2750.
Cahan et al., "Identification of a Human Neuroectodermal Tumor Antigen (OFA-I-2) as Ganglioside GD2", Proc. Natl. Acad. Sci. USA, Dec. 1982, 79(24), 7629-7633.
Cerato et al., "Variable Region Gene Segments of Nine Monoclonal Antibodies Specific to Disialogangliosides (GD2, DG3) and Their O-Acetylated Derivatives" Hybridoma, Aug. 1, 1997, 16(4), 307-316.
Cheresh et al., "Localization of the Gangliosides GD2 and GD3 in Adhesion Plaques and on the Surface of human melanoma cells", PNAS USA, Sep. 1984, 81, 5767-57771.
Chothia et al., "Canonical Structures for the Hypervariable Regions of Immunoglobulins" J. Mol. Biol., Aug. 20, 1987, 196(4), 901-917.
Cline, "Perspectives for Gene Therapy: Inserting New Genetic Information into Mammalian Cells by Physical Techniques and Viral Vectors", Pharmac. Ther., 1985, 29(1), 69-92.
Foote et al., "Antibody Framework Residues Affecting the Conformation of the Hypervariable Loops", J. Mol. Biol., Mar. 20, 1992, 224(2), 487-499.
Friedrichs et al., "Glycoprotein gp118 of Varicella-Zoster Virus: Purification by Serial Affinity Chromatography", J. Virol., Mar. 1984, 49(3), 992-996.
Gadi et al., "In Vivo Sensitization of Ovarian Tumors to Chemotherapy by Expression of *E. coli* Purine Nucleoside Phosphorylase in a Small Fraction of Cells", Gene Ther., Oct. 2000, 7(20), 1738-1743.
Garmestani et al., "Synthesis and Evaluation of a Macrocyclic Bifunctional Chelating Agent for Use with Bismuth Radionuclides", Nucl. Med. Biol., May 2001, 28(4), 409-418.
Hakomori, "Glycosylation Defining Cancer Malignancy: New Wine in an Old Bottle", Proc. Natl. Acad. Sci., Aug. 6, 2002, 99(16), 10231-10233.
Hoogenboom, "Selecting and Screening Recombinant Antibody Libraries", Nature Biotechnology, Sep. 1, 2005, 23(9), 1105-1116.
Hoon et al., "Molecular Cloning of a Human Monoclonal Antibody Reactive to Ganglioside Gm3 Antigen on Human Cancers", Cancer Research, Nov. 1, 1993, 5244-5250.
Imai et al., "Complement-Mediated Mechanisms in Anti-GD2 Monoclonal Antibody Therapy of Murine Metastatic Cancer", Cancer Research, Nov. 2005, 65(22), 10562-10568.
Irie et al., "Human Antibody to OFA-I a tumor antigen, produced in vitro by Epstein-Barr virus-transformed human B-lymphoid cell lines", Proc. Natl. Acad. Sci USA, Sep. 1982, 79, 5666-5670.
Irie et al., "In Vitro Production of Human Antibody to a Tumour-Associated Foetal Antigen", Br. J. Cancer, Apr. 13, 1981, 44, 262-266.

(Continued)

*Primary Examiner* — Dong Jiang
(74) *Attorney, Agent, or Firm* — Woodcock Washburn, LLP

(57) ABSTRACT

Described herein are antibodies that specifically bind ganglioside GD2. Also described are nucleotides encoding such antibodies, cells expressing such antibodies, methods of use for such antibodies, and methods for using the antibodies to treat diseases associated with ganglioside GD2. In addition, tissue culture media supplements are described as are methods of use for the supplements. Described herein are albumin-ganglioside conjugates and corresponding methods for producing such conjugates. Methods of purifying or isolating antibodies are also described.

6 Claims, 28 Drawing Sheets

(56) References Cited

OTHER PUBLICATIONS

Irie et al., "Phase I Pilot Clinical Trial of Human IgM Monoclonal Antibody to Ganglioside GM3 in Patients with Metastatic Melanoma", Cancer Immunol. Immunother., Feb. 2004, 53(2), 110-117.
Irie et al., "Regression of Cutaneous Metastatic Melanoma by Intralesional Injection with Human Monoclonal Antibody to Ganglioside GD2", Proceedings of the National Academy of Sciences of USA, National Academy of Sciences of USA, Nov. 1, 1986, 83(22), 8694-8698.
Jacques et al., "Chemoenzymatic Synthesis of GM3 and GM2 Gangliosides Containing a Truncated Ceramide Functionalized for Glycoconjugate Synthesis and Solid Phase Applications", Org. Biomol. Chem., Jan. 7, 2006, 4(1), 142-154.
Janeway et al., Immunobiology, Garland Science, Fifth Edition, Jun. 21, 2001, Sections 9-12, pp. 1-2.
Jirholt et al., "Exploiting Sequence Space: Shuffling in Vivo Formed Complementarity Determining Regions Into a Master Framework", Gene Jul. 30, 1998, 215(2), 471-476.
Jones et al., "Prolonged Survival for Melanoma Patients with Elevated IgM Antibody to Oncofetal Antigen", J. Natl. Cancer Inst., Feb. 1981, 66(2), 249-254.
Jones et al., "Replacing the Complementarity-Determining Regions in a Human Antibody With Those From a Mouse", Nature, May 29-Jun. 4, 1986, 321, 522-525.
Kala et al., "Phage Displayed Antibodies to Heat Stable Alkaline Phosphatase: Framework Region as a Determinant of Specificity", J. Biochem., Oct. 2002, 132(4), 535-541.
Karlin et al., "Applications and Statistics for Multiple High-Scoring Segments in Molecular Sequences", Proc. Natl. Acad. Sci. USA, Jun. 15, 1993, 90(12), 5873-5877.
Karlin et al., "Methods for Assessing the Statistical Significance of Molecular Sequence Features by Using General Scoring Schemes", Proc. Natl. Acad. Sci. USA, Mar. 1990, 87(6), 2264-2268.
Katano et al., "Human monoclonal antibody to tumor-associated ganglioside GD2", J. Clin. Lab. Immunol., Nov. 1984, 15(3), 119-126.
Katano et al., "Human monoclonal antibody to tumor-associated ganglioside GD2: suppressed growth of human melanoma in nude mice", Immunol. Lett., 1984, 8(4), 169-174.
Katano et al., "Human Monoclonal Antibody to a Neuroectodermal Tumor Antigen (OFA-I-2)", Annals of the New York Academy of Sciences, 1983, 417, 427-434.
Kishiro et al., "Butyrate Enhances the in Vitro Anti-SRBC (Sheep Red Blood Cell) Antibody Responses in Murine Splenocytes", Jpn. J. Pharmacol., Aug. 24, 1994, 66, 369-376.
MacCallum et al., "Antibody-antigen Interactions: Contact Analysis and Binding Site Topography," J. Mol. Biol., Oct. 1996, 262(5), 732-745.
Morea et al., "Conformations of the Third Hypervariable Region in the VH Domain of Immunoglobulins", J. Mol. Biol., Jan. 16, 1998, 275(2), 269-294.
Mujoo et al., "Disialoganglioside GD2 on Human Neuroblastoma Cells: Target Antigen for Monoclonal Antibody-Mediated Cytolysis and Suppression of Tumor Growth", American Association for Cancer Research, Feb. 15, 1987, 47(4), 1098-1104.
Nicaise et al., "Affinity Transfer by CDR Grafting on a Nonimmunoglobulin Scaffold", Protein Sci., Jul. 2004, 13(7), 1882-1891.
Niles et al., "Polymer IgM assembly and secretion in Lymphoid and Nonlymphoid Cell Lines: Evidence That J Chain is required for Pentamer IgM Synthesis", Proc. Natl. Acad. Sci USA, Mar. 1995, 92, 2884-2888.
Okayama et al., "A cDNA Cloning Vector That Permits Expression of cDNA Inserts in Mammalian Cells", Mol. Cell. Biol., Feb. 1983, 3(2), 280-289.
Padlan et al., "Structure of an antibody-antigen complex: crystal structure of the HyHEL-10 Fab-lysozyme complex," Proc. Natl. Acad. Sci. USA, Aug. 1989, 86(15), 5938-5942.
Panka et al., "Variable Region Framework Differences Result in Decreased or Increased Affinity of Variant Anti-Digoxin Antibodies", Proc. Natl. Acad. Sci. USA, May 1988, 85(9), 3080-3084.
Presta, L., "Antibody Engineering", Curr. Op. Struct. Biol., Aug. 1992, 2(4), 593-596.
Randall et al., "J Chain Synthesis and Secretion of Hexameric IgM is differentially regulated by Lipopolysaccharide and Interleukin 5", PNAS USA, Feb. 1992, 89, 962-966.
Raqupathi et al., "Consistent Antibody Response Against Ganglioside GD2 Induced in Patients with Melanoma by a GD2 Lactone-Keyhold Limpet Hemocyanin Conjugate Vaccine Plus Immunological Adjuvant QS-21", Clinical Cancer Research, Nov. 1, 2003, 9, 5214-5220.
Reichmann et al., "Reshaping human antibodies for therapy", Nature, Mar. 24, 1988, 332, 323-329.
Söderlind et al., "Recombining Germline-Derived CDR Sequences for Creating Diverse Single-Framework Antibody Libraries", Nature Biotechnology, Aug. 2000, 18(8), 852-856.
Tai et al., "Immunogencity of Melanoma-Associated Gangliosides in Cancer Patients", Int. J. Cancer, May 15, 1985, 35(5), 607-612.
Takahashi et al., "IgM Anti-Ganglioside Antibodies Induced by Melanoma Cell Vaccine Correlate with Survival of Melanoma Patients", Journal of Investigative Dermatology, Feb. 1999, 112(2), 205-209.
Tiemeyer et al., "Ganglioside-Specific Binding Protein on Rat Brain Membranes", J. of Biological Chemistry, Jan. 25, 1989, 264(3), 1671-1681.
Wiersma et al., "Structural and Functional Analysis of J Chain-Deficient IgM", J. Immunol., Feb. 19, 1998, 160, 5979-5989.
Yoshimatsu, K., "Oncology Research & Development", Eisai Co. Ltd., Dramatic Leap Plan 2011, Sep. 16, 2008, 36 pages, p. 27 http://www.eisai.co.jp/pdf/eir/emat/material20080916e.pdf.

* cited by examiner

A

M14
 MG1055

RPMI7951 
 JS0592

B

M14
MG1055

RPMI7951
JS0592

ANTI-GD2 ANTIBODIES

CROSS-REFERENCE TO RELATED APPLICATIONS

This application is a divisional application of U.S. patent application Ser. No. 12/494,631, filed Jun. 30, 2009, which claims the benefit of U.S. Provisional Application No. 61/077,041, filed Jun. 30, 2008, and of U.S. Provisional Application No. 61/097,034, filed Sep. 15, 2008, all of which are incorporated by reference herein.

TECHNICAL FIELD

The invention generally relates to the field of immunotherapeutic agents. More specifically, the invention relates to monoclonal antibodies that bind gangliosides and methods for using such antibodies to treat subjects in need of such treatment. Also provided are methods for using the described antibodies for diagnostic and therapeutic purposes. In addition, tissue culture media compositions and methods that relate to culturing cells expressing the described antibodies, as well as methods for purifying or isolating the described antibodies are also provided.

BACKGROUND

Cancer is the second leading cause of death in the United States. The National Cancer Institute (NCI) of the U.S. National Institutes of Health (NIH) estimates that over 500,000 individuals will die from cancer and over 1.4 million individuals will be diagnosed with cancer in 2008. There is a global research effort to develop methods of treatment for cancer and to enhance the general understanding of how to prevent cancer, with countries like the United Kingdom, the Unites States, and others making cancer-related research a top priority. For example, the NIH has earmarked over 5 billion dollars in funding for cancer-related research for the 2008 fiscal year, almost twice the amount of funding provided for other serious diseases, such as HIV and heart disease.

There are over 100 different types of cancer. Despite the wide variety of cancers, most cancer-related deaths are caused by a few common cancers, such as lung cancer, colorectal cancer, and breast cancer. The NCI estimates that these three forms of cancer will cause over 250,000 deaths in 2008. While not as deadly as those cancers mentioned previously, skin cancer represents about half of all newly diagnosed cancers in the U.S., making it the most common type of cancer. Of the various types of skin cancer, melanoma is the rarest and most deadly. The American Cancer Society estimates that while melanoma accounts for only 4% of all diagnosed skin cancers in the U.S., it causes 79% of all skin cancer-related deaths.

Successful cancer treatment is often attributed to early diagnosis and treatment. A powerful method of diagnosing cancer is detecting tumor markers known to be associated with cancer. Tumor markers are substances, often proteins, which are produced by tumor cells, or other cells in the body in response to cancer. Tumor markers can be found in the blood, urine, on the surface of tumor cells, or on (or in) other, non-cancerous cells and tissues. Gangliosides have been identified as one type of marker associated with many tumors (Hakomori, 99 Proc. Natl. Acad. Sci. U.S.A. 10718 (2002)).

Gangliosides are glycosphingolipids with at least one sugar-linked sialic acid. These compounds are components of cell plasma membranes and are thought to play a central role in a variety of biological functions, such as cell growth, cell differentiation, cell signaling, and serving as receptors for microbial toxins (Jacques, et al. 4 Org. Biomol. Chem. 142 (2006)). Over 40 different gangliosides have been identified; however, a certain subset of these, GM3, GM2, GD3, and GD2, are commonly over-expressed by tumor cells (Id). Furthermore, gangliosides are reported to be highly immunogenic in humans. The combination of high immunogenicity and over-expression by tumor cells makes gangliosides a potential target for cancer therapeutics.

Ganglioside-specific monoclonal antibodies have been developed and, in some cases, examined for efficacy in humans (See generally, Azuma et al., 13 Clin. Cancer Res. 2745 (2007); Irie, et al., 53 Cancer Immunol. Immunother. 110 (2004); Irie and Morton, 83 Proc. Natl. Acad. Sci. U.S.A. 8694 (1986)). One of the earliest reports concerning a human, GD2-specific antibody was by Cahan, et al. (79 Proc. Natl. Acad. Sci. U.S.A. 7629 (1982)) Immunotherapy studies have shown that higher survival rates correlate with ganglioside-specific IgM, rather than IgG, for patients vaccinated with a melanoma vaccine (Jones et al., 66 J. Natl. Cancer Inst. 249 (1981)). Consistent with this finding, human studies involving IgM antibodies to gangliosides GD2 and GD3 have provided encouraging results for the use of such antibodies as a possible treatment for melanoma (Irie, et al., 53 Cancer Immunol. Immunother. 110; Irie and Morton, 83 Proc. Natl. Acad. Sci. U.S.A. 8694 (1986)).

IgM is one of five human antibody isotypes; IgG, IgA, IgE, and IgD are the others. IgM is typically the first antibody produced in a humoral immune response because the position of IgM heavy chain constant genes allows it to be produced without isotype switching (Charles A. Janeway, et al. Immunobiology 9-12 ($5^{th}$ ed. 2001)). Because IgM is often produced before genetic maturation occurs, this class of antibody isotype typically has lower affinity for a given antigen than other isotypes (Id). IgM compensates for low affinity by forming polymers, which increase the avidity of the antibody molecule (Id). Polymeric IgM usually forms as a pentamer associated with J-chain (a ~15 kD molecule that promotes antibody polymerization); however, it can also polymerize as a pentamer or hexamer in the absence of J-chain (Id. at 4-19). In some instances, the polymeric state of IgM allows it to mediate highly effective activation of the complement pathway in the presence of pathogens. For example, J-chain-containing pentameric IgM is not usually effective in activating complement unless it undergoes a structural change when bound to an antigen (Id. at 9-17). In contrast, J-chain-free or hexameric IgM has been shown to activate complement up to 100-fold better than pentameric IgM (Weirsma et al., 160 J. Immunol. 5979 (1998)).

Cancer is a global health problem. Though progress has been made in treating various forms of this disease, improved therapeutics are needed. Immunotherapeutics are thought to have great potential for cancer therapy. An IgM antibody specific for an antigen expressed by cancer cells may prove to be an effective cancer therapeutic.

SUMMARY

Described herein are isolated antibodies and antigen-binding fragments that specifically bind to ganglioside GD2. In some embodiments, the antibodies or antigen-binding fragments are IgMs. In some embodiments, the antibodies or antigen-binding fragments are pentameric or hexameric. While the antibodies or antigen-binding fragments may be human, humanized, or chimeric, the antibodies or antigen-binding fragments are preferably human. The antibodies or antigen-binding fragments may include a heavy chain having an amino acid sequence substantially the same as or identical to SEQ ID NO: 40 and a light chain having an amino acid sequence substantially the same as or identical to SEQ ID NO: 42. In some embodiments, antibodies or antigen-binding fragments may include a heavy chain CDR1 amino acid sequence substantially the same as, or identical to, SEQ ID NO: 10. In some embodiments, antibodies or antigen-binding fragments may include a heavy chain CDR2 amino acid sequence substantially the same as, or identical to, SEQ ID NO: 11. In some embodiments, antibodies or antigen-binding fragments may include a heavy chain CDR3 amino acid sequence substantially the same as, or identical to, SEQ ID NO: 12. In some embodiments, antibodies or antigen-binding fragments may include a light chain CDR1 amino acid sequence substantially the same as, or identical to, SEQ ID NO: 26. In some embodiments, antibodies or antigen-binding fragments may include a light chain CDR2 amino acid sequence substantially the same as, or identical to, SEQ ID NO: 27. In some embodiments, antibodies or antigen-binding fragments may include a light chain CDR3 amino acid sequence substantially the same as, or identical to, SEQ ID NO: 28. The antibodies or antigen-binding fragments may include a heavy chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12. The antibodies or antigen-binding fragments may include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. The antibodies or antigen-binding fragments may include a heavy chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12, and also have a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28.

The antibodies or antigen-binding fragments may include a heavy chain FWR1 amino acid sequence substantially the same as, or identical to, SEQ ID NO: 13. In some embodiments, the antibodies or antigen-binding fragments include a heavy chain FWR2 amino acid sequence substantially the same as, or identical to, SEQ ID NO: 14. In some embodiments, the antibodies or antigen-binding fragments include a heavy chain FWR3 amino acid sequence substantially the same as, or identical to, SEQ ID NO: 15. In some embodiments, the antibodies or antigen-binding fragments include a light chain FWR1 amino acid sequence substantially the same as, or identical to, SEQ ID NO: 29. In some embodiments, the antibodies or antigen-binding fragments include a light chain FWR2 amino acid sequence substantially the same as, or identical to, SEQ ID NO: 30. In some embodiments, the antibodies or antigen-binding fragments include a light chain FWR3 amino acid sequence substantially the same as, or identical to, SEQ ID NO: 31. In some embodiments, the antibodies or antigen-binding fragments include a heavy chain having a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15. In some embodiments, the antibodies or antigen-binding fragments include a light chain having a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. In some embodiments the antibodies or antigen-binding fragments may include a heavy chain and a light chain, wherein the heavy chain includes a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain includes a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31.

In some embodiments, the antibodies or antigen-binding fragments include a heavy chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15. In some embodiments, the antibodies or antigen-binding fragments include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. In some embodiments, the antibodies or antigen-binding fragments have a heavy and a light chain, wherein the heavy chain has a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain has a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. Antigen-binding arrangements of CDRs and FWRs may also be engineered using antibody-like proteins as CDR scaffolding. Such engineered antigen-binding proteins are within the scope of the disclosure.

The described antibodies or antigen-binding fragments may include a heavy chain that has an amino acid sequence substantially the same as, or identical to, SEQ ID NO: 40. In some embodiments, a polynucleotide substantially the same as, or identical to, SEQ ID NO: 39 may encode this heavy chain amino acid sequence. The described antibodies or antigen-binding fragments may include a light chain that has an amino acid sequence substantially the same as, or identical to, SEQ ID NO: 42. In some embodiments, a polynucleotide substantially the same as, or identical to, SEQ ID NO: 41 may encode this light chain amino acid sequence. The described antibodies or antigen-binding fragments may include a heavy and a light chain, wherein the heavy chain has an amino acid sequence substantially the same as, or identical to, SEQ ID NO: 40, and the light chain has an amino acid sequence substantially the same as, or identical to, SEQ ID NO: 42.

In some embodiments, the antibodies are produced by antibody-producing cells deposited with the Amer. Type Cult. Coll. (10801 University Blvd., Manassas, Va. 20110-2209) on Jul. 16, 2008 and have been assigned Accession No. PTA-9376. In some embodiments, the antibodies, or antigen-binding fragments thereof, have the binding affinity for GD2 of the antibodies produced by the deposited antibody-producing cells. In some embodiments, the disclosed antibodies, or antigen-binding fragments thereof, comprise the heavy and light chain CDRs of the antibodies produced by the deposited antibody-producing cells. In some embodiments, the antibodies, or antigen-binding fragments thereof, comprise the heavy and light chain variable regions of the antibodies produced by the deposited antibody-producing cells. In some embodiments, the antibodies, or antigen-binding fragments thereof, exhibit substantially the same, or greater, level of complement-dependent cytotoxic activity as antibodies produced by the deposited antibody-producing cells. In addition, antibodies, or antigen-binding fragments thereof, that compete with the antibodies produced by the deposited cells for binding to GD2 are contemplated to be within the scope of the antibodies described herein. For instance, an antibody may compete with another antibody, or an antigen-binding fragment, if it prevents or hinders the other antibody from binding to an antigenic site to which the antibody would otherwise bind in the absence of the competing antibody.

Also disclosed are polynucleotides that encode antibodies or antigen-binding fragments that specifically bind to GD2. In some embodiments, the polynucleotides encode an antibody or antigen-binding fragment thereof having a heavy chain CDR1 sequence substantially the same as, or identical to, SEQ ID NO: 10, for example SEQ ID NO: 2. In some embodiments, the polynucleotides encode an antibody or antigen-binding fragment thereof having a heavy chain CDR2 substantially the same as, or identical to, SEQ ID NO: 11, for example SEQ ID NO: 3. In some embodiments, the polynucleotides encode an antibody or antigen-binding fragment thereof having a heavy chain CDR3 substantially the same as, or identical to, SEQ ID NO: 12, for example SEQ ID NO: 4. In some embodiments, the polynucleotides encode an antibody or antigen-binding fragment thereof having a light chain CDR1 substantially the same as, or identical to, SEQ ID NO: 26, for example SEQ ID NO: 18. In some embodiments, the polynucleotides encode an antibody or antigen-binding fragment thereof having a light chain CDR2 substantially the same as, or identical to, SEQ ID NO: 27, for example SEQ ID NO: 19. In some embodiments, the polynucleotides encode an antibody or antigen-binding fragment thereof having a light chain CDR3 substantially the same as, or identical to, SEQ ID NO: 28, for example SEQ ID NO: 20. The polynucleotides may encode an antibody or antigen-binding fragment thereof having a heavy chain with a CDR1 substantially the same as, or identical to, SEQ ID NO: 10, for example SEQ ID NO: 2; a CDR2 substantially the same as, or identical to, SEQ ID NO: 11, for example SEQ ID NO: 3; and a CDR3 substantially the same as, or identical to, SEQ ID NO: 12, for example SEQ ID NO: 4. The polynucleotides may encode an antibody or antigen-binding fragment thereof having a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20. The polynucleotides may encode an antibody or antigen-binding fragment thereof having a heavy chain CDR1 substantially the same as, or identical to, SEQ ID NO: 10, for example SEQ ID NO: 2; a CDR2 encoded by a nucleotide sequence substantially the same as, or identical to, SEQ ID NO: 11, for example SEQ ID NO: 3; and a CDR3 encoded by a nucleotide sequence substantially the same as, or identical to, SEQ ID NO: 12, for example SEQ ID NO: 4; and a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20. Antigen-binding arrangements of CDRs may also be engineered using antibody-like proteins as CDR scaffolding. Such engineered antigen-binding proteins are within the scope of the disclosure.

In some embodiments, the polynucleotides encode an antibody or antigen-binding fragment thereof having a heavy chain FWR1 substantially the same as, or identical to, SEQ ID NO: 13, for example SEQ ID NO: 5. In some embodiments, the polynucleotides encode an antibody or antigen-binding fragment thereof having a heavy chain FWR2 substantially the same as, or identical to, SEQ ID NO: 14, for example SEQ ID NO: 6. In some embodiments, the polynucleotides encode an antibody or antigen-binding fragment thereof having a heavy chain FWR3 substantially the same as, or identical to, SEQ ID NO: 15, for example SEQ ID NO: 7. In some embodiments, the polynucleotides encode an antibody or antigen-binding fragment thereof having a light chain FWR1 substantially the same as, or identical to, SEQ ID NO: 29, for example SEQ ID NO: 21. In some embodiments, the polynucleotides encode an antibody or antigen-binding fragment thereof having a light chain FWR2 substantially the same as, or identical to, SEQ ID NO: 30, for example SEQ ID NO: 22. In some embodiments, the polynucleotides encode an antibody or antigen-binding fragment thereof having a light chain FWR3 substantially the same as, or identical to, SEQ ID NO: 31, for example SEQ ID NO: 23. In some embodiments, the polynucleotides encode an antibody or antigen-binding fragment thereof having a heavy chain FWR1 substantially the same as, or identical to, SEQ ID NO: 13, for example SEQ ID NO: 5; a FWR2 substantially the same as, or identical to, SEQ ID NO: 14, for example SEQ ID NO: 6; and a FWR3 substantially the same as, or identical to, SEQ ID NO: 15, for example SEQ ID NO: 7. In some embodiments, the polynucleotides encode an antibody or antigen-binding fragment thereof having a light FWR1 substantially the same as, or identical to, SEQ ID NO: 29, for example SEQ ID NO: 21; a FWR2 substantially the same as, or identical to, SEQ ID NO: 30, for example SEQ ID NO: 22; and a FWR3 substantially the same as, or identical to, SEQ ID NO: 31, for example SEQ ID NO: 23. In some embodiments, the polynucleotides encode an antibody or antigen-binding fragment thereof having a heavy chain and a light chain, wherein a heavy chain FWR1 is substantially the same as, or identical to, SEQ ID NO: 13, for example SEQ ID NO: 5; a heavy chain FWR2 is substantially the same as, or identical to, SEQ ID NO: 14, for example SEQ ID NO: 6; and a heavy chain FWR3 is substantially the same as, or identical to, SEQ ID NO: 15, for example SEQ ID NO: 7; and a light chain FWR1 is substantially the same as, or identical to, SEQ ID NO: 29, for example SEQ ID NO: 21; a light chain FWR2 is substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; and a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7. In some embodiments, the polynucleotides encode an antibody or antigen-binding fragment thereof having a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; and a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy and a light chain, wherein the polynucleotides encode a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7; and a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23. Polynucleotides encoding engineered antigen-binding proteins also are within the scope of the disclosure.

Vectors comprising the antibody- and antigen-binding fragment-encoding polynucleotides are provided, as are cells expressing the antibodies or antigen-binding fragments that specifically bind to GD2.

Described herein are methods for treating or preventing GD2-associated disease in a subject in need of such treatment. In some embodiments, the GD2-associated disease is cancer. In some embodiments, the GD2-associated disease is melanoma. The methods comprise administering to the subject an antibody or antigen-binding fragment thereof that specifically binds to GD2 in an amount effective to treat or prevent the GD2-associated disease. In some embodiments the methods comprise administering a pharmaceutical composition including an antibody or antigen-binding fragment thereof and a pharmaceutically acceptable carrier. In some aspects, the antibody or antigen-binding fragment thereof is an IgM antibody or antigen-binding fragment. In some embodiments, the described methods of treating or preventing GD2-associated disease in a subject may be carried out with an antibody, or antigen-binding fragment, that competes for binding with the GD2-specific antibodies described herein.

Described herein are methods for detecting GD2-expressing cells in vivo or in vitro. The methods may include administering to a subject an antibody or antigen-binding fragment thereof described herein that specifically binds to GD2 to allow for the detection or localization in a subject. In some embodiments, the described antibodies or antigen-binding fragments may be detectably labeled. Such detectable labels may include fluorescent labels, radiolabels, biotin, and the like. Alternatively, in some embodiments the GD2-specific antibodies or antigen-binding fragments are not labeled and, instead are detected by a secondary antibody which is detectably labeled. In some embodiments, the described methods of detection may be carried out with an antibody, or antigen-binding fragment, that competes for binding with the GD2-specific antibodies and antigen-binding fragments described herein.

Described herein are methods of making and purifying or isolating IgM antibodies or antigen-binding fragments thereof. The methods include culturing a host cell under conditions suitable to produce the antibodies or an antigen-binding fragments, recovering the antibodies or antigen-binding fragments from the cell culture, and purifying or isolating the recovered antibodies or antigen-binding fragments. Also featured are methods of purifying or isolating IgM antibodies or antigen-binding fragments, including optionally washing the antibodies or an antigen-binding fragments with a detergent, applying a solution comprising the antibodies or antigen-binding fragments to an affinity chromatography column, applying eluate from the affinity chromatography column to a cation exchange chromatography column, and applying eluate from the cation exchange chromatography column to a hydroxyapatite chromatography column and recovering the eluate from the hydroxyapatite chromatography column.

Additional methods include enhancing the viability of cultured eukaryotic cells by supplementing cell culture media with compositions comprising amino acids, sugars, and vitamins. In some embodiments the compositions may comprise glucose, glutamate, aspartate, serine, histidine, threonine, arginine, tyrosine, cysteine, valine, methionine, tryptophan, phenylalanine, isoleucine, leucine, lysine, proline, nicotinic acid amide, pyridoxine HCl, folic acid, vitamin B-12, riboflavin, and thiamine HCl. Described herein are also methods for enhancing protein production by cells modified to produce proteins. In one aspect, these methods include supplementing the growth media of cells with valeric acid.

Described herein are protein conjugates of albumin, for example bovine serum albumin (BSA), and a ganglioside and methods for producing such protein conjugates. In one embodiment, the conjugated ganglioside may be GD2. In one embodiment, the conjugated ganglioside may be GM2. In one embodiment, the conjugated ganglioside may be GM3. In one embodiment, albumin is conjugated to a reducing end of a carbohydrate moiety of a ganglioside by reductive amination. In one embodiment, the reductive amination is catalyzed by sodium cyanoborohydride.

BRIEF DESCRIPTION OF THE DRAWINGS

FIG. 1 shows variable antigen specificity of antibodies present in the supernatant of an Epstein-Barr Virus-transformed human lymphoblast pool (HLP) as determined by ELISA.

FIG. 2A serves as negative control, showing binding in the absence of GD2-specific primary antibody. FIGS. 2B and 2C show binding of HLP-derived IgM obtained from cell culture supernatants concentrated to either 8.1× or 14.2×, respectively. FIG. 2D shows binding of a murine GD2-specific IgM antibody produced by murine hybridoma HB-8568™ (ATCC #HB 8568™) and serves as a positive control.

FIG. 3 shows an antigen-specific ELISA using spent medium from hybridoma clones generated by the HLP-derived hybridomas.

FIG. 4A serves as negative control, showing lack of binding in the absence of GD2-specific primary antibody. FIG. 4B, which serves as a positive control, shows binding of a murine GD2-specific IgM antibody produced by HB-8568™ cells. FIGS. 4C and D show binding of IgM produced by 3B2 and 1470 hybridoma cells, respectively.

DETAILED DESCRIPTION OF ILLUSTRATIVE EMBODIMENTS

Figure 1A:
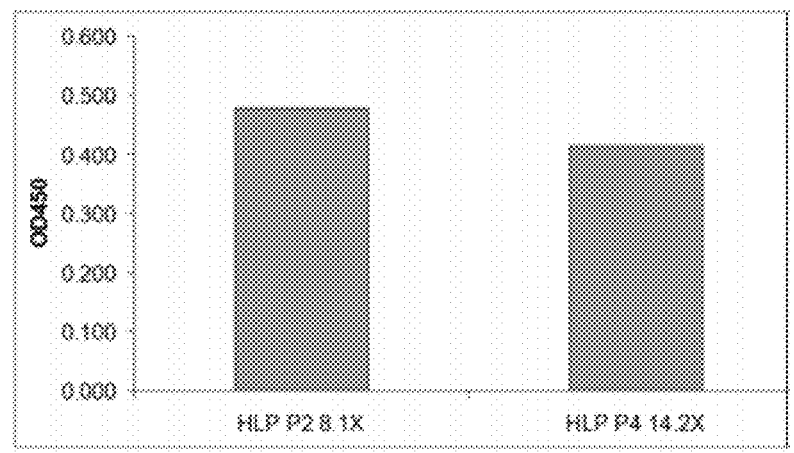
FIG. 1A demonstrates that concentrated cell culture supernatants from the HLP, at cell passage 2 (8.1× concentrated) or 4 (14.2× concentrated), contain IgM antibodies specific for GD2.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

As used herein, the term "cytotoxic" or "cytostatic" agent refers to an agent that inhibits the biological processes of a cell, or reduces the viability or proliferative potential of a cell. Cytotoxic or cytostatic agents may function in a variety of ways, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutic agents include, but are not limited to, synthetic compounds, natural and recombinant bacterial toxins, natural and recombinant fungal toxins, natural and recombinant plant toxins, fissionable nuclides, and radionuclides. Specific examples of chemotherapeutic agents include, but are not limited to, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, lead-212, bismuth-212, astatine-211, iodine-131, scandium-47, rhenium-186, rhenium-188, yttrium-90, iodine-123, iodine-124, iodine-125, bromine-77, indium-111, boron-10, actinide, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, 5-fluorouracil, cyclophosphamide and certain cytokines such as TNF-alpha and TNF-beta.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Substantially the same" with respect to nucleic acid or amino acid sequences, means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. Such identity may be determined using mBLAST algorithm (Altschul et al. (1990) Proc. Natl. Acad. Sci. USA 87:2264-8; Karlin and Altschul (1993) Proc. Natl. Acad. Sci. USA 90:5873-7).

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences may be operably linked to promoters or regulatory sequences in a sense or antisense orientation. The term "operably linked" is sometimes applied to the arrangement of other transcription control elements (e.g., enhancers) in an expression vector.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts, monographs, and research literature. Modifications may occur anywhere in a polypeptide, including the peptide backbone, the amino acid side-chains and the amino or carboxyl termini. The same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62).

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

"Effective amount" and "therapeutically effective amount" are used interchangeably herein, and refer to an amount of an antibody, antigen-binding fragment, or antibody composition, as described herein, effective to achieve a particular biological or therapeutic result such as, but not limited to, biological or therapeutic results disclosed, described, or exemplified herein. A therapeutically effective amount of the antibody or antigen-binding fragment thereof may vary according to factors such as the disease state, age, sex, and weight of the individual, and the ability of the antibody or antigen-binding fragment thereof to elicit a desired response in the individual. Such results may include, but are not limited to, the treatment of cancer, as determined by any means suitable in the art.

"Pharmaceutically acceptable" refers to those properties and substances which are acceptable to the patient from a pharmacological/toxicological point of view and to the manufacturing pharmaceutical chemist from a physical/chemical point of view regarding composition, formulation, stability, patient acceptance, and bioavailability.

"Pharmaceutically acceptable carrier" refers to a medium that does not interfere with the effectiveness of the biological activity of the active ingredient(s) and is not toxic to the host to which it is administered.

"Antibody" refers to all isotypes of immunoglobulins (IgG, IgA, IgE, IgM, IgD, and IgY) including various monomeric and polymeric forms of each isotype, unless otherwise specified.

Antigen-binding fragments are any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, or molecules, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

"Antibody compositions" refer to antibodies or binding fragments thereof that are coupled with at least one pharmaceutically acceptable carrier, chemotherapeutic agent, or diagnostic moiety, such as 111In-1,4,7,10-tetraazacyclododecane-N,N',N",N'"-tetraacetic acid ($^{111}$In-DOTA).

"Specific binding" refers to the ability of an antibody, or antigen-binding fragment, to bind to a particular biomolecule with an affinity that is greater than that with which it may bind other biomolecules.

The embodiments described herein are not limited to particular methods, reagents, compounds, compositions or biological systems, which can, of course, vary. Furthermore, the terminology used herein is for the purpose of describing particular antibodies or antigen-binding fragments only, and is not intended to be limiting.

GD2-Specific Antibodies

Described herein are isolated antibodies or antigen-binding fragments that specifically bind the ganglioside GD2. In one embodiment, the antibody or antigen-binding fragment thereof is a monoclonal antibody or antigen-binding fragment; however, other embodiments include GD2-specific polyclonal antibodies and derivatives or fragments of antibodies that retain specificity for GD2. The general structure of an antibody molecule comprises an antigen binding domain, which includes heavy and light chains, and the Fc domain, which serves a variety of functions, including complement fixation. In some embodiments, the antibodies or antigen-binding fragments mediate complement-dependent cytotoxicity.

There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM isotypes, respectively. The described antibodies or antigen-binding fragments include all isotypes and synthetic multimers of the four-chain immunoglobulin structure. The described antibodies or antigen-binding fragments also include the IgY isotype generally found in hen or turkey serum and hen or turkey egg yolk. Antibodies or antigen-binding fragments non-covalently, specifically, and reversibly bind an antigen.

The antibodies or antigen-binding fragments of the disclosed subject matter may be derived from any species. For example, the antibodies or antigen-binding fragments may be mouse, rat, goat, horse, swine, bovine, chicken, rabbit, donkey, human, and the like. For use in the treatment of humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" antibody, or antigen-binding fragment, means an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a mouse antigen binding domain with a human Fc or other such structural domain.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FWR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FWR regions are those of a human immunoglobulin sequence. The humanized antibody optimally also will comprise at least a portion of an immunoglobulin constant region (Fc), typically that of a human immunoglobulin. For further details, see Jones et al., 321 Nature 522-5 (1986); Reichmann et al., 332 Nature 323-9 (1988); and Presta, 2 Curr. Op. Struct. Biol. 593-6 (1992).

In some cases, the described antibodies are human antibodies or antigen binding fragments thereof. As used herein, the term "human antibody" means that the antibody is either solely from human origin or an antibody in which the variable and constant domain sequences are human sequences. The term encompasses antibodies with sequences derived from (i.e., that utilize) human genes, but which have been changed, e.g., to decrease possible immunogenicity, increase affinity, eliminate cysteines that may cause undesirable folding, etc. The term encompasses such antibodies produced recombinantly in non-human cells, which may impart glycosylation not typical of human cells.

The antibodies or antigen-binding fragments described herein may be labeled or otherwise conjugated to various chemical or biomolecule moieties, for example, for therapeutic or diagnostic applications. The moieties may be cytotoxic, for example, bacterial toxins, viral toxins, radioisotopes, and the like. The moieties may be detectable labels, for example, fluorescent labels, radiolabels, biotin, and the like, for example, $^{111}$In-DOTA, $^{111}$In-diethylenetriaminepentaacetic acid (DTPA), or radionuclides, such as, but not limited to, lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide.

In some embodiments, the antibodies or antigen-binding fragments are conjugated to one or more chemotherapeutic agents such as, but not limited to radionuclides, toxins, cytotoxic and cytostatic agents. In other embodiments the antibodies or antigen-binding fragments are used in combination with one or more chemotherapeutic agents. The antibodies or antigen-binding fragments described herein may be used alone or with (e.g., coadministered or conjugated to) a biomolecule or chemotherapeutic agent such as a cytotoxic or cytostatic agent. In some embodiments, the chemotherapeutic agent is a radionuclide, including, but not limited to lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. In other embodiments, the chemotherapeutic agent is a toxin or cytotoxic drug, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, pemetrexed, cisplatinum, vindesine, adriamycin, vincristine, vinblastine, BCNU, a taxane (e.g., Taxol™), tarceva, avastin, mitomycin, 5-fluorouracil, cyclophosphamide, certain cytokines such as TNF-alpha and TNF-beta, and the like. Methods of conjugation of antibodies or antigen-binding fragments to such agents are known in the literature.

Antibody specificity is primarily determined by the six CDR regions, especially H chain CDR3 (Kala et al., 132 J. Biochem. 535-41 (2002); Morea et al., 275 J. Mol. Biol. 269-94 (1998); and, Chothia et al., 196 J. Mol. Biol. 901-17 (1987)). Antibody framework regions, however, can play a role in antigen-antibody interactions (Panka et al., 85 Proc. Natl. Acad. Sci. USA 3080-4 (1988)), particularly in influencing the conformation of CDR loops (Foote et al., 224 J. Mol. Biol. 487-99 (1992)). Thus, the described antibodies or antigen-binding fragments may comprise any combination of H or L chain CDR or FWR regions that confer specificity to GD2. Domain shuffling experiments, which are routinely carried out in the art (Jirholt et al., 215 Gene 471-6 (1998); Soderlind et al., 18 Nature Biotechnology 852-6 (2000)), may be employed to generate antibodies that specifically bind GD2 according to the specifications described and exemplified herein. Antibodies or antigen-binding fragments generated by such domain shuffling experiments are within the scope of the antibodies or antigen-binding fragments described herein. Furthermore, CDRs may also be arranged to bind a given antigen by engineering antibody-like proteins to serve as CDR scaffolding (Nicaise et al., 13 Protein Sci. 1882 (2004)). Such antigen-binding proteins are within the scope of the antibodies described herein.

The antibodies or antigen-binding fragments described herein can occur in a variety of forms, but will include one or more of the antibody segments shown in Table 1.

TABLE 1

Antibody segments of the described antibodies and antigen-binding fragments thereof ("Lc" denotes light chain and "Hc" denotes heavy chain).

| AB527 Antibody Segment | Amino Acid SEQ ID NO. | DNA SEQ ID NO. |
|---|---|---|
| Lc CDR1 | 26 | 18 |
| Lc CDR2 | 27 | 19 |
| Lc CDR3 | 28 | 20 |
| Lc FWR1 | 29 | 21 |
| Lc FWR2 | 30 | 22 |

TABLE 1-continued

Antibody segments of the described antibodies and antigen-binding fragments thereof ("Lc" denotes light chain and "Hc" denotes heavy chain).

| AB527 Antibody Segment | Amino Acid SEQ ID NO. | DNA SEQ ID NO. |
|---|---|---|
| Lc FWR3 | 31 | 23 |
| Lc variable domain | 32 | 24 |
| Light chain | 42 | 41 |
| Hc CDR1 | 10 | 2 |
| Hc CDR2 | 11 | 3 |
| Hc CDR3 | 12 | 4 |
| Hc FWR1 | 13 | 5 |
| Hc FWR2 | 14 | 6 |
| Hc FWR3 | 15 | 7 |
| Hc variable domain | 16 | 8 |
| Heavy chain | 40 | 39 |

In some embodiments, the antibodies or antigen-binding fragments may include a heavy chain CDR1 amino acid sequence substantially the same as, or identical to, SEQ ID NO: 10. In some embodiments, the antibodies or antigen-binding fragments may include a heavy chain CDR2 amino acid sequence substantially the same as, or identical to, SEQ ID NO: 11. In some embodiments, antibodies or antigen-binding fragments may include a heavy chain CDR3 amino acid sequence substantially the same as, or identical to, SEQ ID NO: 12. In some embodiments, antibodies or antigen-binding fragments may include a light chain CDR1 amino acid sequence substantially the same as, or identical to, SEQ ID NO: 26. In some embodiments, antibodies or antigen-binding fragments may include a light chain CDR2 amino acid sequence substantially the same as, or identical to, SEQ ID NO: 27. In some embodiments, antibodies or antigen-binding fragments may include a light chain CDR3 amino acid sequence substantially the same as, or identical to, SEQ ID NO: 28. In some embodiments, antibodies or antigen-binding fragments may include a heavy chain CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12. In some embodiments, antibodies or antigen-binding fragments may include a light chain CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. In some embodiments, antibodies or antigen-binding fragments may include a heavy chain and a light chain, wherein the heavy chain has a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; and the light chain has a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. Antigen-binding arrangements of CDRs may also be engineered using antibody-like proteins as CDR scaffolding. Such engineered antigen-binding proteins are within the scope of the disclosure.

In some embodiments, antibodies or antigen-binding fragments may include a heavy chain FWR1 amino acid sequence substantially the same as, or identical to, SEQ ID NO: 13. In some embodiments, antibodies or antigen-binding fragments may include a heavy chain FWR2 amino acid sequence substantially the same as, or identical to, SEQ ID NO: 14. In some embodiments, antibodies or antigen-binding fragments may include a heavy chain FWR3 amino acid sequence substantially the same as, or identical to, SEQ ID NO: 15. In some embodiments, antibodies or antigen-binding fragments may include a light chain FWR1 amino acid sequence substantially the same as, or identical to, SEQ ID NO: 29. In some embodiments, antibodies or antigen-binding fragments may include a light chain FWR2 amino acid sequence substantially the same as, or identical to, SEQ ID NO: 30. In some embodiments, antibodies or antigen-binding fragments may include a light chain FWR3 amino acid sequence substantially the same as, or identical to, SEQ ID NO: 31. In some embodiments, antibodies or antigen-binding fragments may include a heavy chain having a FWR1 amino acid sequence that is substantially the same as, or identical to, SEQ ID NO: 13; a FWR2 amino acid sequence that is substantially the same as, or identical to, SEQ ID NO: 14; and a FWR3 amino acid sequence that is substantially the same as, or identical to, SEQ ID NO: 15. In some embodiments, antibodies or antigen-binding fragments may include a light chain having a FWR1 amino acid sequence that is substantially the same as, or identical to, SEQ ID NO: 29; a FWR2 amino acid sequence that is substantially the same as, or identical to, SEQ ID NO: 30; and a FWR3 amino acid sequence that is substantially the same as, or identical to, SEQ ID NO: 31. In some embodiments, antibodies or antigen-binding fragments may include a heavy chain and a light chain, wherein the heavy chain includes a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain includes a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31.

In some embodiments, antibodies or antigen-binding fragments may include a heavy chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15. In some embodiments, the antibodies or antigen-binding fragments include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. In some embodiments, the antibodies or antigen-binding fragments include a heavy and a light chain, wherein the heavy chain includes a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain includes a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. Antigen-binding arrangements of CDRs and FWRs may also be engineered using antibody-like proteins as CDR scaffolding. Such engineered antigen-binding proteins are within the scope of the disclosure.

In some embodiments, the antibodies or antigen-binding fragments described herein have a heavy chain that includes the amino acid sequence substantially the same as, or identical to, SEQ ID NO: 40. In some embodiments, the antibodies or antigen-binding fragments described herein have a light chain that includes the amino acid sequence substantially the same as, or identical to, SEQ ID NO: 42. The described antibodies or antigen-binding fragments may have a heavy and a light chain, wherein the heavy chain includes the amino acid sequence substantially the same as, or identical to, SEQ ID NO: 40 and the light chain includes the amino acid sequence substantially the same as, or identical to, SEQ ID NO: 42.

Also described are polynucleotides that encode antibodies or antigen-binding fragments that specifically bind to GD2. In some embodiments, the polynucleotides encode an antibody or antigen-binding fragment thereof having a heavy chain CDR1 sequence substantially the same as, or identical to, SEQ ID NO: 10, for example SEQ ID NO: 2. In some embodiments, the polynucleotides encode an antibody or antigen-binding fragment thereof having a heavy chain CDR2 substantially the same as, or identical to, SEQ ID NO: 11, for example SEQ ID NO: 3. In some embodiments, the polynucleotides encode an antibody or antigen-binding fragment thereof having a heavy chain CDR3 substantially the same as, or identical to, SEQ ID NO: 12, for example SEQ ID NO: 4. In some embodiments, the polynucleotides encode an antibody or antigen-binding fragment thereof having a light chain CDR1 substantially the same as, or identical to, SEQ ID NO: 26, for example SEQ ID NO: 18. In some embodiments, the polynucleotides encode an antibody or antigen-binding fragment thereof having a light chain CDR2 substantially the same as, or identical to, SEQ ID NO: 27, for example SEQ ID NO: 19. In some embodiments, the polynucleotides encode an antibody or antigen-binding fragment thereof having a light chain CDR3 substantially the same as, or identical to, SEQ ID NO: 28, for example SEQ ID NO: 20. The polynucleotides may encode an antibody or antigen-binding fragment thereof having a heavy chain with a CDR1 substantially the same as, or identical to, SEQ ID NO: 10, for example SEQ ID NO: 2; a CDR2 substantially the same as, or identical to, SEQ ID NO: 11, for example SEQ ID NO: 3; and a CDR3 substantially the same as, or identical to, SEQ ID NO: 12, for example SEQ ID NO: 4. The polynucleotides may encode an antibody or antigen-binding fragment thereof having a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20. The polynucleotides may encode an antibody or antigen-binding fragment thereof having a heavy chain CDR1 substantially the same as, or identical to, SEQ ID NO: 10, for example SEQ ID NO: 2; a CDR2 encoded by a nucleotide sequence substantially the same as, or identical to, SEQ ID NO: 11, for example SEQ ID NO: 3; and a CDR3 encoded by a nucleotide sequence substantially the same as, or identical to, SEQ ID NO: 12, for example SEQ ID NO: 4; and a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20.

In some embodiments, the polynucleotides encode an antibody or antigen-binding fragment thereof having a heavy chain FWR1 substantially the same as, or identical to, SEQ ID NO: 13, for example SEQ ID NO: 5. In some embodiments, the polynucleotides encode an antibody or antigen-binding fragment thereof having a heavy chain FWR2 substantially the same as, or identical to, SEQ ID NO: 14, for example SEQ ID NO: 6. In some embodiments, the polynucleotides encode an antibody or antigen-binding fragment thereof having a heavy chain FWR3 substantially the same as, or identical to, SEQ ID NO: 15, for example SEQ ID NO: 7. In some embodiments, the polynucleotides encode an antibody or antigen-binding fragment thereof having a light chain FWR1 substantially the same as, or identical to, SEQ ID NO: 29, for example SEQ ID NO: 21. In some embodiments, the polynucleotides encode an antibody or antigen-binding fragment thereof having a light chain FWR2 substantially the same as, or identical to, SEQ ID NO: 30, for example SEQ ID NO: 22. In some embodiments, the polynucleotides encode an antibody or antigen-binding fragment thereof having a light chain FWR3 substantially the same as, or identical to, SEQ ID NO: 31, for example SEQ ID NO: 23. In some embodiments, the polynucleotides encode an antibody or antigen-binding fragment thereof having a heavy chain FWR1 substantially the same as, or identical to, SEQ ID NO: 13, for example SEQ ID NO: 5; a FWR2 substantially the same as, or identical to, SEQ ID NO: 14, for example SEQ ID NO: 6; and a FWR3 substantially the same as, or identical to, SEQ ID NO: 15, for example SEQ ID NO: 7. In some embodiments, the polynucleotides encode an antibody or antigen-binding fragment thereof having a light FWR1 substantially the same as, or identical to, SEQ ID NO: 29, for example SEQ ID NO: 21; a FWR2 substantially the same as, or identical to, SEQ ID NO: 30, for example SEQ ID NO: 22; and a FWR3 substantially the same as, or identical to, SEQ ID NO: 31, for example SEQ ID NO: 23. In some embodiments, the polynucleotides encode an antibody or antigen-binding fragment thereof having a heavy chain and a light chain, wherein a heavy chain FWR1 is substantially the same as, or identical to, SEQ ID NO: 13, for example SEQ ID NO: 5; a heavy chain FWR2 is substantially the same as, or identical to, SEQ ID NO: 14, for example SEQ ID NO: 6; and a heavy chain FWR3 is substantially the same as, or identical to, SEQ ID NO: 15, for example SEQ ID NO: 7; and a light chain FWR1 is substantially the same as, or identical to, SEQ ID NO: 29, for example SEQ ID NO: 21; a light chain FWR2 is substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; and a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7. In some embodiments, the polynucleotides encode an antibody or antigen-binding fragment thereof having a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; and a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy and a light chain, wherein the polynucleotides encode a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7; and a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23.

Polynucleotides encoding engineered antigen-binding proteins also are within the scope of the disclosure.

In some embodiments, the polynucleotides described (and the peptides they encode) include a leader sequence. Any leader sequence known in the art may be employed. The leader sequence may include, but is not limited to, a restriction site or a translation start site. In some embodiments, the leader sequence has the nucleic acid sequence ATGGGATGGAGCTGTATCATCCTCTTCTTGGTAGCAACAGCTACAGGTGTACACAGC (SEQ ID NO: 43). In some embodiments, the leader sequence encodes the amino acid sequence MGWSCIILFLVATATGVHS (SEQ ID NO: 44).

Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, some embodiments include antibodies or antigen-binding fragments having 90%, 95%, 96%, 97%, 98%, or 99% homology to the antibodies or antigen-binding fragments herein. Other embodiments include GD-2 specific antibodies or antigen-binding fragments, that have framework, scaffold, or other non-binding regions that do not share significant homology with the antibodies and antigen-binding fragments described herein, but do incorporate one or more CDRs or other sequences needed to confer binding that are 90%, 95%, 96%, 97%, 98%, or 99% homologous to such sequences described herein.

The antibodies or antigen-binding fragments described herein include variants having single or multiple amino acid substitutions, deletions, or additions that retain the biological properties (e.g., binding affinity or immune effector activity) of the described antibodies or antigen-binding fragments. The skilled person may produce variants having single or multiple amino acid substitutions, deletions, or additions. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The antibodies or antigen-binding fragments described herein may embody several antibody isotypes, such as IgM, IgD, IgG, IgA and IgE. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

Altering the isotype of an antibody may be useful for combining different effector functions, conferred by the antibody constant region, with antigen specificity. For example, IgG is produced in monomeric form, is effective at activating complement, and is commonly found in the plasma and intracellular compartments of the body. IgA is produced as a monomer and a J-chain-associated dimer. IgA is most commonly found in the luminal spaces of the body and breast milk, because the dimeric form may be transported across epithelial cell barriers. Like IgA, IgM can also form polymers, however, it tends to form pentamers, when associated with J-chain, and pentamers and hexamers not associated with J-chain. These highly polymeric antibodies serve to increase overall antigen-binding capability by increasing avidity without reducing affinity. Both polymeric forms of IgM can activate complement efficiently, which can result in complement-dependent cytotoxicity (CDC).

The antibodies or antigen-binding fragments described herein, in some embodiments, are polymeric IgM antibodies or antigen-binding fragments. In some embodiments, the antibodies or antigen-binding fragments are pentameric IgM antibodies or antigen-binding fragments that are associated with J-chain. In other embodiments, the antibodies or antigen-binding fragments are hexameric IgM antibodies or antigen-binding fragments that are not associated with J-chain. In some embodiments, the antibodies or antigen-binding fragments are pentameric IgM antibodies or antigen-binding fragments that are not associated with J-chain. In some embodiments, the antibodies or antigen-binding fragments are hexameric IgM antibodies or antigen-binding fragments that are associated with J-chain.

The antibodies or antigen-binding fragments described herein have binding affinities (in M) for GD2 that include a dissociation constant ($K_d$) of less than $1 \times 10^{-2}$. In some embodiments, the $K_d$ is less than $1 \times 10^{-3}$. In other embodiments, the $K_d$ is less than $1 \times 10^{-4}$. In some embodiments, the $K_d$ is less than $1 \times 10^{-5}$. In still other embodiments, the $K_d$ is less than $1 \times 10^{-6}$, $2 \times 10^{-6}$, $3 \times 10^{-6}$, $4 \times 10^{-6}$, $5 \times 10^{-6}$, $6 \times 10^{-6}$, $7 \times 10^{-6}$, $8 \times 10^{-6}$, or $9 \times 10^{-6}$. In other embodiments, the $K_d$ is less than $1 \times 10^{-7}$, $2 \times 10^{-7}$, or $3 \times 10^{-7}$, $2 \times 10^{-7}$, $3 \times 10^{-7}$, $4 \times 10^{-7}$, $5 \times 10^{-7}$, $6 \times 10^{-7}$, $7 \times 10^{-7}$, $8 \times 10^{-7}$, or $9 \times 10^{-7}$. In other embodiments, the $K_d$ is less than $1 \times 10^{-8}$, $2 \times 10^{-8}$, $3 \times 10^{-8}$, $4 \times 10^{-8}$, $5 \times 10^{-8}$, $6 \times 10^{-8}$, $7 \times 10^{-8}$, $8 \times 10^{-8}$, or $9 \times 10^{-8}$. In other embodiments, the $K_d$ is less than $1 \times 10^{-9}$, $2 \times 10^{-9}$, $3 \times 10^{-9}$, $4 \times 10^{-9}$, $5 \times 10^{-9}$, $6 \times 10^{-9}$, $7 \times 10^{-9}$, $8 \times 10^{-9}$, or $9 \times 10^{-9}$. In other embodiments, the $K_d$ is less than $1 \times 10^{-10}$, $2 \times 10^{-10}$, $3 \times 10^{-10}$, $2 \times 10^{-10}$, $3 \times 10^{-10}$, $4 \times 10^{-10}$, $5 \times 10^{-10}$, $6 \times 10^{-10}$, $7 \times 10^{-10}$, $8 \times 10^{-10}$, or $9 \times 10^{-10}$. In still other embodiments, the $K_d$ is less than $1 \times 10^{-11}$, $2 \times 10^{-11}$, $3 \times 10^{-11}$, $4 \times 10^{-11}$, $5 \times 10^{-11}$, $6 \times 10^{-11}$, $7 \times 10^{-11}$, $8 \times 10^{-11}$, or $9 \times 10^{-11}$. In some embodiments, the $K_d$ is less than $1 \times 10^{-12}$. In other embodiments, the $K_d$ is less than $1 \times 10^{-13}$. In other embodiments, the $K_d$ is less than $1 \times 10^{-14}$. In still other embodiments, the $K_d$ is less than $1 \times 10^{-15}$. In preferred embodiments, the $K_d$ is $4.5 \times 10^{-9}$ or less.

The antibodies or antigen-binding fragments described herein, in some embodiments, have specific binding affinities for GD2 in contrast with each of GD1a, GM2 or GM3. In some embodiments, the $K_d$ for GD2 differs from the $K_d$ for each of GD1a, GM2 or GM3 by at least 3-fold, preferably 10-fold.

The antibodies or antigen-binding fragments described herein may be modified, e.g., by the covalent attachment of any type of molecule to the antibody or antigen-binding fragment thereof such that covalent attachment does not prevent the antibody or antigen-binding fragment thereof from binding to its epitope. Examples of suitable modifications include, but are not limited to glycosylation, acetylation, pegylation, phosphorylation, amidation, and the like. In some embodiments the antibodies or antigen-binding fragments may themselves be derivatized by known protecting/blocking groups, proteolytic cleavage, linkage to a cellular ligand or other proteins, and the like. The antibodies or antigen-binding fragments may have post-translational moieties that improve upon antibody or antigen-binding fragment thereof activity or stability. These moieties include sulfur, methyl, carbohydrate, phosphorus as well as other chemical groups commonly found on immunoglobulin molecules. Furthermore, the antibodies or antigen-binding fragments may contain one or more non-classical amino acids.

Antibodies or antigen-binding fragments described herein may be labeled with or conjugated to toxic or non-toxic moieties. Toxic moieties include, for example, bacterial toxins, viral toxins, plant toxins, fungal toxins, radioisotopes, and the like. Antibodies or antigen-binding fragments may be labeled for use in biological assays (e.g., radioisotope labels, fluorescent labels) to aid in detection of the antibody or antigen-binding fragment. Antibodies or antigen-binding fragments may also be labeled or conjugated for diagnostic or therapeutic purposes, e.g., with radioactive isotopes that deliver radiation directly to a desired site for applications such as radioimmunotherapy (Garmestani et al., 28 Nucl. Med. Biol. 409 (2001)), imaging techniques and radioimmunoguided surgery or labels that allow for in vivo imaging or detection of specific antibody/antigen complexes. Antibodies or antigen-binding fragments may also be conjugated with toxins to provide an immunotoxin (see, Kreitman, R. J., 31 Adv. Drug Del. Rev. 53 (1998)).

Described herein are compositions comprising at least one described antibody or antigen-binding fragment thereof and a pharmaceutically acceptable carrier. Such compositions are useful, for example, for administration to patients to treat cancer, such as those described and exemplified herein. The compositions may be formulated as any of various preparations that are known and suitable in the art, including those described and exemplified herein. In some embodiments, the compositions are aqueous formulations. Aqueous solutions may be prepared by admixing the antibodies or antigen-binding fragments in water or suitable physiologic buffer, and optionally adding suitable colorants, flavors, preservatives, stabilizing and thickening agents and the like as desired. Aqueous suspensions may also be made by dispersing the antibodies or antigen-binding fragments in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions may be formulated for injection into a subject. For injection, the compositions described may be formulated in aqueous solutions such as water or alcohol, or in physiologically compatible buffers such as Hanks's solution, Ringer's solution, or physiological saline buffer. The solution may contain one or more formulatory agents such as suspending, stabilizing or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions may be formulated in sustained release vehicles or depot preparations. Such long-acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

Disclosed herein are methods for detecting GD-2-expressing cells using the described antibodies, or antigen-binding fragments, either in vivo or in vitro. Some embodiments make use of disclosed antibodies, or antigen-binding fragments, that are conjugated to detectable labels such as fluorescent labels, radiolabels, biotin, enzymes and the like, for example $^{111}$In-DOTA, $^{111}$In-DTPA, or radionuclides, including, but not limited to, lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. For example, a detectably labeled antibody, or antigen-binding fragment, may be administered to a subject to detect and localize cells in the subject that express GD2. Such methods could also be used to detect cells or tissues where GD2 is highly expressed relative to other cells or tissues in the subject. Alternatively, one embodiment of the disclosed method for detecting GD-2-expressing cells may include using a detectably labeled antibody or antigen-binding fragment, described herein, to detect or quantify the expression of GD2 by cells obtained from a subject, such as cells obtained from a blood sample or tissue biopsy.

Alternatively, the described methods for detecting GD-2-expressing cells using the described antibodies, or antigen-binding fragments, may be performed using GD2-specific antibodies that are not labeled. For example, in one embodiment, GD2-expressing cells may be detected in a subject by first administering to the subject a GD2-specific antibody, or antigen-binding fragment, described herein followed by administration of a detectably labeled secondary antibody capable of binding the GD2-specific antibody, or antigen-binding fragment, administered initially. A similar methodology could be used to detect GD2-expressing cells in vitro.

Also described herein are methods for treating or preventing diseases in subjects in need of such treatment or prevention. In some aspects, the methods can include identifying a subject in need of treatment or prevention of GD2-associated diseases, such as cancer, e.g., melanoma. Other embodiments include an antibody or antigen-binding fragment thereof that is labeled or conjugated for diagnostic purposes, e.g., with radioactive isotopes that deliver radiation directly to a desired site, such as imaging techniques or detection of specific antibody/antigen complexes. In one embodiment, the methods comprise administering to the subject a GD2-specific antibody or antigen-binding fragment, such as a recombinant, human, GD2-specific IgM antibody in an amount effective to treat or prevent disease. In one aspect the methods include administering to the subject a composition, such as those described and exemplified herein, the composition comprising a pharmaceutically acceptable carrier and at least one antibody or antigen-binding fragment thereof that specifically binds to GD2, in an amount effective to treat or prevent disease. In one embodiment, the methods comprise administering to the subject at least one antibody or antigen-binding fragment, such as the antibodies or antigen-binding fragments described and exemplified herein, that specifically binds to GD2, in an amount effective to treat or prevent disease. In one embodiment, the methods comprise administering to the subject at least one GD2-specific antibody or antigen-binding fragment thereof labeled or conjugated to toxic or non-toxic moieties exemplified herein.

The antibodies or antigen-binding fragments described herein may be administered orally in any acceptable dosage form such as capsules, tablets, aqueous suspensions, solutions or the like. The antibodies or antigen-binding fragments may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Alternatively, the antibodies or antigen-binding fragments will be intravenously or intraperitoneally, for example, by injection.

The subject may be any animal, and preferably is a mammal such as a mouse, rat, hamster, guinea pig, rabbit, cat, dog, monkey, donkey, cow, horse, pig, and the like. Most preferably, the mammal is a human. In some embodiments, subjects may be administered at least one anti-GD2 antibody or antigen-binding fragment thereof in a daily dose range of 0.01 μg to 500 mg of antibody or antigen-binding fragment thereof per kg of the weight of the subject. The dose administered to the subject may also be measured in terms of total amount of the at least one anti-GD2 antibody or antigen-binding fragment thereof administered per day. In some embodiments, a subject is administered 5 to 5000 milligrams of at least one anti-GD2 antibody or antigen-binding fragment thereof per day. In some embodiments, a subject is administered up to 10 milligrams of at least one anti-GD2 antibody or antigen-binding fragment thereof per day. In some embodiments, a subject is administered up to 100 milligrams of at least one anti-GD2 antibody or antigen-binding fragment thereof per day. In some embodiments, a subject is administered up to 250 milligrams of at least one anti-GD2 antibody or antigen-binding fragment thereof per day. In some embodiments, a subject is administered up to 500 milligrams of at least one anti-GD2 antibody or antigen-binding fragment thereof per day. In some embodiments, a subject is administered up to 750 milligrams of at least one anti-GD2 antibody or antigen-binding fragment thereof per day. In some embodiments, a subject is administered up to 1000 milligrams of at least one anti-GD2 antibody or antigen-binding fragment thereof per day. In some embodiments, a subject is administered up to 1500 milligrams of at least one anti-GD2 antibody or antigen-binding fragment thereof per day. In some embodiments, a subject is administered up to 2000 milligrams of at least one anti-GD2 antibody or antigen-binding fragment thereof per day. In some embodiments, a subject is administered up to 2500 milligrams of at least one anti-GD2 antibody or antigen-binding fragment thereof per day. In some embodiments, a subject is administered up to 3000 milligrams of at least one anti-GD2 antibody or antigen-binding fragment thereof per day. In some embodiments, a subject is administered up to 3500 milligrams of at least one anti-GD2 antibody or antigen-binding fragment thereof per day. In some embodiments, a subject is administered up to 4000 milligrams of at least one anti-GD2 antibody or antigen-binding fragment thereof per day. In some embodiments, a subject is administered up to 4500 milligrams of at least one anti-GD2 antibody or antigen-binding fragment thereof per day. In some embodiments, a subject is administered up to 5000 milligrams of at least one anti-GD2 antibody or antigen-binding fragment thereof per day. In some embodiments, antibody or antigen-binding fragment thereof is administered to a subject weekly or bi-weekly.

Treatment may be initiated with smaller dosages that are less than the optimum dose of the at least one anti-GD2 antibody or antigen-binding fragment, followed by an increase in dosage over the course of the treatment until the optimum effect under the circumstances is reached. If indicated, the total daily dosage may be divided and administered in portions throughout the day.

For effective treatment of GD2-associated diseases, one skilled in the art may recommend a dosage schedule and dosage amount adequate for the subject being treated. Dosing may occur one to four or more times daily for as long as needed. The dosing may occur less frequently if the compositions are formulated in sustained delivery vehicles. The dosage schedule may also vary depending on the active drug concentration, which may depend on the needs of the subject.

Also provided are vectors comprising the polynucleotides described herein. The vectors can be expression vectors. Recombinant expression vectors containing a sequence encoding a polypeptide of interest are thus provided. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate antibody or antigen-binding fragment-producing cells. Thus, another aspect features host cells transformed with vectors comprising a nucleic acid sequence encoding an antibody or antigen-binding fragment thereof that specifically binds GD2, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the antibodies or antigen-binding fragments described herein are preferably eukaryotic cells, more preferably cells of plant, rodent, or human origin, for example but not limited to NSO, CHO, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Once a cell expressing the desired protein is identified, it can be expanded and selected. Transformed cells may be selected in a number of ways. For example, cells may be selected for expression of the polypeptide of interest. Cells transformed with a vector that contains a selectable marker, such as production of fluorescent protein, may be positively selected for expression of the marker. In other embodiments, the cells containing a vector with a drug resistance gene may be positively selected for the ability to grow under selective conditions.

Kits

A kit is provided for inhibiting or reducing growth of cancer cells in a patient. Also provided are kits for identifying the presence of dysplastic cells in vitro or in vivo.

The kits described herein may comprise an antibody, antigen-binding fragments thereof, or an antibody composition described herein and instructions for using the kit in a method for inhibiting or reducing growth of tumor cells in the patient or in a method for identifying the presence of dysplastic cells, for example, in a biological sample. The kit may comprise at least one chemotherapeutic or cytotoxic reagent. The kit may comprise an antifolate compound. The kit may comprise at least one diagnostic reagent. An example of a diagnostic reagent is a detectable label, for example but not limited to a radioactive, fluorescent, or chromophoric agent (e.g., $^{111}$In-DOTA). The detectable label may comprise an enzyme. The kit may comprise instructions and a means for administering the antibody or antibody composition, for example, by injection.

Uses and Methods of Making BSA-Ganglioside Conjugates

Described herein are albumin-ganglioside conjugates and methods for producing such conjugates. To determine whether an antibody, or antigen-binding fragment, of interest is effective in mediating binding to a given antigen, one must characterize antibody binding. There are numerous ways to characterize antibody binding, such as dot-blot, western blot, immunoprecipitation assay, ELISA, FACS analysis/Flow cytometry, and immunofluorescence detection of bound antibody. While a variety of assays are available to test antibody binding, the particular assay used must be selected with an understanding of the antibody's purpose in mind. For example, if an antibody or antigen-binding fragment thereof is to be used in a clinical setting, it should be characterized by an assay that will present the antigen of interest in a form most likely to be found in vivo. In this instance, and in the case of a cell-surface protein, flow cytometry may be a useful assay because it allows the interaction of the antibody or antigen-binding fragment thereof to be assessed in the context of the native antigen.

One way to identify cells containing a vector that encodes an antigen-specific binding protein is using an Enzyme-Linked ImmunoSorbent Assay (ELISA) that makes use of the antigen of interest. There are two main approaches used to perform an ELISA: an indirect ELISA and a sandwich ELISA. To carry out an indirect ELISA, the antigen of interest is adsorbed or fixed to the surface of a microtiter plate and then the antibody or antigen-binding fragment thereof of interest is added to the microtiter plate to detect the antigen. Conversely, a sandwich ELISA makes use of an antibody known to be specific for the antigen of interest, in addition to the antibody being characterized. The known antibody is used to coat the microtiter plate, such that it will bind, or capture, the antigen of interest when it is added to the microtiter plate. Once the antigen of interest has been captured, the antibody or antigen-binding fragment thereof of interest is added to the microtiter plate to assess its binding characteristics for the antigen. In either case, bound antibody or antigen-binding fragment thereof is typically detected by an enzyme-conjugated secondary antibody that is specific for the antibody or antigen-binding fragment thereof of interest.

An ELISA useful for characterizing ganglioside-specific antibodies or antigen-binding fragments would be useful in determining the potential applications of such antibodies or antigen-binding fragments. The use of gangliosides as ELISA antigens is complicated, however, by the fact that free gangliosides are poorly immunogenic (Jacques et al., 4 Org. Biomol. Chem. 142-154 (2006)).

Ganglioside Conjugates

Disclosed herein are ganglioside-albumin conjugates that not only retain the antigenic properties of the conjugated ganglioside, but increase the stability of the ganglioside and allow better adherence to an ELISA microtiter plate. A ganglioside is conjugated to albumin through reductive amination of the ganglioside by primary amines in albumin in the presence of sodium cyanoborohydride. Conjugation proceeds through Schiff base formation to the reducing end(s) of the carbohydrate moiety on the ganglioside, followed by reduction with sodium cyanoborohydride. Accordingly, some embodiments described herein include a ganglioside conjugated to a carrier protein via a reducing end(s) of the carbohydrate moiety on the ganglioside. Some embodiments comprise a ganglioside conjugated to a carrier protein, wherein the carrier is BSA. In some embodiments, the ganglioside is GD2. In some embodiments, the ganglioside is GM3. In some embodiments, the ganglioside is GM2. In another embodiment, GD2 is conjugated to BSA. In some embodiments, the reductive amination of a ganglioside is catalyzed by sodium cyanoborohydride.

In some embodiments the ganglioside-albumin conjugate retains ganglioside antigenicity such that a ganglioside-specific monoclonal antibody or antigen-binding fragment thereof can bind the conjugate. In some embodiments the GD2-BSA conjugate retains GD2 antigenicity such that a GD2-specific monoclonal antibody or antigen-binding fragment thereof can bind the conjugate. In some embodiments the GM2-BSA conjugate retains GM2 antigenicity such that a GM2-specific monoclonal antibody or antigen-binding fragment thereof can bind the conjugate. In some embodiments the GM3-BSA conjugate retains GM3 antigenicity such that a GM3-specific monoclonal antibody or antigen-binding fragment thereof can bind the conjugate.

The albumin-ganglioside conjugates described herein may be used in an ELISA to characterize the specificity of an antibody or antigen-binding fragment thereof for a particular ganglioside. In one aspect, the albumin-ganglioside conjugates described provide an enhanced ability to adsorb the conjugated gangliosides to ELISA plates relative to unconjugated gangliosides. Once adsorbed, the conjugates may be used as ganglioside antigens in a direct ELISA to characterize binding aspects of ganglioside specific antibodies or antigen-binding fragments. In one embodiment, the albumin-ganglioside conjugate may be a BSA-GD2 conjugate. In one embodiment, the BSA-ganglioside conjugate may be a BSA-GM2 conjugate. In one embodiment, the BSA-ganglioside conjugate may be a BSA-GM3 conjugate. Other such gangliosides may be conjugated to BSA using the methods described and then used for the purposes described herein. Such conjugates and uses thereof are within the scope of this disclosure.

Embodiments of the protein conjugates include the following.

Embodiment A1 provides a protein conjugate comprising albumin and a ganglioside.

Embodiment A2 provides the conjugate of embodiment A1 wherein the albumin is bovine serum albumin.

Embodiment A3 provides the conjugate of embodiment A1, wherein the ganglioside is conjugated to albumin via a reducing end of the carbohydrate moiety on the ganglioside.

Embodiment A4 provides the conjugate of embodiment A3 wherein the albumin is bovine serum albumin.

Embodiment A5 provides the conjugate of embodiment A3 wherein the ganglioside is GD2.

Embodiment A6 provides the conjugate of embodiment A1 wherein the conjugate is immunoreactive with a GD2-specific antibody.

Embodiment A7 provides the conjugate of embodiment A1, wherein the ganglioside is GM2.

Embodiment A8 provides the conjugate of embodiment A7, wherein the conjugate is immunoreactive with a GM2-specific antibody.

Embodiment A9 provides the conjugate of embodiment A1, wherein the ganglioside is GM3.

Embodiment A10 provides the conjugate of embodiment A9, wherein the conjugate is immunoreactive with a GM3-specific antibody.

Embodiment A11 provides a method of conjugating a ganglioside to albumin, the method comprising reductively aminating a reducing end of a carbohydrate moiety on the ganglioside.

Embodiment A12 provides the method of embodiment A11, wherein the albumin is bovine serum albumin.

Embodiment A13 provides the method of embodiment A11, wherein the reductive amination is catalyzed by sodium cyanoborohydride.

Embodiment A14 provides the method of embodiment A13, wherein the ganglioside is GD2.

Embodiment A15 provides the method of embodiment A13, wherein the ganglioside is GM2.

Embodiment A16 provides the method of embodiment A13, wherein the ganglioside is GM3.

Cell Culture Compositions and Methods

Described herein are compositions and methods for culturing eukaryotic cells. The cells may be any type of eukaryotic cell, but, in one embodiment, are preferably of mammalian origin. In some embodiments, the cells are Chinese Hamster ovary (CHO) cells. In some embodiments, the eukaryotic cells are genetically modified to produce IgM antibodies or antigen-binding fragments. The eukaryotic cells may be clinical isolates, transformed with foreign DNA or RNA, immortalized, virus-infected, or modified by other generally known biological or chemical means. The eukaryotic cells may be grown in monolayers or in suspended culture, which may occur in a cell culture incubator, bioreactor, shake-flask, or other similar tissue culture device. In addition, the eukaryotic cells can be cultured at a temperature above 32° C. and below 50° C., in between 2% to 8% $CO_2$, with or without shaking. In one embodiment, the cells can be cultured at a temperature of 37° C., in 5% $CO_2$, with shaking at 120 rpm. The eukaryotic cells can be cultured in tissue culture media, such as GIBCO-CD-CHO complete medium (1 L GIBCO-CD-CHO medium+25 μM MSX) or similar complete medium, in combination with the compositions and methods disclosed herein. The cultured eukaryotic cells may be engineered to produce a foreign protein, which the compositions and methods described herein can, but need not necessarily, enhance.

Disclosed herein are compositions suitable for use with eukaryotic cell culture media. The composition includes, but is not limited to, various essential and nonessential amino acids, for example, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; sugars, for example, glucose, fructose, mannose, and galactose; and vitamins, such as folic acid, vitamin B-12, vitamin D, and riboflavin that may influence growth characteristics of cultured eukaryotic cells. In embodiment B1, the composition includes glucose, glutamate, aspartate, serine, histidine, threonine, arginine, tyrosine, cysteine, valine, methionine, tryptophan, phenylalanine, isoleucine, leucine, lysine, proline, nicotinic acid amide, pyridoxine HCl, folic acid, vitamin B-12, riboflavin, and thiamine HCl.

In embodiment B2, the composition comprises the cell culture of embodiment B1, wherein the concentration of glucose is 50 g/L, the concentration of glutamate is from 2.5 to 3.75 g/L, the concentration of aspartate is from 1.5 to 2.0 g/L, the concentration of serine is from 0.3 to 0.5 g/L, the concentration of histidine is from 1.1 to 1.5 g/L, the concentration of threonine is from 2.0 to 3.0 g/L, the concentration of arginine is from 1.0 to 1.5 g/L, the concentration of tyrosine is from 1.8 to 2.2 g/L, the concentration of cysteine is from 0.9 to 1.1 g/L, the concentration of valine is from 1.0 to 3.0, the concentration of methionine is from 0.8 to 1.2 g/L, the concentration of Tryptophan is from 0.5 to 0.8 g/L, the concentration of phenyalanine 1.3 to 1.7 g/L, the concentration of isoleucine is from 0.8 to 2.4 g/L, the concentration of leucine is from 1.5 to 4.5 g/L, the concentration of lysine is from 3.5 to 5.0 g/L, the concentration of proline is from 0.5 to 0.7 g/L, the concentration of nicotinic acid amide is from 30 to 40 mg/L, the concentration of pyridoxine HCl is from 200 to 250 mg/L, the concentration of folic acid 100 to 130 mg/L, the concentration of vitamin B-12 20 to 40 mg/L, the concentration of riboflavin is from 20 to 40 mg/L, and the concentration of thiamine HCl is from 100 to 150 mg/L.

Also disclosed herein are methods for culturing eukaryotic cells in which a composition described in the preceding paragraph may be used to enhance the viability of eukaryotic cells. For example, the compositions may be added to cultured CHO cells and to cultured IgM-producing eukaryotic (e.g., CHO) cells. The composition may be used to enhance the viability of eukaryotic tissue culture cells by adding the composition to growth media, as a media supplement, either before or after growth media is applied to eukaryotic cells. Alternatively, growth media components may be added to the composition to produce a growth media that contains the composition.

Embodiment B3 provides a method of culturing eukaryotic cells comprising adding to the cells a primary tissue culture media and then supplementing the primary tissue culture media with a cell culture composition comprising, glucose, glutamate, aspartate, serine, histidine, threonine, arginine, tyrosine, cysteine, valine, methionine, tryptophan, phenylalanine, isoleucine, leucine, lysine, proline, nicotinic acid amide, pyridoxine HCl, folic acid, vitamin B-12, riboflavin, and thiamine HCl.

Embodiment B4 provides the method of embodiment B3 wherein the volume of the cell culture composition that is added to the primary tissue culture media is between 1.0% and 20% of the volume of the primary tissue culture media.

Embodiment B5 provides the method of embodiment B3, wherein the cell culture composition is not added to the primary tissue culture media before the third day following addition of the primary tissue culture media.

Embodiment B6 provides the method of embodiment B3, wherein the eukaryotic cells have been transformed to produce one or more proteins.

Embodiment B7 provides the method of embodiment B6, wherein the one or more proteins is an antibody, or an antigen-binding fragment thereof.

Embodiment B8 provides the method of embodiment B7 wherein the antibody is an IgM.

Embodiment B9 provides the method of embodiment B3, wherein the cell culture composition is added to the primary tissue culture media on consecutive days.

In another embodiment, the composition may be used to increase the amount of protein produced by a eukaryotic cell that is genetically modified to produce a recombinant protein. For example, the composition may be added to cultured cells engineered to express a recombinant human antibody or antigen-binding fragment thereof (e.g., cells modified to express IgM and more specifically CHO cells modified to express IgM). The composition may be used to increase recombinant protein expression by adding the composition to growth media, as a media supplement, either before or after growth media is applied to eukaryotic cells. Alternatively, growth media components may be added to the composition to produce a growth media that contains the composition.

The composition may be used as growth media or as a supplement for growth media. As a supplement the composition may be added to cell culture media either before or after the culture media is added to tissue culture containers. The composition described herein may be used to supplement eukaryotic cell culture media to a total concentration of 1.5% to 2.5%. These same concentrations may be used to produce cell culture media already containing the composition.

Also featured are methods for increasing the amount of protein produced by a eukaryotic cell that is genetically modified to produce a recombinant protein by adding valeric acid to cell culture media. For example, the valeric acid may be added to media for cultured CHO, hybridoma, and NSO cells engineered to express a recombinant human antibody or antigen-binding fragment. In one embodiment, valeric acid may be added to cell culture media to a final concentration from 0.1 mM to 10 mM. In one embodiment, valeric acid may be added at specific points in the cell growth period, for example, valeric acid may be added to the culture media on specific days following revival of cell stocks or after cell cultures are split.

Embodiment B10 provides a method of enhancing protein production by cells, comprising supplementing the growth media of the cells with valeric acid.

Embodiment B11 provides the method of embodiment B10, wherein the cells are antibody-producing cells.

Embodiment B12 provides the method of embodiment B10, wherein the growth media is supplemented to have a concentration of valeric acid from 0.1 mM to 10 mM.

Antibody Isolation or Purification

The antibodies or antigen-binding fragments described herein can be separated from a substantial portion of the cellular growth media from which they are recovered to allow for a more purified or isolated form of the antibody or antigen-binding fragment. Described herein are methods to purify or isolate antibodies or antigen-binding fragments, such as human IgM antibodies or antigen-binding fragments, from a solution, e.g., conditioned culture supernatant (CCS). Increasing the purity of a solution containing the antibodies or antigen-binding fragments may be accomplished in a number of ways, including, but not limited to, dialysis, size exclusion chromatography, centrifugation, ion-exchange chromatography, gradient centrifugation, filtration with a size-exclusion filter, affinity chromatography, immunoaffinity chromatography, and high performance liquid chromatography. The described antibodies or antigen-binding fragments may also be modified, genetically or chemically, to include an affinity tag, such as polyhistidine, that may be used to increase antibody or antigen-binding fragment thereof purity through affinity purification techniques.

Accordingly, some embodiments include an antibody or antigen-binding fragment thereof that is separated from a solution by affinity chromatography. Some embodiments comprise an antibody or antigen-binding fragment thereof that is substantially separated from a solution by affinity chromatography, wherein affinity for the antibody or antigen-binding fragment thereof is mediated by protein A. Some embodiments comprise an antibody or antigen-binding fragment thereof that is substantially separated from a solution by ion-exchange chromatography. Some embodiments comprise an antibody or antigen-binding fragment thereof that is substantially separated from a solution by cation-exchange chromatography, wherein the cation-exchange chromatography column comprises an acrylamide-dextran copolymer resin. Some embodiments comprise an antibody or antigen-binding fragment thereof that is substantially separated from a solution by hydroxyapatite chromatography. Some embodiments comprise an antibody or antigen-binding fragment thereof that is substantially separated from a solution by hydroxyapatite chromatography, wherein the hydroxyapatite chromatography column incorporates a ceramic calcium phosphate resin.

The process by which the described antibodies or antigen-binding fragments can be purified or isolated may vary as the requirements for the resulting antibody or antigen-binding fragment thereof may differ depending on the application for which the antibodies or antigen-binding fragments will be used. For example, antibodies or antigen-binding fragments for use in a pharmaceutical composition would require stringent purification, while antibodies or antigen-binding fragments for use in an in vitro diagnostic assay can be purified to a lesser degree. Accordingly some embodiments include contacting an antibody or antigen-binding fragment-containing sample with a protein A matrix. Some embodiments include contacting an antibody or antigen-binding fragment-containing sample with an ion-exchange matrix. In one embodiment, the ion-exchange matrix can be a cation-exchange chromatography matrix. In a more preferable embodiment the cation-exchange chromatography matrix can include acrylamide-dextran copolymer resin. Some embodiments include contacting an antibody or antigen-binding fragment-containing sample with an hydroxyapatite matrix. In one embodiment, the hydroxyapatite matrix can include a calcium phosphate resin.

Serial affinity chromatography is a process that yields an isolated or purified protein. The process may employ two or more rounds of differing affinity chromatography techniques to produce a purified or isolated protein of interest (Friedrichs and Grose, 49 J. Virol. 992 (1984)). Accordingly, in some embodiments an antibody or antigen-binding fragment-containing sample may be contacted with a protein A matrix under conditions that promote binding of antibodies or antigen-binding fragments to the matrix; the matrix may be washed to remove unbound proteins; the material bound by the protein A matrix may be eluted; the eluted material may be contacted by a cation-exchange chromatography matrix under conditions that promote binding of antibodies or antigen-binding fragments to the matrix; the matrix may be washed to remove unbound proteins; the material bound by the cation-exchange chromatography matrix may be eluted; the eluted material may be contacted by a hydroxyapatite resin under conditions that promote binding of antibodies or antigen-binding fragments to the matrix; the matrix may be washed to remove unbound proteins; and the bound material may be eluted. In addition, optional steps may be added to various points in this process to allow for more stringent purification of the antibody or antigen-binding fragment thereof. For example, the antibody or antigen-binding fragment-containing solution may be supplemented with detergent, such as Triton®-X 100 or Tween® 80, to inactivate microbes, such as bacteria, viruses, and parasites.

Affinity-based chromatography of proteins is a multi-step process that generally involves equilibrating a chromatography column, contacting a sample solution with the matrix of a column, washing away the unbound material in the column, and eluting the desired material. This general process may be repeated one or more times, under varying conditions, to increase the purity of a sample, as needed. In some embodiments a protein A matrix may be used to contact the sample to be purified. In one embodiment, the protein A matrix may be porous, having pores ranging from 1000 to 5000 angstroms in diameter. In another embodiment the protein A matrix has pores with an average diameter of 3000 angstroms.

In some embodiments the affinity matrix is washed and equilibrated before use. For example, the affinity matrix may be washed with purified water to remove any contaminants In some embodiments the affinity matrix may be washed with 3 to 10 column volumes of purified water. In another embodiment the affinity matrix may be washed with 5 column volumes of purified water. In some embodiments the affinity matrix may be washed with at least one acidic buffer. For example, the affinity matrix may be washed with 1 to 5 column volumes of 20 mM HCl at pH 1.5. In another embodiment the affinity matrix is washed with 3 column volumes of 20 mM HCl at pH 1.5.

In addition, the affinity matrix may be washed with at least one additional buffer, such as 6 M guanidine.HCl. Before contacting the affinity matrix with a sample the matrix may be equilibrated with a mildly basic or neutral pH buffer. In one embodiment, the affinity matrix may be equilibrated with 2 to 8 column volumes of a buffer at pH 7.5. In another embodiment the affinity matrix may be equilibrated with 5 column volumes of a 10 mM sodium phosphate buffer containing 200 mM NaCl and 0.01% Tween®-80, at pH 7.5. Sodium phosphate buffers described herein may be prepared from a mixture of monobasic and dibasic sodium phosphate. Mixed in the correct ratios, these solutions may yield phosphate buffers within the range of pH 4 to pH 10.

Samples to be purified or isolated via contacting the affinity matrix should be substantially free of large particulate matter. Such particulate matter may be removed in a variety of ways, such as by centrifugation or filtration. In another embodiment the conditioned culture supernatant (CCS) described herein is made substantially free of large particulate matter before contact with an affinity matrix. In yet another embodiment the CCS is filtered to remove particulate matter. A filter with an appropriate pore size may be used, such as a filter having pores with an average diameter of 1 μm or a filter having pores with an average diameter of 0.75 μm or a filter having pores with an average diameter of 0.5 μm or a filter having pores with an average diameter of 0.22 μm, or a filter having pores with an average diameter of 0.1 μm.

Before contacting the affinity matrix with a solution containing a sample to be purified or isolated, the solution may be treated with detergent to inactivate at least one microbial contaminant, such as bacteria, viruses, and parasites. In one embodiment, the CCS is supplemented with detergent to inactivate at least one microbial contaminant. In one embodiment, the detergent is Triton® X-100. The concentration of detergent added to the solution containing a sample to be purified or isolated may vary to meet the needs of a particular purification scheme. In one embodiment, the solution containing a sample to be purified or isolated may have 10% detergent. In another embodiment, the solution containing a sample to be purified or isolated may have 7% detergent. In one embodiment, the solution containing a sample to be purified or isolated may have 5% detergent. In one embodiment, the solution containing a sample to be purified or isolated may have 3% detergent. In one embodiment, the solution containing a sample to be purified or isolated may have 2% detergent. In one embodiment, the solution containing a sample to be purified or isolated may have 1% detergent. In one embodiment, the solution containing a sample to be purified or isolated may have 0.5% detergent. In one embodiment, the solution containing a sample to be purified or isolated may have 0.1% detergent.

Once applied to the affinity matrix, the sample may be processed at a desired flow rate, for example, to facilitate processing or binding of the sample. While any flow rate may be used, common flow rates are between 1 and 200 cm/h. In some embodiments the flow rate of the sample may be 1 cm/h. In other embodiments the flow rate of the sample may be 10 cm/h. In one embodiment, the flow rate of the sample may be 25 cm/h. In one embodiment, the flow rate of the sample may be 50 cm/h. In another embodiment the flow rate of the sample may be 76 cm/h. In another embodiment the flow rate of the sample may be 100 cm/h. In some embodiments the flow rate of the sample may be 125 cm/h. In another embodiment the flow rate of the sample may be 150 cm/h. In one embodiment, the flow rate of the sample may be 175 cm/h. In one embodiment, the flow rate of the sample may be 200 cm/h.

After the affinity matrix has been contacted by the sample material, unbound sample material may be removed by washing with a buffer. In one embodiment, the affinity matrix may be washed with a buffer with an acidic pH. In one embodiment, the affinity matrix may be washed with a buffer with a neutral pH. In one embodiment, the affinity matrix may be washed with a buffer with a basic pH. In another embodiment the affinity matrix may be washed with 5 to 15 column volumes of a 10 mM sodium phosphate buffer containing 200 mM NaCl and 0.01% Tween®-80, at pH 7.5.

After unbound proteins have been removed from the affinity matrix by washing, proteins bound to the affinity matrix may be eluted by washing the affinity matrix with an elution buffer. The elution buffer should be selected carefully to assure that it will disrupt the interaction between the protein of interest, e.g., a human IgM antibody, and the matrix, but will not denature or otherwise deteriorate the condition of the protein of interest. In one embodiment, the affinity matrix may be washed with a buffer with an acidic pH to elute the protein of interest. In one embodiment, the affinity matrix may be washed with a buffer with a neutral pH to elute the protein of interest. In one embodiment, the affinity matrix may be washed with a buffer with a basic pH to elute the protein of interest. Some embodiments include a buffer having sodium phosphate and magnesium chloride for eluting material bound to a chromatography column, where up to 10 column volumes of this buffer are used to elute bound material from the column. In some embodiments, a buffer having between 5 and 10 mM sodium phosphate and 1 and 5 M magnesium chloride may be used for eluting material bound to an affinity matrix. Another embodiment, includes 3 column volumes of a buffer comprising 5 mM sodium phosphate and 3 M magnesium chloride to elute material bound to an affinity matrix. In some embodiments IgM may be eluted from a protein A matrix using a 5 mM sodium phosphate buffer supplemented with 3 M $MgCl_2$ at pH 6.8.

Disclosed herein are methods for purifying or isolating proteins, e.g., IgM antibodies or antigen-binding fragments, using ion-exchange chromatography. Ion-exchange chromatography of proteins is a multi-step process that generally involves equilibrating a chromatography column, contacting a sample solution with the matrix of a column, washing away the unbound material in the column, and eluting the desired material. This general process may be repeated one or more times, under varying conditions, to increase the purity of a sample, as needed. In some embodiments the cation exchange chromatography matrix may be an acrylamide-dextran copolymer resin. In one embodiment, the cation exchange chromatography matrix may be MacroCap™ SP resin.

In some embodiments the ion-exchange matrix is washed and equilibrated before use. For example, the ion-exchange matrix may be washed with purified water to remove any contaminants. In one embodiment, the ion-exchange matrix may be washed with 1 to 10 column volumes of purified water. In one embodiment, the ion-exchange matrix may be washed with 2 column volumes of purified water. In some embodiments the ion-exchange matrix may be washed with at least one buffer. For example, the ion-exchange matrix may be washed with 1 to 5 column volumes of a buffer having 0.5 M NaOH. In another embodiment the ion-exchange matrix is washed with 3 column volumes of a buffer having 0.5 M NaOH. In some embodiments the ion-exchange matrix is washed with 3 column volumes of a buffer having 2 M NaCl. Before contacting the ion-exchange matrix with a sample the matrix may be equilibrated with an acidic, basic, or neutral pH buffer. In one embodiment, the ion-exchange matrix may be equilibrated with 2 to 8 column volumes of a buffer at pH 6.8. In one embodiment, the ion-exchange matrix may be equilibrated with 5 column volumes of a 10 mM sodium phosphate buffer, containing 75 mM NaCl and 0.01% Tween®-80, at pH 6.8.

Samples to be purified or isolated via contacting the ion-exchange matrix should be substantially free of large particulate matter. Such particulate matter may be removed in a variety of ways, such as by centrifugation or filtration. In some embodiments the conditioned culture supernatant (CCS) described herein is made substantially free of large particulate matter before having contact with an ion-exchange matrix. In another embodiment the CCS is filtered to remove particulate matter. A filter with any pore size may be used, such as a filter having pores with an average diameter of 1 μm or a filter having pores with an average diameter of 0.75 μm or a filter having pores with an average diameter of 0.5 μm or a filter having pores with an average diameter of 0.22 μm, or a filter having pores with an average diameter of 0.1 μm.

Before contacting the ion-exchange matrix with a solution containing a sample to be purified, the solution may be treated with detergent to inactivate at least one microbial contaminant, such as bacteria, viruses, and parasites, or to help maintain the target protein in a soluble state. In some embodiments the sample may be supplemented with detergent to inactivate at least one microbial contaminant or to help maintain the target protein in a soluble state. In one embodiment, the detergent is Triton® X-100. In one embodiment, the detergent is Tween®-80. The concentration of detergent added to the solution containing a sample to be purified or isolated may vary to meet the needs of a particular purification scheme. In one embodiment, the solution containing a sample to be purified or isolated may have 10% detergent. In one embodiment, the solution containing a sample to be purified or isolated may have 7% detergent. In one embodiment, the solution containing a sample to be purified or isolated may have 5% detergent. In one embodiment, the solution containing a sample to be purified or isolated may have 3% detergent. In one embodiment, the solution containing a sample to be purified or isolated may have 2% detergent. In one embodiment, the solution containing a sample to be purified or isolated may have 1% detergent. In one embodiment, the solution containing a sample to be purified or isolated may have 0.5% detergent. In one embodiment, the solution containing a sample to be purified or isolated may have 0.1% detergent.

Once applied to the ion-exchange matrix, the sample may be processed at a desired flow rate, for example, to facilitate processing or binding of the sample. While any flow rate may be used, common flow rates are between 1 and 200 cm/h. In one embodiment, the flow rate of the sample may be 1 cm/h. In one embodiment, the flow rate of the sample may be 10 cm/h. In one embodiment, the flow rate of the sample may be 25 cm/h. In one embodiment, the flow rate of the sample may be 50 cm/h. In one embodiment, the flow rate of the sample may be 76 cm/h. In one embodiment, the flow rate of the sample may be 100 cm/h. In one embodiment, the flow rate of the sample may be 125 cm/h. In one embodiment, the flow rate of the sample may be 150 cm/h. In one embodiment, the flow rate of the sample may be 175 cm/h. In another embodiment the flow rate of the sample may be 200 cm/h.

After the ion-exchange matrix has been contacted by the sample material, unbound sample material may be removed by washing with a buffer. In one embodiment, the ion-exchange matrix may be washed with a buffer with an acidic pH. In one embodiment, the ion-exchange matrix may be washed with a buffer with a neutral pH. In one embodiment, the ion-exchange matrix may be washed with a buffer with a basic pH. In one embodiment, the ion-exchange matrix may be washed with 5 to 15 column volumes of a buffer containing 10 mM sodium phosphate, 75 mM NaCl, and 0.01% Tween®-80, at pH 6.8.

After unbound proteins have been removed from the ion-exchange matrix by washing, proteins bound to the ion-exchange matrix may be eluted by washing the ion-exchange matrix with an elution buffer. The elution buffer should be selected carefully to assure that it will disrupt the interaction between the protein of interest, e.g., a human IgM antibody, and the matrix, but will not denature or otherwise deteriorate the condition of the protein of interest. In one embodiment, the ion-exchange matrix may be washed with a buffer with an acidic pH to elute the protein of interest. In one embodiment, the ion-exchange matrix may be washed with a buffer with a neutral pH to elute the protein of interest. In one embodiment, the ion-exchange matrix may be washed with a buffer with a basic pH to elute the protein of interest. Some embodiments include a buffer having sodium phosphate and sodium chloride for eluting material bound to a chromatography column, where up to 10 column volumes of this buffer are used to elute bound material from the column. In some embodiments, a buffer having between 5 and 50 mM sodium phosphate and 150 and 500M sodium chloride may be used for eluting material bound to an ion-exchange matrix. Another embodiment includes 4 column volumes of a buffer comprising 10 mM sodium phosphate buffer containing 200 mM NaCl to elute material bound to an ion-exchange matrix. In some embodiments IgM may be eluted from a MacroCap™ SP matrix using a 10 mM sodium phosphate buffer containing 200 mM NaCl and 0.01% Tween0-80, at pH 6.8.

Disclosed herein are methods for purifying or isolating proteins, e.g., IgM antibodies or antigen-binding fragments, using hydroxyapatite chromatography. Hydroxyapatite chromatography of proteins is a multi-step process that generally involves equilibrating a chromatography column, contacting a sample solution with the matrix of a column, washing away the unbound material in the column, and eluting the desired material. This general process may be repeated one or more times, under varying conditions, to increase the purity of a sample, as needed. In some embodiments the hydroxyapatite chromatography matrix may be a calcium phosphate matrix. In one embodiment, the hydroxyapatite chromatography matrix may be CHT® II Ceramic Hydroxyapatite, 80 μm bead size.

In some embodiments the hydroxyapatite matrix is hydrated before use. In one embodiment, the hydroxyapatite matrix is hydrated with a solution having 200 mM potassium phosphate, at pH 9.0, using 0.54 g of dry matrix for each mL of desired column-bed volume. Before contacting the hydroxyapatite matrix with a sample the matrix may be equilibrated with an acidic, basic, or neutral pH buffer. In one embodiment, the hydroxyapatite matrix may be equilibrated with 2 to 8 column volumes of a buffer at pH 6.8. In another embodiment the hydroxyapatite matrix may be equilibrated with 5 column volumes of a buffer containing 10 mM sodium phosphate, 100 mM NaCl, and 0.01% Tween®-80, at pH 6.8.

Samples to be purified or isolated via contacting the hydroxyapatite matrix should be substantially free of large particulate matter. Such particulate matter may be removed in a variety of ways, such as by centrifugation or filtration. In one embodiment, the conditioned culture supernatant (CCS) is made substantially free of large particulate matter before having contact with a hydroxyapatite matrix. In one embodiment, the CCS is filtered to remove particulate matter. A filter with any pore size may be used, such as a filter having pores with an average diameter of 1 μm or a filter having pores with an average diameter of 0.75 μm or a filter having pores with an average diameter of 0.5 μm or a filter having pores with an average diameter of 0.22 μm, or a filter having pores with an average diameter of 0.1 μm.

Before contacting the hydroxyapatite matrix with a solution containing a sample to be purified, the solution may be treated with detergent to inactivate at least one microbial contaminant, such as bacteria, viruses, and parasites, or to help maintain the target protein in a soluble state. In some embodiments the sample may be supplemented with detergent to inactivate at least one microbial contaminant or to help maintain the target protein in a soluble state. In one embodiment, the detergent is Triton® X-100. In one embodiment, the detergent is Tween®-80. The concentration of detergent added to the solution containing a sample to be purified or isolated may vary to meet the needs of a particular purification scheme. In one embodiment, the solution containing a sample to be purified or isolated may have 10% detergent. In one embodiment, the solution containing a sample to be purified or isolated may have 7% detergent. In one embodiment, the solution containing a sample to be purified or isolated may have 5% detergent. In one embodiment, the solution containing a sample to be purified or isolated may have 3% detergent. In one embodiment, the solution containing a sample to be purified or isolated may have 2% detergent. In one embodiment, the solution containing a sample to be purified or isolated may have 1% detergent. In one embodiment, the solution containing a sample to be purified or isolated may have 0.5% detergent. In one embodiment, the solution containing a sample to be purified or isolated may have 0.1% detergent.

Once applied to the hydroxyapatite matrix, the sample may be processed at a desired flow rate, for example, to facilitate processing or binding of the sample. While any flow rate may be used, common flow rates are between 1 and 200 cm/h. In one embodiment, the flow rate of the sample may be 1 cm/h. In one embodiment, the flow rate of the sample may be 10 cm/h. In one embodiment, the flow rate of the sample may be 25 cm/h. In one embodiment, the flow rate of the sample may be 50 cm/h. In one embodiment, the flow rate of the sample may be 76 cm/h. In one embodiment, the flow rate of the sample may be 100 cm/h. In one embodiment, the flow rate of the sample may be 125 cm/h. In one embodiment, the flow rate of the sample may be 150 cm/h. In one embodiment, the flow rate of the sample may be 175 cm/h. In one embodiment, the flow rate of the sample may be 200 cm/h.

After the hydroxyapatite matrix has been contacted by the sample material, unbound sample material may be removed by washing with a buffer. In one embodiment, the hydroxyapatite matrix may be washed with a buffer with an acidic pH. In one embodiment, the hydroxyapatite matrix may be washed with a buffer with a neutral pH. In one embodiment, the hydroxyapatite matrix may be washed with a buffer with a basic pH. In one embodiment, the hydroxyapatite matrix may be washed with 5 to 15 column volumes of a buffer containing 10 mM sodium phosphate, 100 mM NaCl, and 0.01% Tween®-80, at pH 6.8.

After unbound proteins have been removed from the hydroxyapatite matrix by washing, proteins bound to the hydroxyapatite matrix may be eluted by washing the hydroxyapatite matrix with an elution buffer. The elution buffer should be selected carefully to assure that it will disrupt the interaction between the protein of interest, e.g., a human IgM antibody, and the matrix, but will not denature or otherwise deteriorate the condition of the protein of interest. In one embodiment, the hydroxyapatite matrix may be washed with a buffer with an acidic pH to elute the protein of interest. In one embodiment, the hydroxyapatite matrix may be washed with a buffer with a neutral pH to elute the protein of interest. In one embodiment, the hydroxyapatite matrix may be washed with a buffer with a basic pH to elute the protein of interest. Some embodiments include a buffer having sodium phosphate and sodium chloride for eluting material bound to a hydroxyapatite column, where up to 10 column volumes of this buffer are used to elute bound material from the column. In some embodiments, a buffer having between 150 and 500 mM sodium phosphate and 50 and 200 M sodium chloride may be used for eluting material bound to a hydroxyapatite matrix. In one embodiment, 4 column volumes of a buffer comprising 175 mM sodium phosphate buffer containing 100 mM NaCl may be used to elute material bound to an hydroxyapatite matrix. In another embodiment IgM may be eluted from a CHT® II Ceramic Hydroxyapatite matrix using a buffer containing 175 mM sodium phosphate, 100 mM NaCl, and 0.01% Tween®-80, at pH 6.8.

Buffers of varying composition, with respect to salts used, salt concentration, detergents used, detergent concentration, pH, and the like, may be used to substantially perform the methods described herein. Accordingly, such variations are contemplated to be within the scope of the disclosure provided, which is not intended to be exclusive or limiting.

Embodiment C1 provides a method of purifying or isolating a protein, the method comprising applying a solution comprising the protein to an affinity chromatography column, applying eluate from the affinity chromatography column to a cation exchange chromatography column, and applying eluate from the cation exchange chromatography column to a hydroxyapatite chromatography column, and obtaining the eluate from the hydroxyapatite chromatography column.

Embodiment C2 provides the method of embodiment C1, wherein the affinity chromatography column comprises at least one substrate coated with protein A.

Embodiment C3 provides the method of embodiment C2, wherein the at least one substrate coated with protein A is porous.

Embodiment C4 provides the method of embodiment C3, wherein the porous substrate comprises pores of 3000 angstroms.

Embodiment C5 provides the method of embodiment C1, wherein the at least one substance coated with protein A binds a protein.

Embodiment C6 provides the method of embodiment C5, wherein the protein bound by at least one substance coated with protein A is eluted with a solution comprising magnesium chloride.

Embodiment C7 provides the method of embodiment C6, wherein the solution comprising magnesium chloride is a solution of 1M to 5M magnesium chloride.

Embodiment C8 provides the method of embodiment C6, wherein the solution comprising magnesium chloride is a solution of 3M magnesium chloride.

Embodiment C9 provides the method of embodiment C5, wherein the protein bound by the at least one substance coated with protein A is an antibody.

Embodiment C10 provides the method of embodiment C9, wherein the antibody is IgM.

Embodiment C11 provides the method of embodiment C1, wherein the cation exchange chromatography column comprises an acrylamide-dextran copolymer resin.

Embodiment C12 provides the method of embodiment C11, wherein the acrylamide-dextran copolymer resin binds a protein.

Embodiment C13 provides the method of embodiment C12, wherein the protein bound by the acrylamide-dextran copolymer resin is eluted with a solution comprising 10 mM sodium phosphate, 200 mM sodium chloride, and 0.01% polysorbate 80.

Embodiment C14 provides the method of embodiment C13, wherein the protein bound by the acrylamide-dextran copolymer resin is an antibody.

Embodiment C15 provides the method of embodiment C14, wherein the antibody is IgM.

Embodiment C16 provides the method of embodiment C1, wherein the hydroxyapatite chromatography column comprises a calcium phosphate resin.

Embodiment C17 provides the method of embodiment C16, wherein the calcium phosphate resin binds a protein.

Embodiment C18 provides the method of embodiment C17, wherein the protein bound by the calcium phosphate resin is eluted with a solution comprising 175 mM sodium phosphate, 100 mM sodium chloride, and 0.01% polysorbate 80.

Embodiment C19 provides the method of embodiment C18, wherein the protein bound by the calcium phosphate resin is an antibody.

Embodiment C20 provides the method of embodiment C19, wherein the antibody is IgM.

Embodiment C21 provides a method of purifying or isolating a protein, comprising
  a. applying a solution containing the protein to an affinity chromatography column comprising at least one substrate coated with protein A, and eluting any proteins bound by the at least one substance coated with protein A with a solution comprising 3M magnesium chloride;
  b. applying the eluate from the affinity chromatography column to a cation exchange chromatography column comprising an acrylamide-dextran copolymer resin, and eluting any proteins bound by the acrylamide-dextran copolymer resin with a solution comprising 10 mM sodium phosphate, 200 mM sodium chloride, and 0.01% polysorbate 80;
  c. applying the eluate from the cation exchange chromatography column to a hydroxyapatite comprising a calcium phosphate resin, and eluting any proteins bound by the calcium phosphate resin with a solution comprising 175 mM sodium phosphate, 100 mM sodium chloride, and 0.01% polysorbate 80.

The following examples are provided to describe the embodiments described herein with greater detail. They are intended to illustrate, not to limit, the embodiments.

EXAMPLE 1

GD-2 Specificity of CV-3-Derived IgM

A pool of human lymphoblast cells transformed with Epstein-Barr Virus (HLP) (Cahan, et al.) was tested for the ability to produce GD2-specific IgM antibodies. The cells were cultured in RMPI complete media (10% heat-inactivated FBS, 1% L-Glu, 1% antibiotics (Sigma)). Spent growth media was collected at passages two through four and assayed for IgM concentration and reactivity with GD2. The HLP produced 6-8 µg/mL IgM, (quantified by ELISA), after a culture of $2\text{-}5 \times 10^5$ cells/mL was grown for 3 days.

Figure 1B:
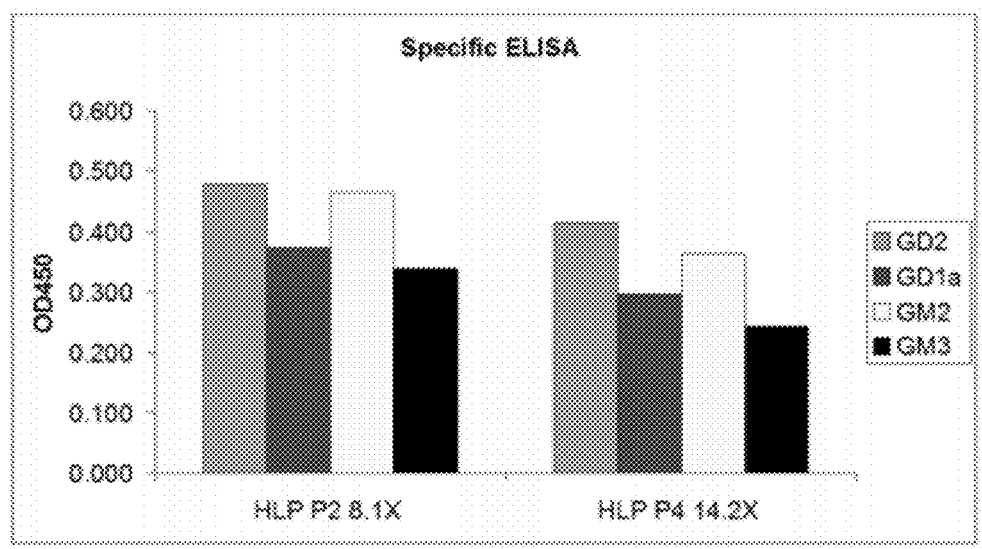
FIG. 1B demonstrates that cell culture supernatants from the HLP contain IgM antibodies that bind gangliosides GD1a, GD2, GM2, and GM3.

To determine whether the IgM produced by the HLP was specific for GD2, spent media from each culture was analyzed by ELISA. Briefly, gangliosides were coated to ELISA plates by evaporating 200 µl of ethanol containing 25 ng of GD2, GD1a, GM2 or GM3. Plates were then blocked and binding of IgM-containing cell culture media or human IgM were assessed according to regular ELISA procedures. Spent media from the HLP (concentrated either 8.1-fold or 14.2-fold) contained GD2-reactive IgM (FIG. 1A); however, the antibodies also recognized gangliosides GD1a, GM2, and GM3 (FIG. 1B). These data indicate that IgM produced by the HLP is polyreactive.

Figure 2:
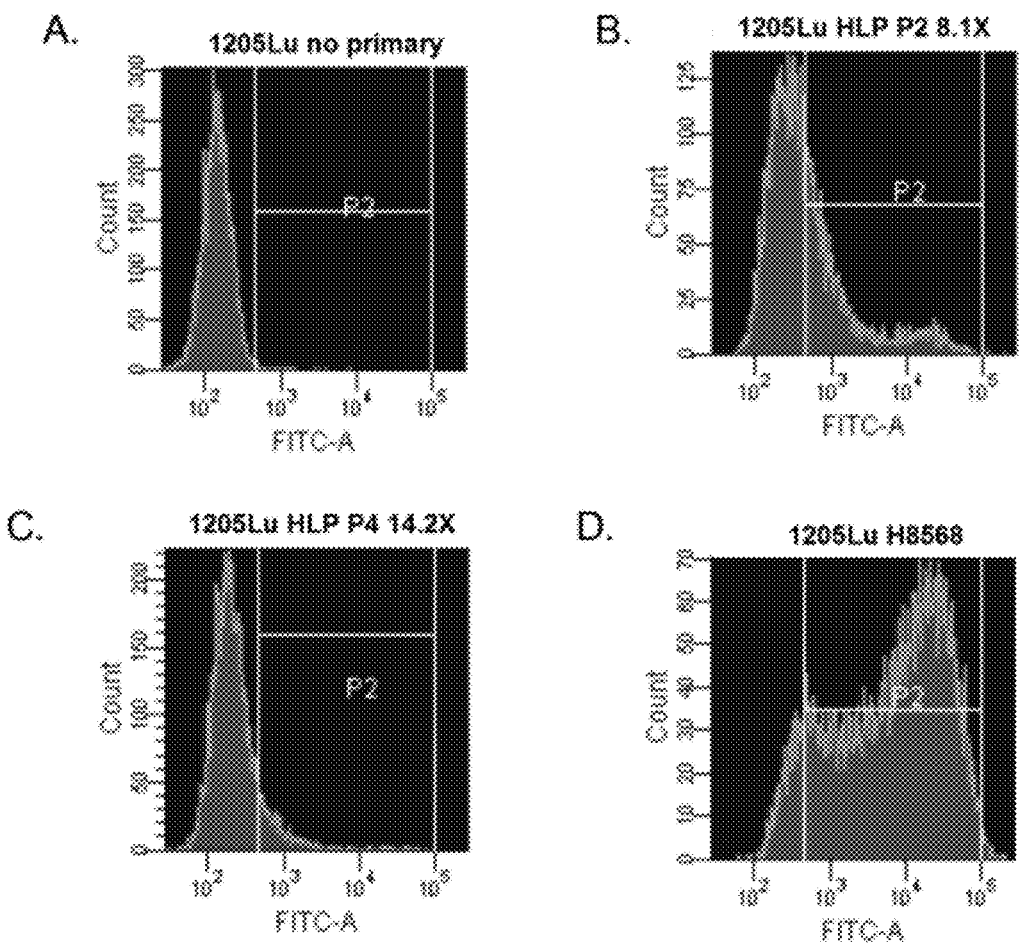
FIG. 2 shows binding levels of IgM antibodies produced by the HLP cell cultures on GD2-expressing 1205LU melanoma cells, as analyzed by fluorescence activated cell sorting (FACS).

FACS analysis was conducted to determine whether IgM produced by the HLP could bind GD2 expressed on the surface of melanoma cells. Briefly, 1205LU cells, a human melanoma cell line that expresses GD2 on its surface, were incubated with spent media from HLP cultures, washed, and then labeled with secondary antibody FITC-goat-anti-human Ig (Jackson Laboratories). As shown in FIG. 2, only culture media from very early passages of the HLP (passage 2) produced IgM that could recognize cell surface GD2 (FIG. 2B). However, this activity was quickly lost after subculturing the HLP for a few weeks (FIG. 2C). These results suggest that the cells producing specific GD2-reactive IgM are slow growers in the HLP and are quickly overpopulated by non-producers or nonspecific antibody producers, or that the production of this IgM is not stable. The murine anti-GD2 IgM antibody MAb-126 (ATCC# HB-8568™) was used as a positive control and demonstrated robust GD2-specific binding (FIG. 2D).

EXAMPLE 2

Figure 3A:
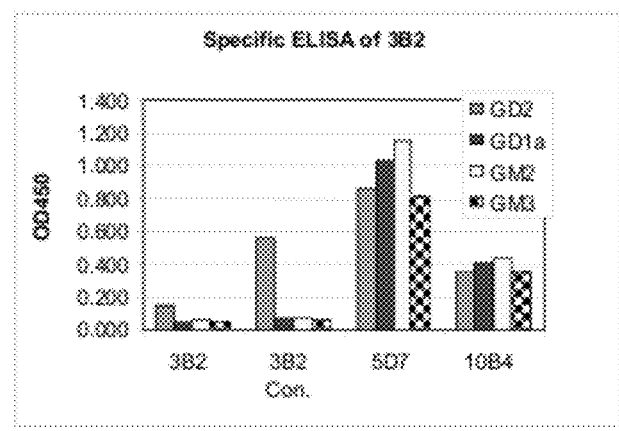
FIG. 3A shows binding characteristics of IgM antibodies contained in media of hydridomas 3B2, 5D7, and 10B4 for gangliosides GD2, GD1a, GM2, and GM3.
Figure 3B:
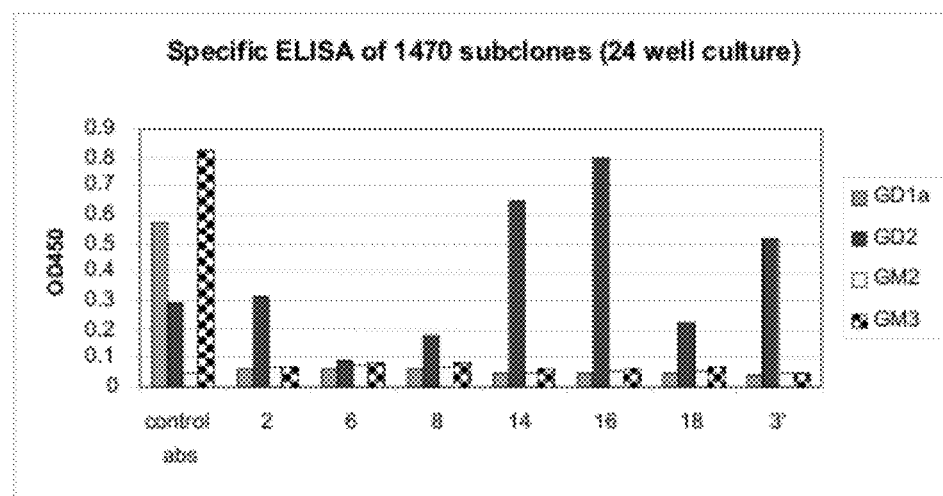
FIG. 3B shows binding characteristics of IgM antibodies contained in media of the 1470 hydridoma subclone for gangliosides GD2, GD1a, GM2, and GM3.

Hybridomas Derived from the HLP Produce GD-2 Specific IgM that Mediates CDC Activity on GD2-Positive Cells In order to generate EBV-null hybridoma lines that produce anti-GD2 specific IgM, cells from early passages of the HLP were fused with fusion partners A6 (ATCC CRL-8192) or K6H6/B5 (ATCC CRL-1823) to form hybridomas. Due to the apparently low abundance of GD2-specific subclones in the HLP, 80,000 clones were screened by GD2-specific ELISA. Approximately 5-10% of antibody preparations from these hybridoma lines showed positive GD2 reactivity. However, over 90% of the GD2 positive clones showed reactivity to multiple gangliosides when screened for specificity using a panel of gangliosides (GD1, GM2 and GM3) (FIG. 3A—clones 5D7 and 10B4). Moreover, the majority of polyreactive antibodies cross-reacted to a panel of non-related control proteins (data not shown). These results suggest that the lymphoblast cells producing GD2-specific IgM are rare in the HLP.

Figure 4:
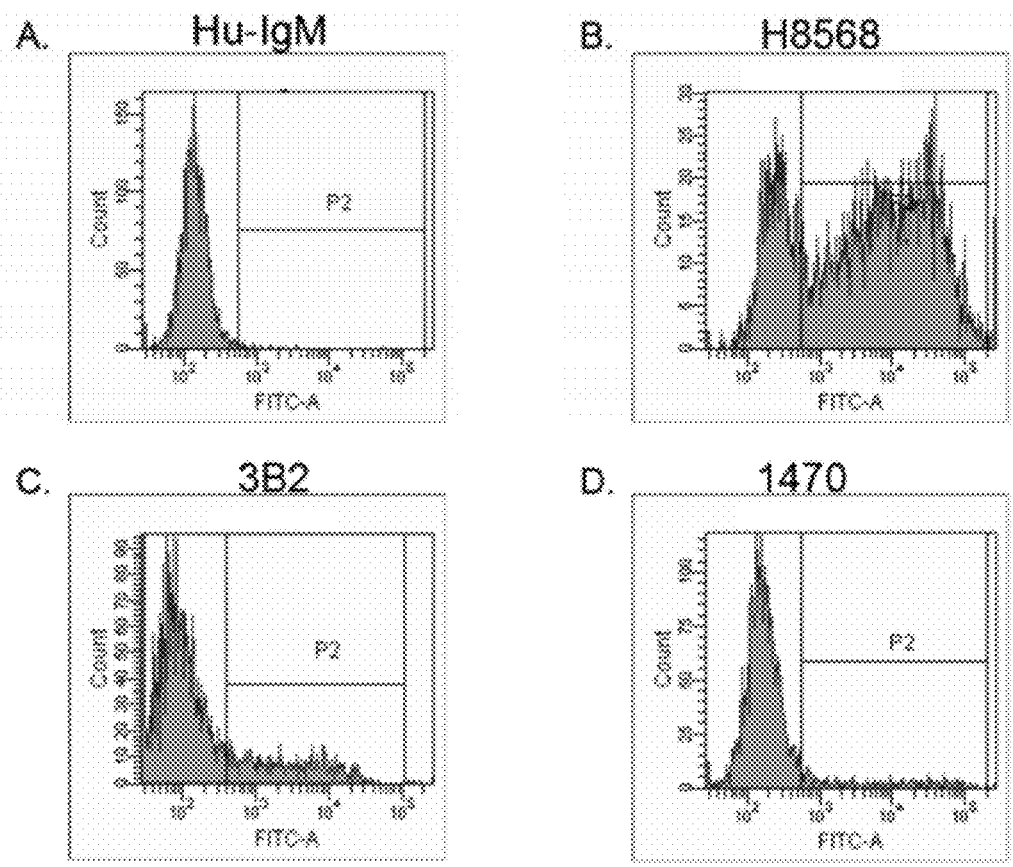
FIG. 4 shows binding levels of IgM antibodies produced by hybridoma 3B2 and 1470 cell cultures on GD2-expressing 1205LU melanoma cells, as analyzed by FACS.

Subcloning and screening efforts led to the isolation of GD2-specific IgM-producing hybridoma cell lines. Two GD2 specific hybridoma lines, 3B2 and 1470, were isolated. Cultures of both cell lines were seeded at $0.3\text{-}0.4e^6$/mL of cells of seeding density and split every 3 to 4 days, which yielded 3-8 mg/mL of IgM in spent medium. Ganglioside-specific ELISA revealed positive reactivity with GD2 only and no reactivity to three control gangliosides (GD1a, GM2, and GM3) (FIGS. 3A and B), suggesting that these cells produce GD2-specific antibodies. In addition, FACS analysis showed positive staining of 1205LU human melanoma cells with 3B2 and 1470 antibodies, suggesting that these antibodies can recognize GD2 on the cell surface (FIG. 4). Molecular analyses of clones 3B2 and 1470 were performed to determine clone origin. Light chain specific ELISA showed that both clones secreted IgM containing a kappa light chain (data not shown). Sequence analysis of cDNA from these cells revealed identical heavy and light chain sequences, suggesting that the two clones were derived from the same HLP lymphoblast clone (data not shown).

Figure 5:
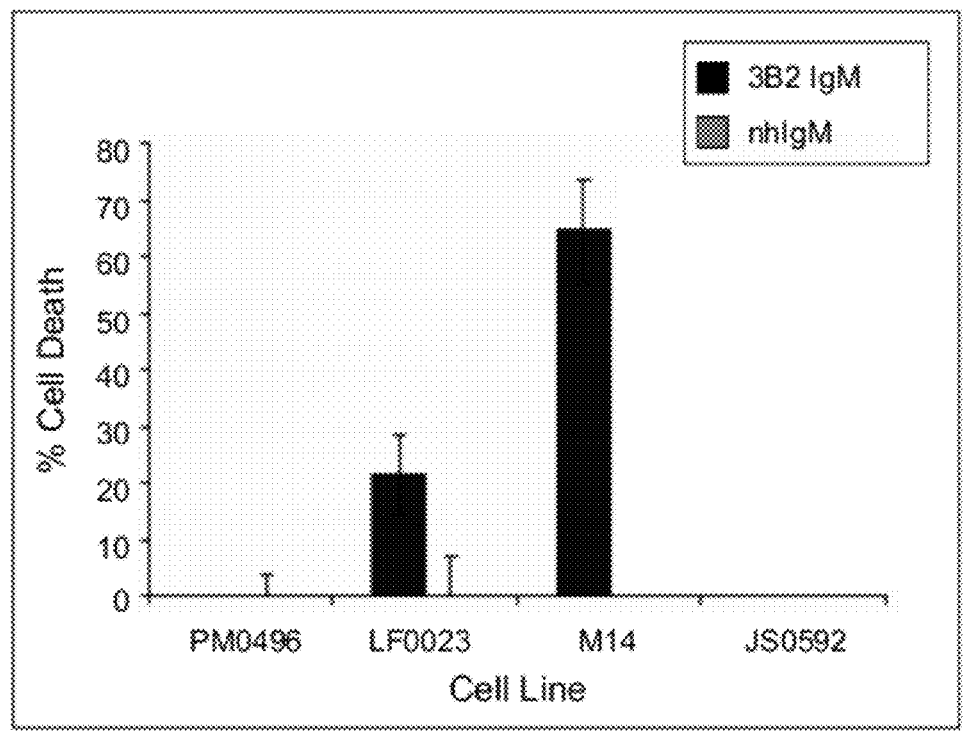
FIG. 5 shows cell death due to complement-dependent cytotoxicity (CDC) mediated by IgM obtained from hybridoma 3B2 tissue culture supernatant or non-GD2-specific human IgM (nhIgM).

Partially purified antibody from the 3B2 culture was used to assess the ability of this antibody to mediate complement-dependent cytotoxicity (CDC) on GD2 expressing melanoma cell lines, as this activity is largely dependent on the conformation that the antibody assumes when bound to its antigen (Janeway et al., Immunobiology, 9-12 ($5^{th}$ ed. 2001)). Melanoma target cell lines (GD2-positive cell lines LF0023 and M14, and GD2-negative cell lines PM0496 and JS0592) were cultured in RPMI1640 supplemented with 10% FBS, 2 mM Glutamine, non-essential amino acids, and 6 µM HEPES and harvested with trypsin before use. Target cells were incubated with 3B2 IgM-containing supernatant in the presence of 20% human serum. After incubation for 1 hour at 37° C., live cells were identified with Cell Titer Glo® reagent, (Promega Corp., Madison, Wis.). Percent killing was determined as the ratio of signal from treated versus untreated cells. The data in FIG. 5 suggest that IgM produced by the 3B2 clone can elicit a potent CDC reaction on certain GD2 positive melanoma cell lines.

Molecular analyses were performed to determine whether clones 3B2 and 1470 were infected with EBV. Six PCR primer pairs ((EBNA2-1141f (SEQ ID NO: 45) and EBNA2-1440r (SEQ ID NO: 46); EBV2001f (SEQ ID NO: 47) and EBV2622r (SEQ ID NO: 48); EBV1901F (SEQ ID NO: 49) and EBV2822R (SEQ ID NO: 50); EBV169461f (SEQ ID NO: 51) and EBV170100r (SEQ ID NO: 52); EBV169480f (SEQ ID NO: 53) and EBV170080r (SEQ ID NO: 54); EBV8491F (SEQ ID NO: 55) and EBV9020r (SEQ ID NO: 56)) were designed to verify the existence and intactness of the EBV genome. One of the primer pairs amplified the open reading frames of EBNA-2; two overlapping sets each amplified the 5' and 3' end of the EBV genome; and one pair amplified the origin of replication. Initially, both 3B2 and 1470 clones were EBV positive as demonstrated by genomic PCR (data not shown). However, further subcloning by limiting dilution plating at less than one cell per well generated subclones of the 3B2 and 1470 lines that did not contain the EBV genome, as determined by EBV-specific PCR analysis (data not shown).

EBV-negative 3B2 subclones (AB527-HYB-3B2-EBVnull) have been placed with the Amer. Type Cult. Coll. (10801 University Blvd., Manassas, Va. 20110-2209) on Jul. 16, 2008 and have been assigned Accession No. PTA-9376. AB527-HYB-3B2-EBVnull subclones were subjected to a second round of subcloning to identify clones that produced a single form of immunoglobulin J-chain, as the original hybridoma may produce human or mouse J-chain. To identify clones possessing a single form of J-chain, or J-chain-null clones, RT-PCR was performed using primers specific for human J-chain (hu-285F (SEQ ID NO: 57) and hu-418R (SEQ ID NO: 58)), or mouse J-chain (m-230F (SEQ ID NO: 59) and m-370R (SEQ ID NO: 60)). The results indicated that the 3B2 subclone, AB527-HYB-3B2-3C9, is EBV null, human J-chain null, murine J-chain positive and secretes approximately 30 mg/L of monoclonal, GD2-specific IgM in static culture.

EXAMPLE 3

Production of a Transfectoma Cell Line Expressing GD2-Specific IgM

Total RNA isolated from AB527-HYB-3B2-3C9, the EBV null, human J-chain null, murine J-chain positive hybridoma, was reverse transcribed into cDNA and used as template for the PCR amplification of the IgM heavy chain, using primers corresponding to SEQ ID NOs: 33 and 35, and light chain, using primers corresponding to SEQ ID NOs: 36 and 38. The heavy chain nucleotide sequence amplified from AB527-HYB-3B2-3C9 encodes a polypeptide having the amino acid sequence of SEQ ID NO: 40, and the light chain nucleotide sequence amplified from AB527-HYB-3B2-3C9 encodes a polypeptide having the amino acid sequence of SEQ ID NO: 42. A second round of PCR amplification was performed to add a human leader sequence, along with 5' and 3' restriction endonuclease recognition sites were introduced in order to facilitate cloning of the amplicons into pEE6.4 (heavy chain) and pEE14.4 (light chain), both vectors are supplied as part of Lonza Biologics Glutamine Synthetase Expression System (GS System). The second round PCR amplification of the IgM heavy chain was conducted using primers corresponding to SEQ ID NOs: 34 and 35, while the light chain amplification used primers corresponding to SEQ ID NOs: 37 and 38.

Figure 6:
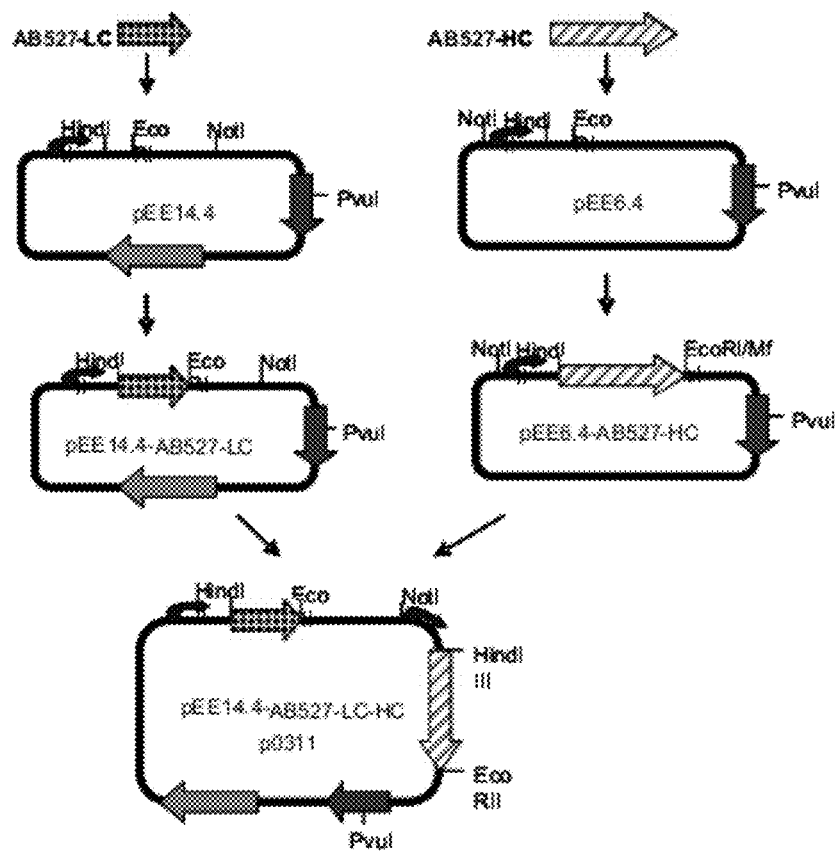
FIG. 6 provides a schematic representation of the cloning of AB527 antibody heavy and light chain segments.
Figure 7:
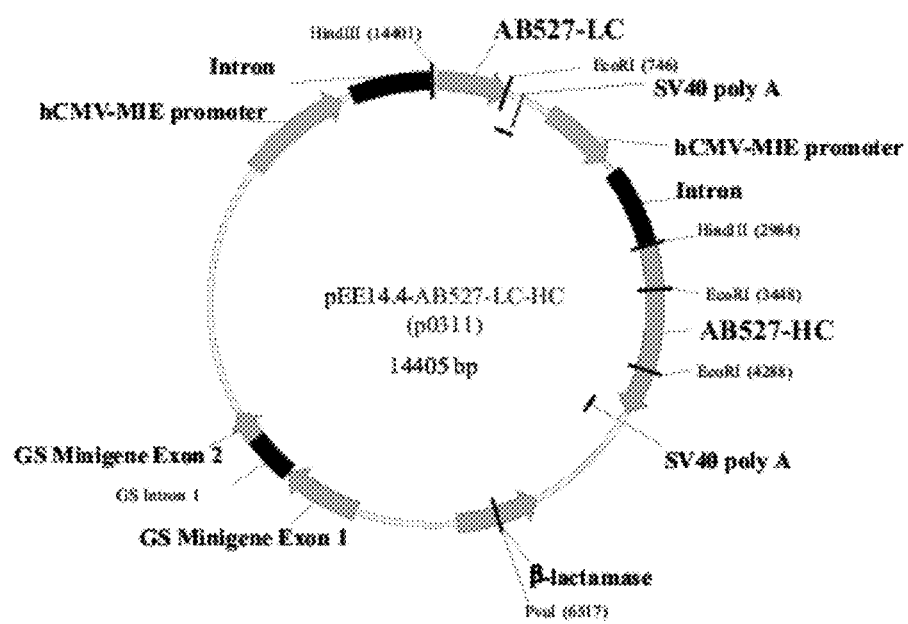
FIG. 7 provides a schematic representation of the AB527 expression vector.

PCR amplified light chain cDNA was digested with HindIII and EcoRI and ligated into similarly cut pEE14.4, while heavy chain cDNA was digested with HindIII and MfeI and ligated into pEE6.4 digested with HindIII and EcoRI (MfeI and EcoRI leave compatible "sticky" ends). After verification of the nucleotide sequence of the heavy and light chains, the heavy chain expression cassette was introduced in to pEE14.4-AB527-LC as a NotI/PvuI fragment to construct the final expression vector pEE14.4-AB527-LC-HC (p0311) (FIG. 6). pEE14.4 is a 10 Kb vector which contains a glutamine synthase mini gene, allowing for selection of stable transfectants in the presence of the GS inhibitor L-methionine sulfoximine (MSX). Transcription of the cDNA inserts in this vector is controlled by the human CMV immediate early promoter, upstream of the cDNA insert is the hCMV-MIE 5' untranslated region including introns 1, downstream of the cDNA insert is the SV40 polyadenylation signal allowing for efficient polyadenylation of the transcript (FIG. 7).

CHO cells were transfected with linearized, double-gene vector p0311 by electroporation to allow for expression of recombinant GD2-specific IgM. Following transfection the cells were plated in 96-well plates using non-selective medium containing dialyzed fetal bovine serum (dFBS) and glutamine synthase supplement. The following day selective medium containing dFBS, glutamine synthase supplement and MSX (10 µM final concentration) was added to each well, enabling selection of cells containing the expression vector. Only colonies perceived to have come from a single transfected cell were pursued.

Transfectants were screened for the presence of human IgM by ELISA. Colonies were expanded in serum-containing selection medium and surviving colonies were examined by quantitative secondary assay to identify the highest-producing colonies. The highest-producing transfectants were adapted to chemically defined IS-CHO-CD™ medium (Irvine Scientific, Santa Ana, Calif.) and seeded at 2,500 cells/well in flat bottom 96 well plates (80 plates) in media containing 10 µM MSX. Drug-resistant colonies were analyzed for IgM production by ELISA. Colonies positive for IgM production were scaled up and analyzed for antibody productivity in subsequent secondary (6 well) and tertiary (20 mL shake flask) assays. This resulted in the identification of an IgM-producing CHO-K1SV transfectoma clone, 127C8. The 127C8 clone does not express J-chain, therefore, the recombinant AB527 IgM produced by this cell line is J-chain-deficient. The amino acid sequences of the heavy and light chains of AB527 are represented by SEQ ID NOs: 40 and 42, respectively.

EXAMPLE 4

AB527 Binds Specifically to GD2 In Vitro

Figure 8:
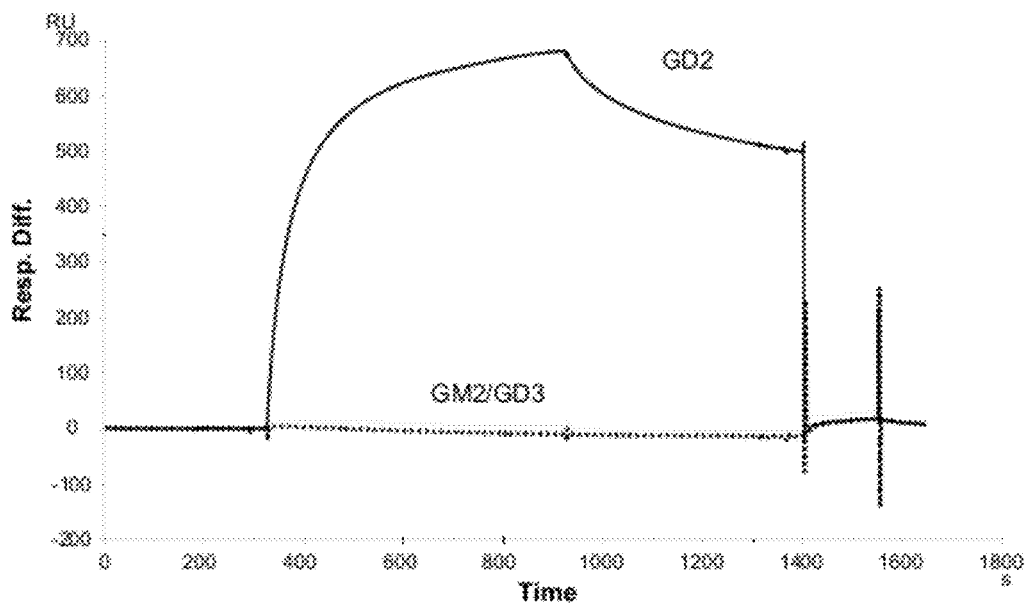
FIG. 8 illustrates the binding activity of AB527 for the gangliosides GD2, GM2, and GD3, as measured by surface plasmon resonance.

Several experiments were conducted to determine whether recombinant AB527 could bind to purified GD2 in vitro. Initially, surface plasmon resonance experiments were performed to not only determine whether recombinant AB527 would bind to GD2, but also to determine whether it exhibited affinity for GM2 or GD3 (FIG. 8). The experiments were performed as follows: 40 µL of 0.3 mg/mL solutions of GD2 (BioDesign), GD3 (HyTest), and GM2 (USBiological) in 10 mM HEPES, 150 mM NaCl, 3 mM EDTA (HBS-E) containing 30% ethanol were injected over flow cells 2, 3, and 4, respectively, of a CMS chip at a flow rate of 5 µl/minute using a BIAcore 3000 instrument. Five repeated injections of 20 µL 10 mM NaOH were done following immobilization of each ganglioside until a stable baseline was achieved. Next, 80 µL of 200 nM recombinant AB527 in HBS-E buffer was injected over all 4 flow cells (flow cell 1 was used as a reference flow cell) at a flow rate of 20 µL/minute. Dissociation of recombinant AB527 was followed for 6 minutes. The chip surface was regenerated with 50 µL of 10 mM NaOH.

Figure 9:
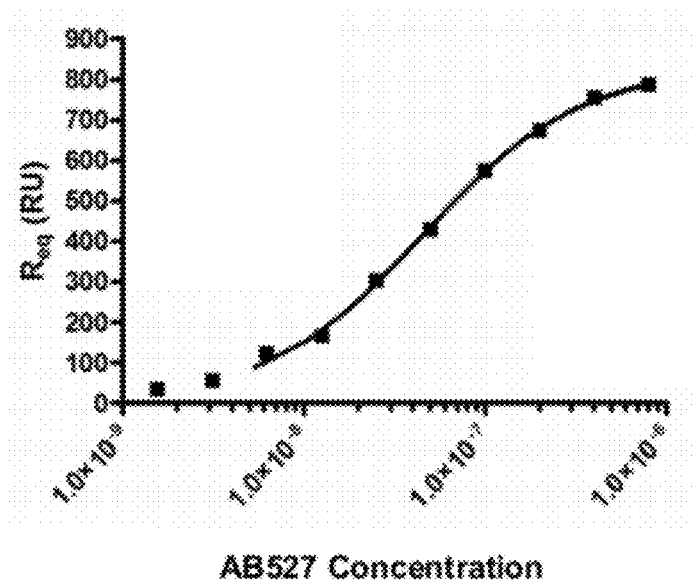
FIG. 9 provides a graphical representation of AB527 binding equilibrium as measured by surface plasmon resonance for differing concentrations of antibody bound to GD2.

To better characterize the binding kinetics of AB527, additional surface plasmon resonance experiments were conducted using serial dilutions of AB527 and GD2 immobilized on a BIAcore CM5 chip. Briefly, two-fold serial dilutions of AB527, starting at 800 nM, were injected over a GD2-containing CM5 chip, described above, at a flow rate of 20 µL/minute in HBS-E buffer. The chip surface was regenerated between each cycle with 50 µL of 10 mM NaOH. Equilibrium binding at each concentration ($R_{eq}$) was determined for each concentration tested in BIAevaluation software and a plot of $R_{eq}$ vs. concentration was then done. The resulting data were fitted to a non-linear steady-state binding model using GraphPad Prizm® software. When the $R_{eq}$ is plotted as a function of AB527 concentration, the steady state $K_d$, or the concentration of AB527 at which one-half maximal binding is achieved, can be determined (FIG. 9). For AB527 binding to GD2, the steady state $K_d$ value is $4.5 \times 10^{-9}$ M.

Figure 10:
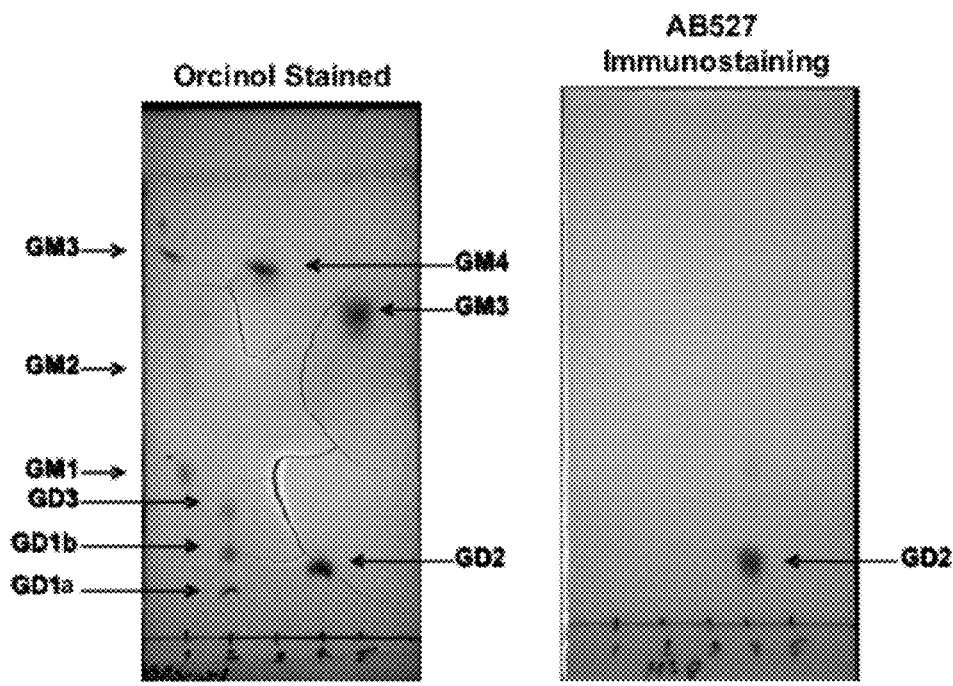
FIG. 10 shows the staining patterns of various gangliosides separated by thin layer chromatography. Orcinol staining shows non-specific ganglioside staining, which provides a basis for comparison with AB527 staining.

The specificity of recombinant AB527 was also tested by immunostaining various gangliosides separated by thin layer chromatography (TLC). The following gangliosides were used in the immunoTLC analysis: GM mix (Matreya, 0.5 mg/mL in ethanol contains GM1, GM2, and GM3), GD mix (Matreya, 0.5 mg/mL in ethanol, contains GD1a, GD1b, and GD3), GM4 (Matreya, 1 mg/mL in ethanol), GD2 (BioDesign, 1 mg/mL in ethanol), and GM3 (USBiological, 1 mg/mL in ethanol). A total of 2 µl of each ganglioside was spotted on to a 5×10 cm silica TLC plate (EMD Chemicals, Inc.) and developed in a solution having a ratio of 58:37:8 of $CHCl_3$, MeOH, and 0.1M $CaCl_2$. TLC plates were stained for total ganglioside by spraying with 0.1% orcinol in 1.36N $H_2SO_4$ and heating at 100° C. For immunoTLC analysis, developed plates were first treated with 0.1% polyisobutylmethacrylate in $H_2O$, and then dried. The plates were then blocked for 1 hour with 1% BSA in 1× phosphate-buffered saline (PBS). The blocked plate was then incubated in 2 ng/mL AB527 in 1×PBS containing 1% BSA overnight at 4° C. The plates were subsequently washed with 1×PBS, then incubated with goat anti-human IgG/IgM-horseradish peroxidase conjugate diluted 1:4000 in PBS containing 1% BSA. Plates were washed, and bound antibody was detected by incubating the plates in 0.3 mg/mL 4-chloro 1-napthol and 0.03% $H_2O_2$. The comparative staining results are shown in FIG. 10.

EXAMPLE 5

AB527 Labels GD2-Expressing Cells

Figure 11:
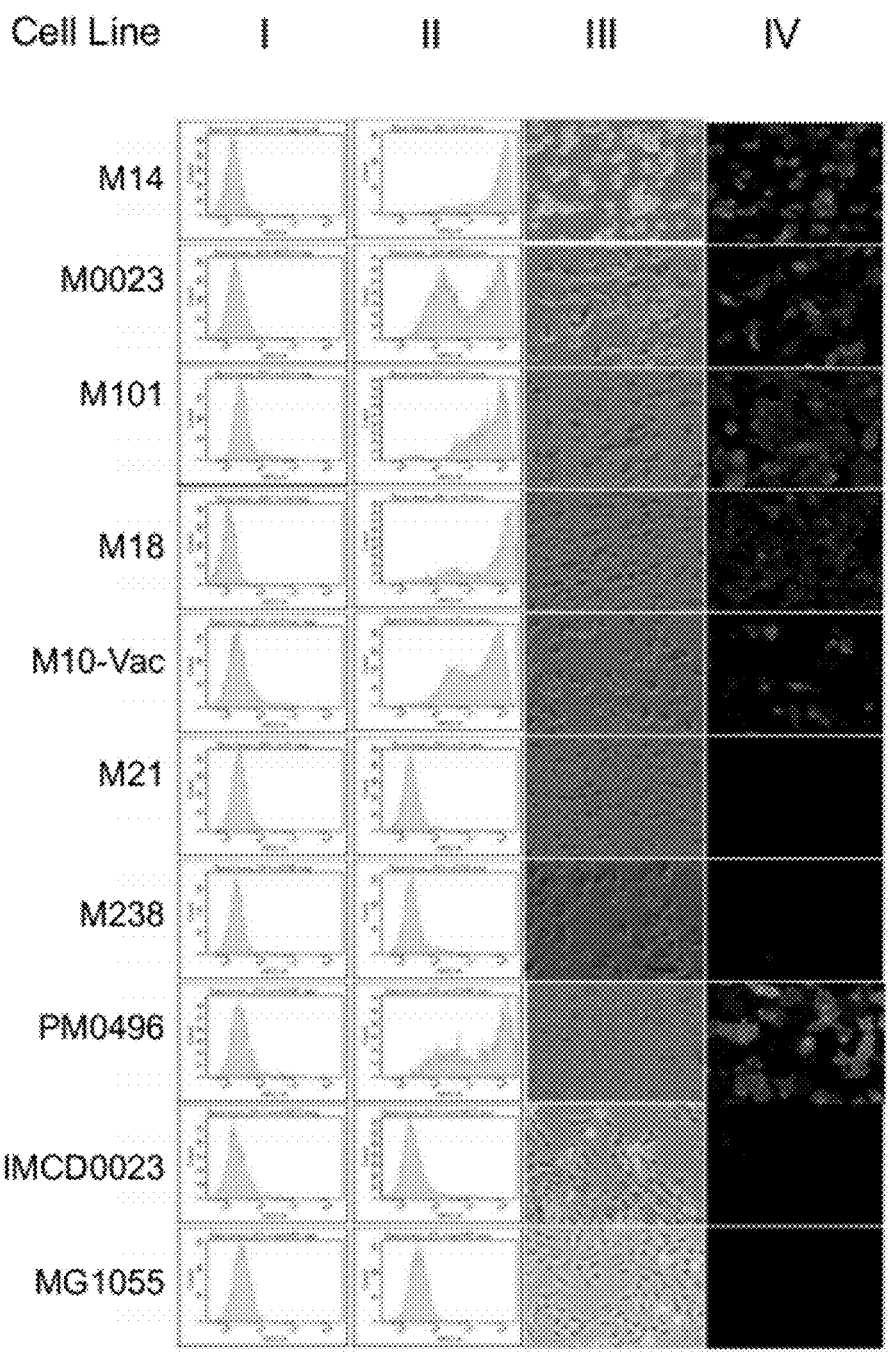
FIG. 11 shows flow cytometry (columns I and II) and comparative light microscopy and immunofluorescence microscopy images (columns II and IV) of AB527 binding to human melanoma cell lines that express GD2 at the cell surface (cell lines: M14, M0023, M101, M18, M10-Vac, PM0496) or lack GD2 expression (GD2-negative lines: M21, M238, IMCD0023, MG1055).

The ability of AB527 to specifically label GD2-expressing melanoma cell lines was assessed. GD2-positive lines: M14, M0023, M101, M18, M10-Vac, and PM0496, and GD2-negative lines: M21, M238, IMCD0023, MG1055 were cultured separately in RPMI1640 supplemented with 10% FBS, 2 mM L-Glutamine, non-essential amino acids, and 6 µM HEPES and harvested with trypsin. Trypsinized cells were incubated with either 10 µg/mL of control IgM (human IgM, Pierce cat#31146) (column I) or 10 µg/mL of AB527 (column II) for 1 hour on ice. After 3 washes with 1×PBS, cells were incubated with 10 µg/mL FITC-labeled goat anti human Ig (H+L) antibody (Southern Biotech, Birmingham, Ala.) for 1 hour on ice, followed by either flow cytometry (columns I and II, respectively) or light microscopy and immunofluorescence microscopy analysis (columns III and IV, respectively). As shown in FIG. 11, AB527 labeled cells express GD2 on their surface (column II). Conversely, none of the cell lines examined showed staining with non-GD2-specific human IgM (column I) Immunofluorescent studies showed a direct correlation with flow cytometry data (column IV), light microscopy images are also shown for comparative purposes (column III).

Figure 12:
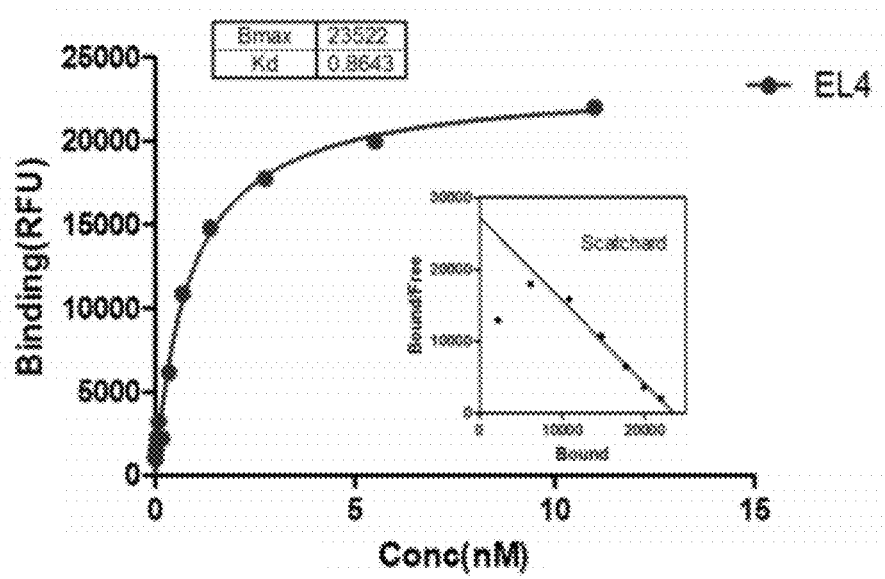
FIG. 12 provides a graphical representation of a saturation binding curve and corresponding Scatchard plot that characterizes the binding of AB527 to EL4 cells.

Cell-based ELISAs were performed to assess AB527 binding to the GD2-expressing cell lines M14, LLC-MK2, EL4 cells and to CHO-K1 cells (negative control), which provided the data to perform corresponding Scatchard analyses. FIG. 12 provides a representative set of Scatchard data for EL4 cells. AB527 binding to M14 and LLC-MK2 cells was determined to be nearly identical (0.13±0.02 nM and 0.15±0.04 nM, respectively). Binding to EL4 cells was somewhat lower (0.93±0.16 nM). This difference may be due to the markedly lower expression of GD2 observed on EL4 cells relative to M14 and LLC-MK2 (data not shown). For these experiments, M14, LLC-MK2, EL4, and CHO-K1 cells were obtained from the American Tissue Type Collection (ATCC, Manassas, Va.). M14, EL4, and CHO-K1 cells were cultured in RPMI supplemented with 10% fetal bovine serum. LLC-MK2 cells were cultured in Medium 199 supplemented with 1% horse serum. Cells were suspended in 1×PBS and added to a black, U-bottomed microtiter plate (Grenier cat. #665209) at $2.5 \times 10^6$ cells/well, then pelleted at 1500 rpm for 5 minutes at room temperature. Supernatant was discarded, and cells were resuspended in a solution containing AB527 starting at 20 µg/mL serially diluted 1:2 in PBS containing 2% BSA. Cells were incubated with antibody for 1 hr at room temperature. Cells were washed three times with 200 µL PBS containing 2% BSA and 0.05% Tween®-20, centrifuging at 1500 rpm for 5 minutes to collect cells between wash steps. Cells were then incubated in a PBS solution containing 1 µg/mL horseradish peroxidase conjugated goat anti-human IgG/IgM (Jackson Immunoresearch) and 2% BSA for 1 hr at room temperature. Cells were washed as above. Bound AB527 was detected using QuantaBlu™ fluorescent substrate (Pierce), with excitation/emission wavelengths of 325 nm/420 nm, in a SpectraMax® M5 multimodal plate reader (Molecular Devices). Raw data was plotted in SoftMax Pro® (ver. 5.2) and fitted to a 4-parameter model. Data analysis was performed in GraphPad Prizm® software (ver. 4.03). Non-specific background was first subtracted (binding to CHO-K1 cells), and data were then analyzed by Scatchard analysis.

Figure 13:
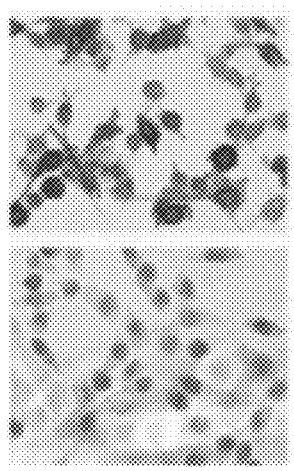
FIG. 13 shows AB527 staining of GD2 positive (M14) and negative (MG1055, RPMI7951 and JS0592) melanoma cell lines Immunohistochemical analysis was performed using biotinylated AB527 (FIG. 13A) or biotinylated, non-GD2-specific, control IgM (FIG. 13B).
Figure 13:
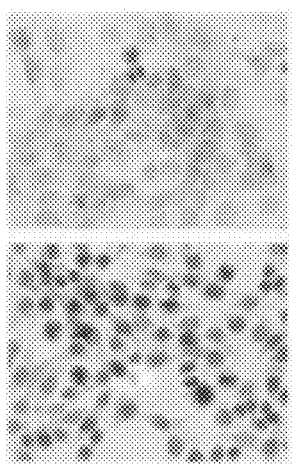
Figure 13:
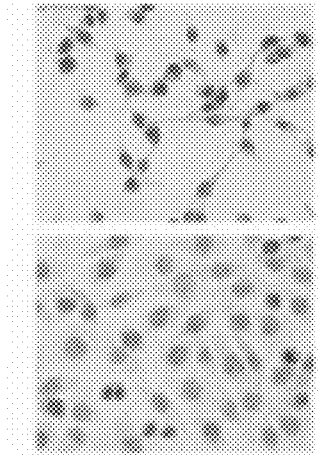
Figure 13:
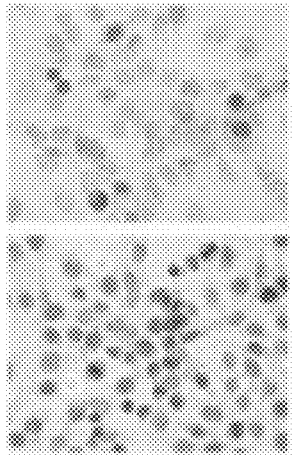

Immunohistochemical (IHC) experiments were conducted to determine whether AB527 exhibited cross-reactivity to melanoma cells that do not express GD2. Purified AB527, as well as a non-specific human IgM (Pierce cat#31146), were biotinylated using NHS ester coupling chemistry, at a molar ratio of 50:1 biotinylation reagent (EZ-Link™ sulfo-NHS-LC-biotin, Pierce cat#21335) in phosphate-buffered saline, according to the provided instructions, and used to stain various GD2-positive (M14) or GD2-negative (MG1055, RPMI7951 and JS0592) cell lines. Briefly, each melanoma cell line was seeded on chamber slides and cultured overnight in RPMI1640 supplemented with 10% FBS, 2 mM L-Glutamine, non-essential amino acids, and 6 µM HEPES. Cells were washed once with 1×PBS and formalin-fixed. Fixed cells were incubated overnight with 1 µg/mL biotinylated AB527 or biotinylated nonspecific human IgM (negative control) and labeled cells were detected using BioGenex Super Sensitive™ Link-Label IHC Detection System. As shown in FIG. 13A, AB527 specifically binds to GD2 positive cells and has minimal cross reactivity with GD2 negative cells, while the non-specific isotype control antibody does not stain either cell type (FIG. 13B).

Figure 14:
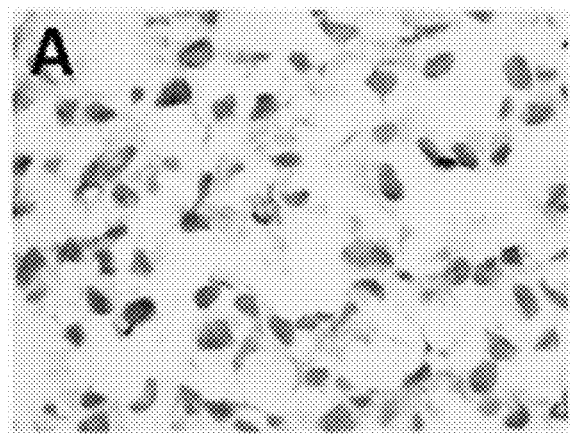
FIG. 14 shows that M14 tumor sections are not immunoreactive with biotinylated hIgM (14a), but do show immunoreactivity with biotinylated AB527 (14b).
Figure 14:
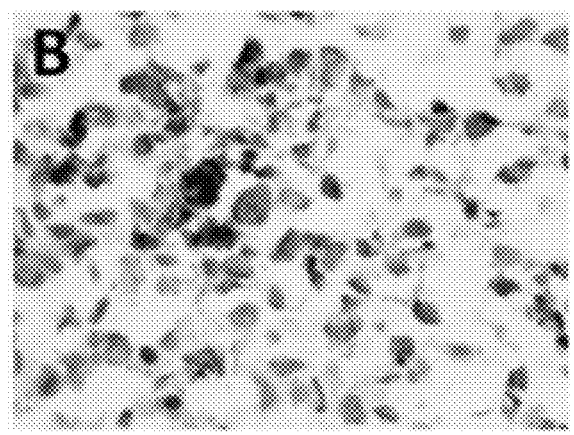

Binding characteristics of AB527 were also assessed using tumor and normal tissue samples. AB527 and a nonspecific normal human IgM (hIgM) were biotinylated at Covance Research Products and used for IHC studies at Charles River Laboratories. Human melanoma cancer cells, M14, were implanted in nude rats to establish xenograft tumors, which were then used as GD2 positive control tissue for IHC method development. Preliminary studies using a direct avidin-biotin-peroxidase complex (ABC) procedure yielded positive staining of M14 tumor sections with biotinylated AB527 (FIG. 14(b)) but not with biotinylated hIgM (FIG. 14(a)). As expected, lymphocytes in cryosections of normal human spleen did not stain with either antibody. After titration of the antibodies, the staining concentrations for biotinylated AB527 and biotinylated hIgM selected for the GLP human tissue cross-reactivity study were set at 3 and 15 μg/mL. Using this method, a study was conducted to determine AB527 binding in 35 normal human tissues (3 samples/donors per tissue). As expected, high affinity membranous staining (positive cell membrane staining at the lower concentration of AB527-3 μg/mL) could be detected in M14 tumor sections. As shown in table 2, high affinity membranous staining was only found in the epithelial cells of esophagus (2 of 3 samples), fallopian tube (1 of 3 samples), and ureter (1 of 3 samples), as well as in decidual cells of placenta (3 of 3 samples), and reticular cells of thymus (2 of 3 samples). All the other tissues showed no high affinity membranous staining (table 2).

results of the experiments using AB527 described in this Example are summarized in table 3.

TABLE 3

Comparison of FACS, Immunofluorescence Microscopy and CDC analysis of human melanoma cell lines treated with AB527.

| Cell Line | AB527 FACS Staining | AB527 IHC | AB527-mediated CDC Killing |
|---|---|---|---|
| M14 | + | + | + |
| LF0023 | + | + | + |
| M101 | + | + | + |
| M18 | + | + | + |
| M10VAC | + | + | + |
| M21 | +/− | − | − |
| M238 | − | − | − |
| PM0496 | + | + | − |
| IMCD0023 | +/− | − | − |
| MG1055 | − | − | − |

Figure 16:
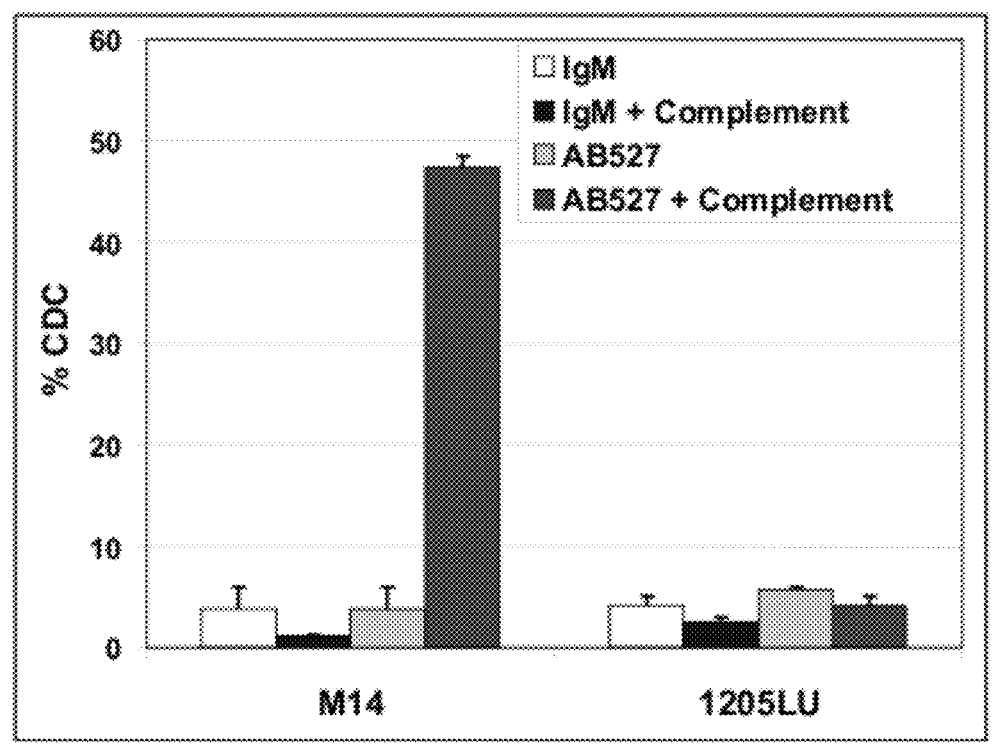
FIG. 16 is a graphical representation of AB527-mediated CDC in the presence or absence of complement, for human tumor cells that either express GD2 (M14) or do not express GD2 (1205LU).

Additional work was done to show that AB527 facilitates CDC only of cells that express GD2 in the presence of complement. As shown in FIG. 16, AB527-mediated CDC activity only occurred to appreciable levels in the presence of

TABLE 2

AB527 Immunohistochemistry in Normal Human Tissues

| Tissue | Positive/Total (Cell Type) | Tissue | Positive/Total (Cell Type) | Tissue | Positive/Total (Cell Type) |
|---|---|---|---|---|---|
| Adrenal | Negative | Liver | Negative | Skin | Negative |
| Blood Cells | Negative | Lung | Negative | Spinal Cord | Negative |
| Blood Vessels | Negative | Lymph Node | Negative | Spleen | Negative |
| Bone Marrow | Negative | Ovary | Negative | Striated Muscle | Negative |
| Brain (Cortex) | Negative | Fallopian Tube | 1/3 (Epithelium) | Testis | Negative |
| Brain (Cerebellum) | Negative | Pancreas | Negative | Thymus | 2/3 (Reticular Cells) |
| Breast | Negative | Parathyroid | Negative | Thyroid | Negative |
| Eye | Negative | Peripheral Nerve | Negative | Tonsil | Negative |
| Esophagus | 2/3 Epithelium | Pituitary | Negative | Ureter | 1/3 (Epithelium) |
| GI Tract | Negative | Placenta | 3/3 (Decidual Cells) | Urinary Bladder | Negative |
| Heart | Negative | Prostate | Negative | Uterus (Body) | Negative |
| Kidney | Negative | Salivary Gland | Negative | Uterus (Cervix) | Negative |

EXAMPLE 6

AB527 Facilitates Complement Dependent Cytotoxicity of Cells Expressing GD2

Figure 15:
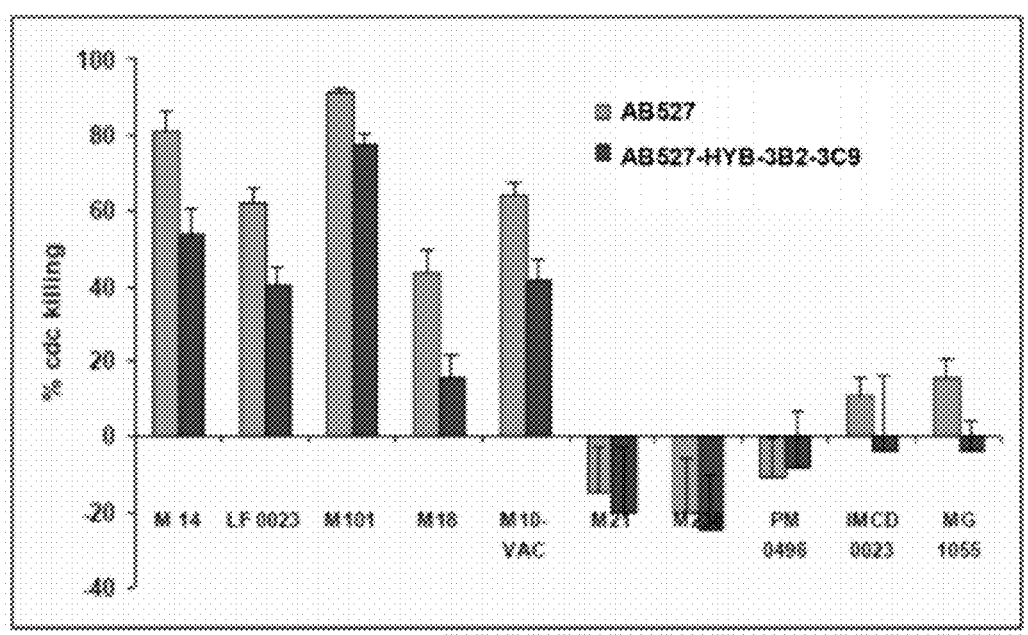
FIG. 15 shows a comparison of complement-dependent cytotoxicity (CDC) of GD2 positive or GD2 negative cells mediated by either IgM obtained from hybridoma AB527-HYB-3B2-3C9 or AB527 IgM.

To determine whether AB527 mediates CDC, the melanoma cell lines described above for FIG. 11 were incubated with partially purified antibody from the AB527-HYB-3B2-3C9 clone or AB527. Target cells were cultured in RPMI1640 supplemented with 10% FBS, 2 mM L-Glutamine, non-essential amino acids, and 6 μM HEPES and harvested with trypsin before use. Target cells were incubated with 10 μg/mL of either AB527 or AB527-HYB-3B2-3C9 clone IgM in the presence of 20% human serum. After incubation for 1 hour at 37° C., live cells were identified with Cell Titer Glo® reagent (Promega Corp., Madison, Wis.). Percent killing was determined as the ratio of signal from treated versus untreated cells. The data in FIG. 15 show that both antibodies can elicit a potent CDC reaction on certain melanoma cell lines, with AB527 consistently causing a greater degree of CDC. The complement and GD2-expressing cells, such as M14 cells, as opposed to 1205LU cells, which are human tumor cells that do not express GD2.

Figure 17:
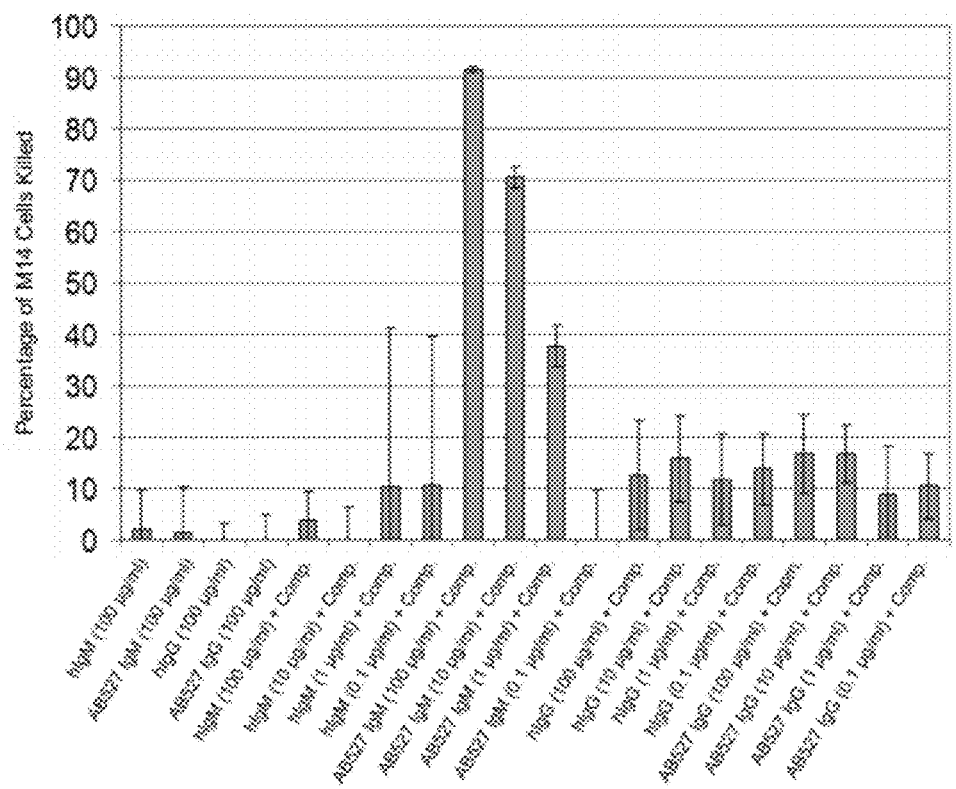
FIG. 17 illustrates the relative degree of CDC activity for non-specific human IgM, AB527, non-specific hIgG, and isotype-switched AB527 having an IgG1 constant region.

To assess the in vitro ability of IgG1 isotype-switched AB527 to induce CDC, the HindIII/BamHI variable region DNA fragment of AB527 was cloned in-frame into a HindIII/BamHI digested pEE6.4 vector containing the IgG1 constant region. Co-expression with the AB527 light chain caused the production of an IgG1 version of AB527. The ability of this antibody to mediate CDC of M14 cells was compared to the IgM version of AB527 at 1-100 μg/mL, as shown in FIG. 17.

Figure 18:
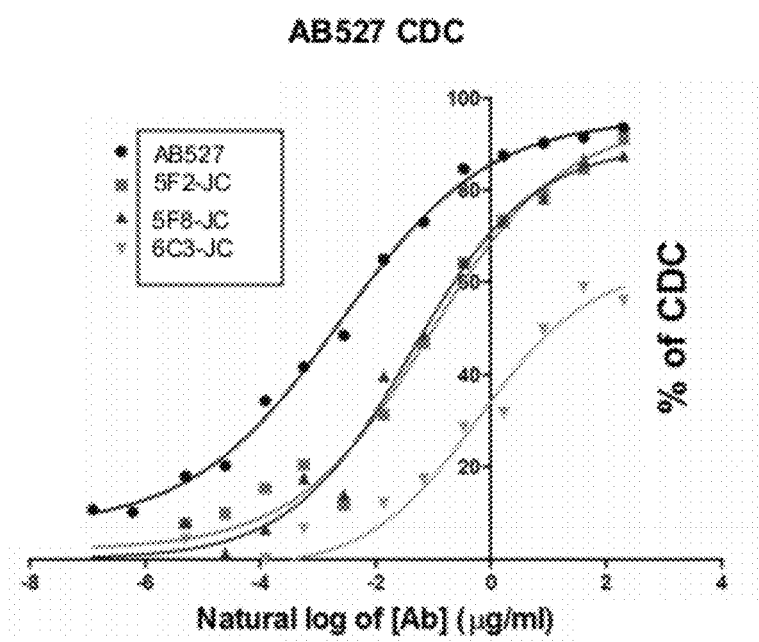
FIG. 18 shows the relative degree of CDC activity for AB527 antibodies with or without J-chain (JC).

Studies were also conducted to assess the role that J-chain might play in AB527-mediated CDC. To produce AB527 IgM molecules having J-chain, plasmid p0362, which encodes J-chain, was transfected into CHOK1-SV cells and a stable, J-chain-expressing clonal line was generated. The AB527 expression plasmid was then introduced into this line to generate clones expressing AB527 and J-chain. Three clones named 5.F2-JC, 5.F8-JC, and 6.C3-JC were isolated. The antibodies were purified in parallel to compare their relative CDC activity against a non-J-chain containing version of AB527. Dose response curves are shown in FIG. 18. The calculated 90% of effective dose (ED90) for AB527, 5.F2-JC, 5.F8-JC, and 6.C3-JC was 1.21, 4.35, 2.52, and 6.81 µg/mL, respectively. IgM containing J-chain (5.F2-JC, 5.F8-C, and 6.C3-JC) appeared to be less effective at mediating CDC compared to AB527 without J-chain.

EXAMPLE 7

Capture of IgM from Conditioned Culture Supernatant by Protein A Affinity Chromatography A column was packed with CPG3000A-protein A resin (Millipore). The volume of resin used to capture IgM was estimated, with the understanding that 1 mL of resin binds approximately 8 mg of IgM at a flow rate of 76 cm/h (table 4). Once the column was loaded with the desired amount of resin, it was connected to an FPLC apparatus and washed with 5 column volumes of purified water; 3 column volumes of 20 mM HCl, pH 1.5 (buffer A2); and 3 column volumes of 6 M guanidine.HCl (buffer A3). Before loading sample, the column was equilibrated with 5 column volumes of a 10 mM sodium phosphate buffer containing 200 mM NaCl and 0.01% Tween®-80, pH 7.5 (buffer A1).

Figure 19:
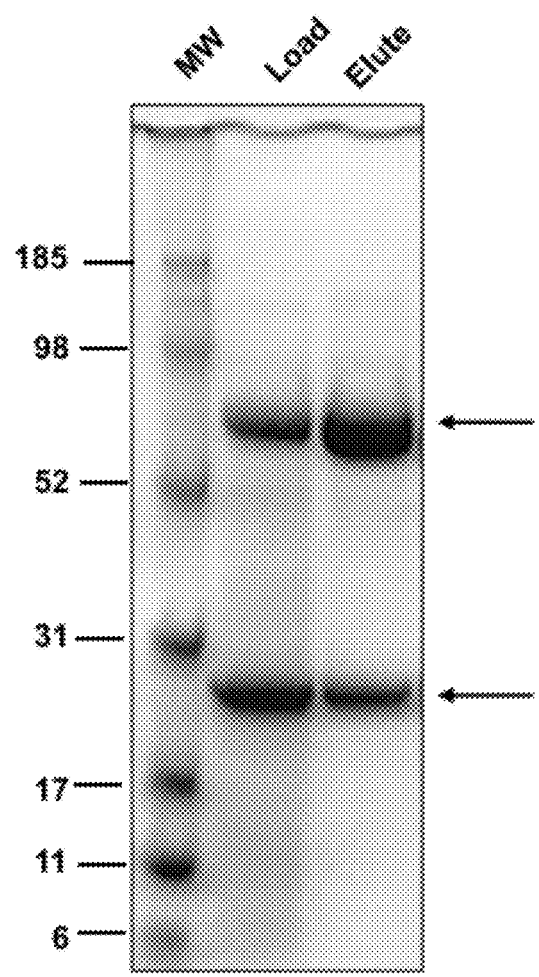
FIG. 19 shows a reducing SDS-PAGE gel of detergent-treated conditioned culture supernatant (CCS) applied to a protein A affinity chromatography column (Load) and the material collected from pooled fractions after elution by 3M $MgCl_2$ (Elute). Arrows point to the IgM heavy chain (~70 kD) and light chain (~25 kD).

Conditioned culture supernatant (CCS) was clarified by filtration through a 0.22 µm membrane filter. Detergent was added to the filtered CCS resulting in a solution containing 1% Triton® X-100 and 0.1% TNBP and incubated at 4° C. for more than 2 hours. Detergent-treated CCS was applied to an equilibrated CPG3000A protein A column and processed at a flow rate of 76 cm/h. After washing away unbound proteins with 10 column volumes of buffer A1, IgM was eluted from the column using a 5 mM sodium phosphate buffer supplemented with 3 M $MgCl_2$, pH 6.8 (buffer B). Remaining bound proteins were removed from the column by applying 3 column volumes of buffer A2 and 3 column volumes of buffer A3. To assess purity, a reducing SDS-PAGE gel comparing detergent-treated CCS applied to the protein A column (Load) and AB527 collected from pooled fractions after elution (Elute) was performed (FIG. 19—arrows point to the IgM µ chain (~70 kD) and light chain (~25 kD)). Protein A affinity chromatography allowed for recovery of ≧90% of input IgM, which is substantially free of contaminants.

TABLE 4

Dynamic binding capacity of IgM by CPG3000A protein A resin. Varying volumes of CCS containing AB527 were run through a 10 × 25 mm CPG3000A column at different linear flow rates. The concentration of AB527 loaded into the column and present in the flowthrough were measured by determining their relative concentrations as compared to that of a standard curve for known IgM standards determined on a protein A column (POROS A, Applied Biosystems), fitted on a HPLC system. The ratio of AB527 in each flowthrough to the amount of loaded antibody was computed for each injection to determine the dynamic binding capacity of the column at 5% and 10% IgM breakthrough.

| Linear Flow Rate (cm·hr⁻¹) | Dynamic Binding Capacity (DBC)[1] (mg AB527/L CPG3000A) | | AB527 in Flowthrough (FT) (mg) | |
|---|---|---|---|---|
| | 5% Breakthrough | 10% Breakthrough | 5% Breakthrough | 10% Breakthrough |
| 23 | 5780 | 6420 | 11559 | 12840 |
| 38 | 6869 | 7630 | 13737 | 15260 |
| 76 | 4395 | 5437 | 8789 | 10873 |
| 152 | 3126 | 3910 | 6252 | 7819 |

[1]DBC was determined on a 1.0 cm × 2.5 cm bed (2 ml bed volume)

EXAMPLE 8

Separation of IgM from Conditioned Culture Supernatant Contaminants by Cation Exchange Chromatography To remove contaminants, IgM suspended in buffer B was concentrated by diafiltration using a Prep/Scale-TFF 1 cartridge (Millipore) and a 10-fold volume of a buffer containing 10 mM sodium phosphate, 75 mM NaCl. Diafiltration was conducted at a flow rate of approximately 200 mL/minute, with inlet pressure kept at less than 20 PSI and permeate flow at approximately 60 mL/minute. A solution of 10% Triton® X-100 was added to the diafiltered sample to yield a 1% final concentration of Triton® X-100, and the sample was incubated at room temperature for 1 hour and filtered through a 0.2 µm membrane.

Figure 20:
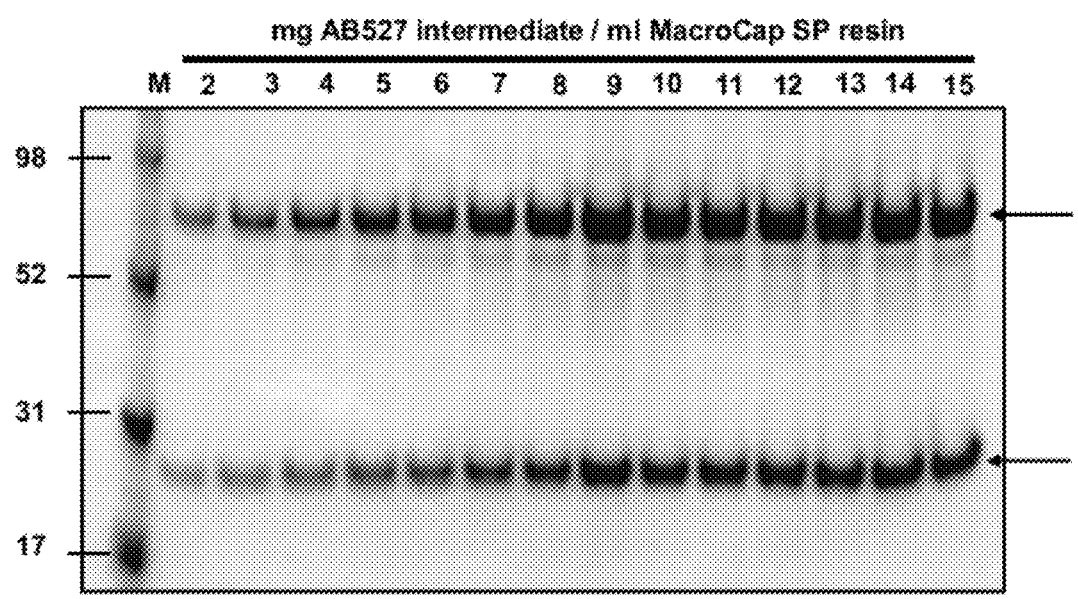
FIG. 20 shows a reducing SDS-PAGE gel of AB527 captured by differing amounts of MacroCap™ SP cation exchange resin. Arrows point to the IgM heavy chain (~70 kD) and light chain (~25 kD).

A cation exchange column was packed with MacroCap™ SP resin (GE Healthcare). The volume of resin used to capture IgM was estimated, with the understanding that 1 mL of resin binds approximately 9 mg of IgM at a flow rate of 76 cm/h (FIG. 20). Once the column was loaded with the desired amount of resin, it was connected to an FPLC apparatus and washed with 2 column volumes of purified water; 3 column volumes of 0.5 M NaOH (buffer A6), and 3 column volumes of 2 M NaCl. Before loading sample, the column was equilibrated with 5 column volumes of a buffer containing 10 mM sodium phosphate, 75 mM NaCl, 0.01% Tween®-80, pH 6.8 (buffer A4).

Figure 21:
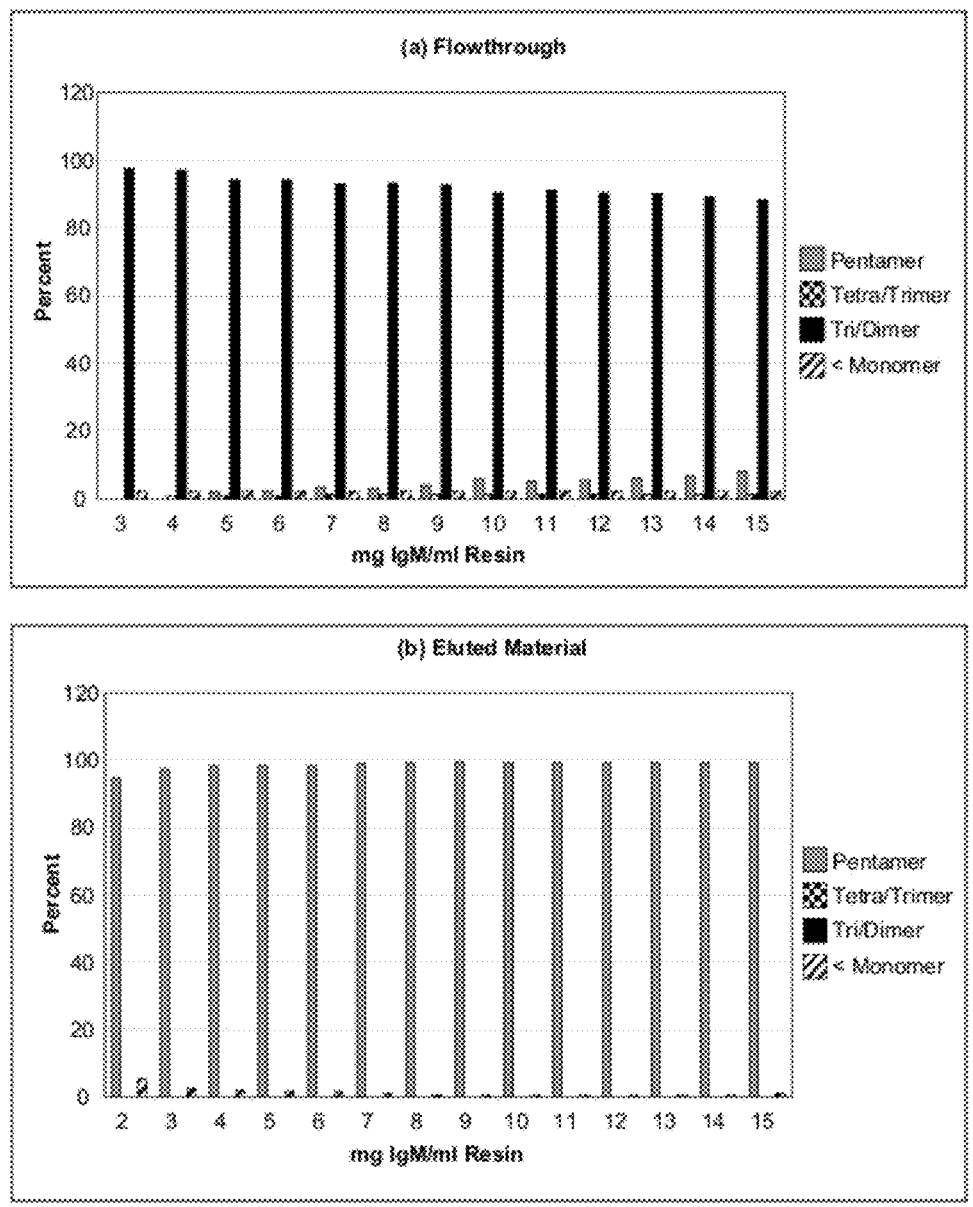
FIG. 21 shows relative amounts of various forms of AB527 IgM in the flowthrough (FIG. 21A) or eluate (FIG. 21B) collected after application of differing volumes of AB527 intermediate to MacroCap™ SP cation exchange resin.
Figure 22:
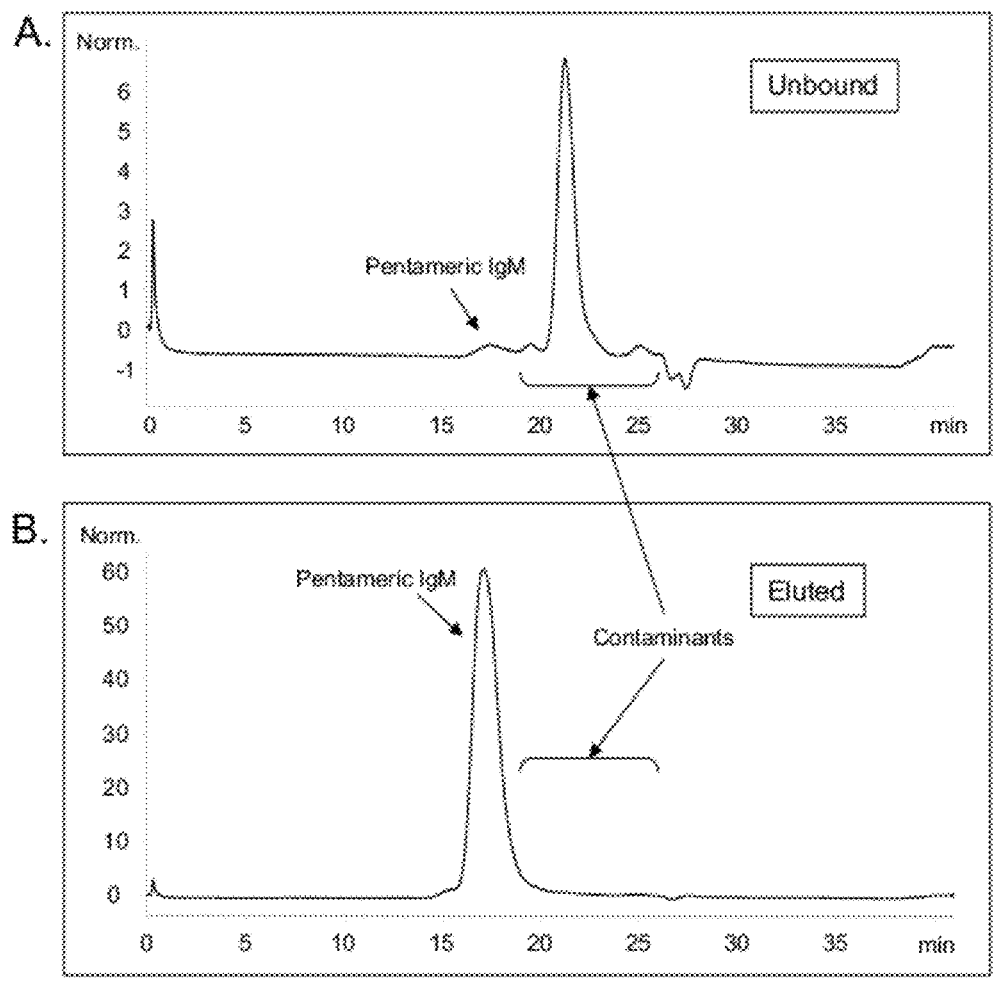
FIG. 22 depicts chromatograms from size exclusion-HPLC, verifying the size distribution of material present in the flowthrough (FIG. 22A) and elution (FIG. 22B) from the MacroCap™ SP column.

The diafiltered sample was applied to the column and processed at a flow rate of 76 cm/h. After washing away unbound proteins with 5 column volumes of buffer A4, IgM was eluted from the column using 4 column volumes of a 10 mM sodium phosphate buffer containing 200 mM NaCl and 0.01% Tween®-80, pH 6.8 (buffer C). Remaining bound proteins were removed from the column by applying 3 column volumes of buffer A6 and 3 column volumes of 2 M NaCl As shown in FIGS. 13A and B, the flowthrough material largely contained a mixture of IgM trimers and dimers (FIG. 21A); however, the eluted material was almost exclusively pentameric IgM (FIG. 21B). Cation exchange chromatography provides ≧95% yield of pentameric IgM that is substantially free of contaminants and incompletely assembled IgM (FIG. 22).

EXAMPLE 9

Separation of IgM from Conditioned Culture Supernatant Contaminants by Hydroxyapatite Chromatography The hydroxyapatite column was prepared using CHT® II Ceramic Hydroxyapatite, 80 µm bead size (Bio-Rad Laboratories, #157-8100). The volume of resin used to capture IgM was estimated, with the understanding that 1 mL of resin binds approximately 20 mg of IgM at a flow rate of 76 cm/h, and at this flow rate there is less than 5% loss of IgM in the column flow-through. The column was packed by hydrating the matrix with 200 mM potassium phosphate pH 9.0, using 0.54 g of dry matrix for each mL of desired column-bed volume. The hydrated matrix was added to the column, allowing it to settle before the resin was equilibrated with 5 column volumes of a buffer containing 10 mM sodium phosphate, 100 mM NaCl, 0.01% Tween®-80, pH 6.8 (buffer A8)

To reduce contaminants, IgM suspended in 10 mM sodium phosphate, 200 mM NaCl, 0.01% Tween®-80, pH 6.8 was diluted with an equivalent volume of 0.01% Tween®-80 and added to the equilibrated column. The IgM suspension was processed through the column at a flow rate of 76 cm/h. The column was washed with 10 column volumes of buffer A8, to remove unbound substances. Bound IgM was eluted with 4 column volumes of a 175 mM sodium phosphate buffer containing 100 mM NaCl and 0.01% Tween®-80, pH 6.8 (data not shown). Following elution, remaining bound proteins were removed from the column with a 500 mM sodium phosphate buffer containing 100 mM NaCl, pH 6.8. The resulting IgM solution was substantially free of contaminants. The solution eluted from the hydroxyapatite matrix, when preceded by protein A affinity chromatography and cation exchange chromatography, described herein, was over 99% pure as compared to the clarified cell culture supernatant.

EXAMPLE 10

Production of a Ganglioside-BSA Conjugates

A GD2-BSA conjugate was produced to provide an effective GD2 antigen to examine the specificity of GD2 specific antibodies by immunoassay. In addition, GM2-BSA and GM3-BSA conjugates were produced to serve as controls for GD2-BSA binding specificity. The covalent conjugates were prepared by site-specific reductive amination of the gangliosides by amines present on BSA, utilizing sodium cyanoborohydride as a mild reducing agent. Coupling is thought to occur mainly to terminal e-amino groups on the side chains of lysine residues present in BSA.

To prepare the conjugates, 400 µl of a 2 mg/ml solution of BSA dissolved in 0.05 M carbonate-bicarbonate buffer, pH 9.6, was combined with 500 µl of a 1 mg/ml solution of GD2 (Biodesign International, #A86168H), GM2 (Axxora, #ALX-302-005-M001), or GM3 (Axxora, #ALX-302-003-M002) dissolved in absolute ethanol; 2070 µl of 0.05 M carbonate-bicarbonate buffer, pH 9.6; and 30 µl of a 5 M sodium cyanoborohydride solution of 10 mM sodium hydroxide. The reaction mixture was incubated at 25° C. for two hours before adding 1200 µl of 1M ethanolamine, pH 8.0 and incubating at 25° C. for an additional 15 minutes. The reaction solution was placed in dialysis tubing (Pierce Biotechnology, #68100) and dialyzed twice in 1 L of a 50 mM sodium carbonate-bicarbonate solution, pH 9.6, at 2-8° C. for 6-18 hours.

EXAMPLE 11

AB527 Binds to BSA-Conjugated GD2

Figure 23:
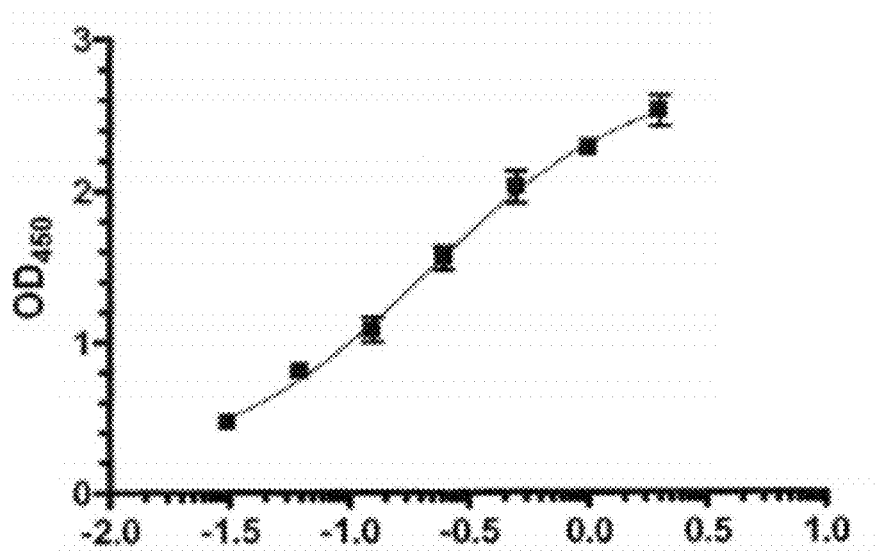
FIG. 23 provides a graphical representation of AB527 binding to the GD2-BSA conjugate.

Antigenicity of the GD2-BSA conjugate was assessed by ELISA. ELISA coating buffer was prepared by dissolving one carbonate/bicarbonate capsule (Sigma) in 100 mL ultrapure water. GD2-BSA conjugate was diluted to a concentration of 2 µg/ml, in ELISA coating buffer, and added to wells of a 96-well ELISA plate (Greiner Bio-One cat #655081). The plates were sealed and incubated at 2-8° C. for 16-24 hours. Following incubation, the coating buffer was removed from the wells and 0.3 mL/well of ELISA blocking solution (PBS supplemented with 2.5% BSA (w/v) and 0.05% Tween®-20) was added. Plates were incubated, while shaking on a microplate shaker, for 2 hours at 21-25° C. before adding AB527 antibody. Two-fold serial dilutions of AB527 (initial working concentration of 2 µg/ml) were added to the blocked ELISA plates and incubated with shaking on a microplate shaker at 21-25° C. for 1 hour. Plates were washed three times on the Dynex Ultrawash™ plate washer, using 0.3 mL/well ELISA wash buffer. Bound AB527 was detected with HRP-conjugated goat anti-human IgG+IgM (H+L), diluted 1:10,000 in ELISA blocking buffer. The HRP-conjugate was removed and wells were washed three times with 0.3 mL/well ELISA wash buffer. SureBlue™ TMB substrate (50 µl/well) was added to washed wells and plates were incubated at 21-25° C. for 15 minutes, before AB527 binding was assessed by light absorption (450 nm) (FIG. 23). Nonspecific absorption at 450 nm was determined to be 0.065 in the absence of AB527.

Figure 24:
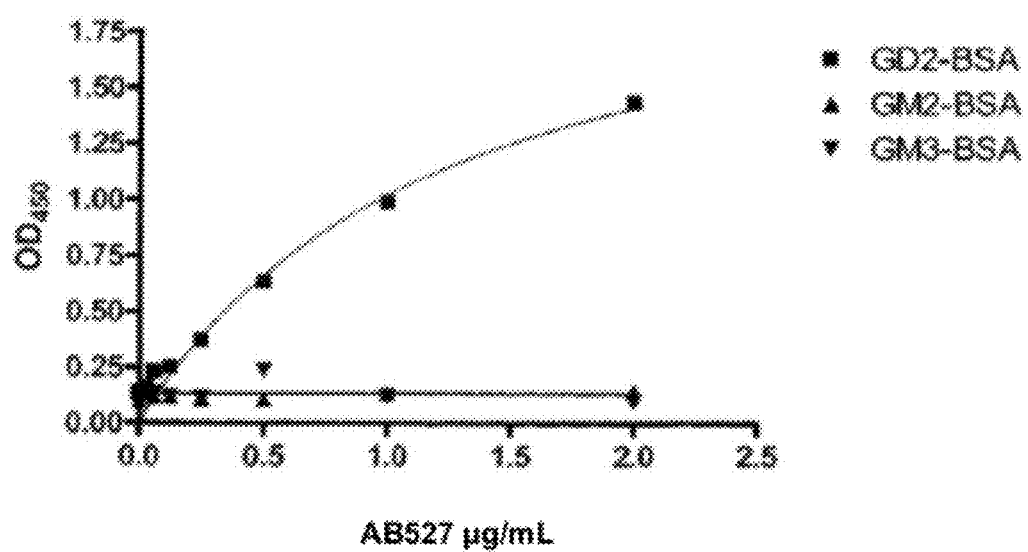
FIG. 24 provides a graphical representation comparing AB527 binding to GD2-BSA, GM2-BSA, and GM3-BSA conjugates.

In contrast to the GD2-BSA conjugate, AB527 did not recognize other ganglioside-BSA conjugates. The gangliosides GM2 and GM3 were conjugated to BSA, by the method described for GD2, and both were assessed, by ELISA, for the ability to elicit AB527 binding. As shown in FIG. 24, AB527 recognized only the GD2-BSA conjugate. It should be noted that a GM2-specific antibody was able to detect the GM2-BSA conjugate; however, an appropriate GM3-specific antibody was not available to assess the antigenic nature of the GM3-BSA conjugate (data not shown).

EXAMPLE 12

Effect of CMS on AB527-Expressing Cells Grown in GIBCO-CD CHO Complete Medium

Figure 26:
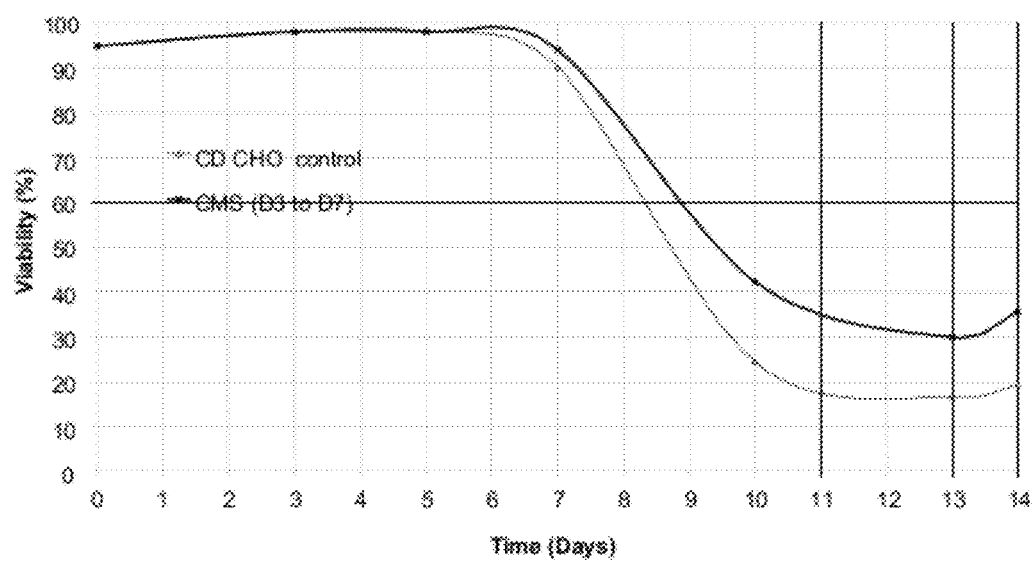
FIG. 26 shows the relative percentage of viable cells over time for AB527-expressing cells cultured in media with (CMS) and without (CD CHO control) the addition of an embodiment of the CMS.
Figure 27:
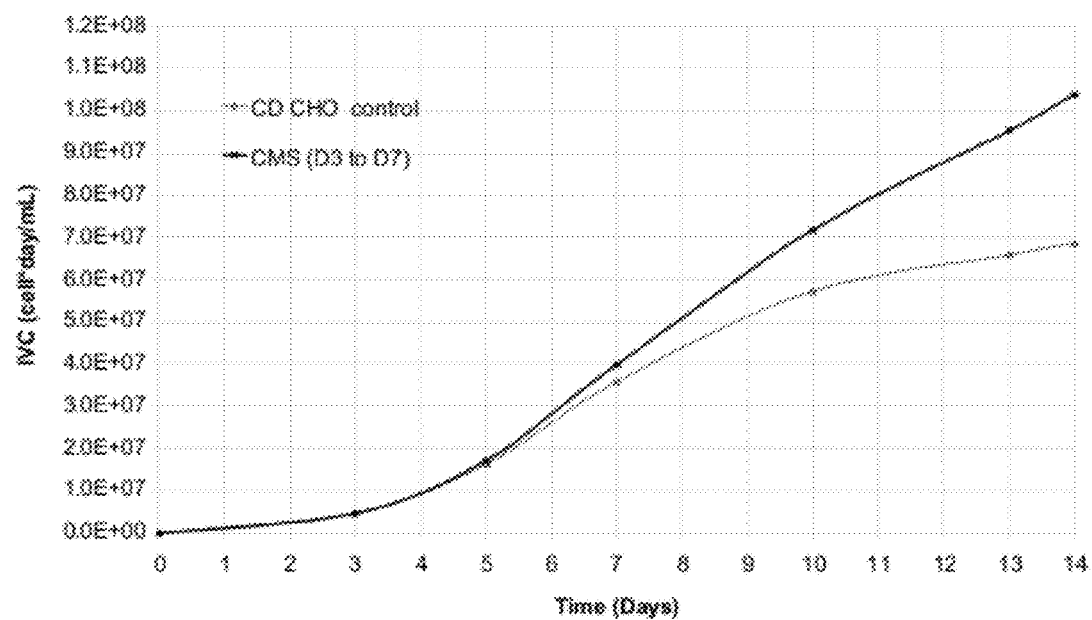
FIG. 27 shows the integral viable cell density (IVC) over time for AB527-expressing cells cultured in media with (CMS) and without (CD CHO control) the addition of an embodiment of the CMS.
Figure 28:
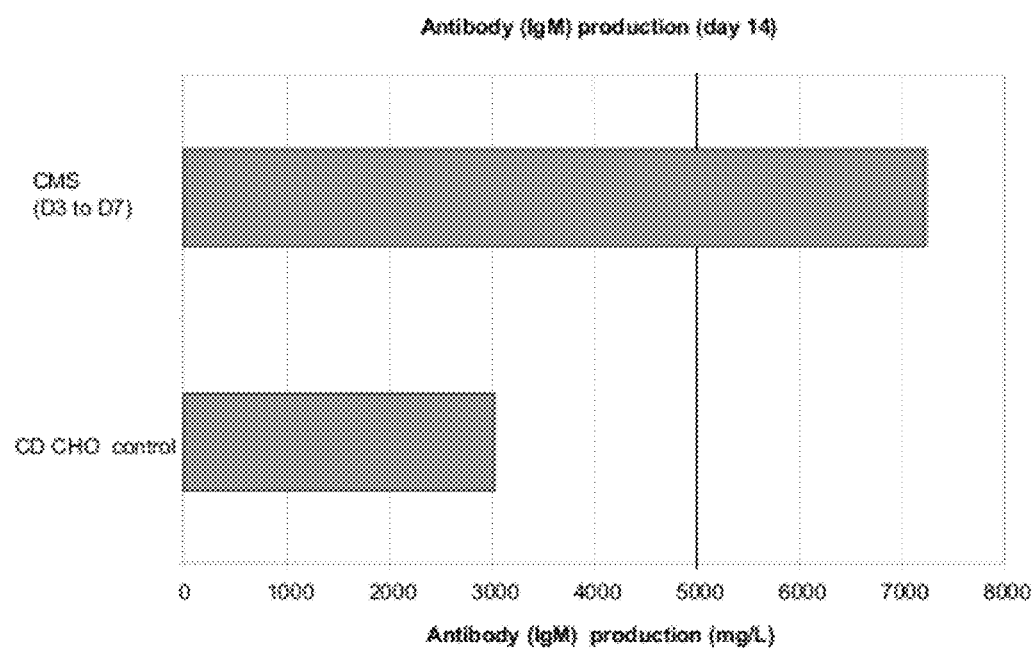
FIG. 28 shows the total antibody production, after 14 days in culture, for AB527-expressing cells cultured in media with (CMS) and without (CD CHO control) the addition of an embodiment of the CMS.

To determine the effect of culture media supplement (CMS) on cell growth and antibody production, cells were revived and cultured in a shake flask in 20 mL GIBCO-CD-CHO complete medium. All cultures were incubated in 125 mL shake flask at 37° C., 5% $CO_2$, 120 rpm. The seeding density was $3.5 \times 10^5$ cells/mL at >95% viability. Cells were cultured for 14 days in either CD-CHO media or in CD-CHO media supplemented on days 3-7 with 2% (vol/vol) CMS. Following addition of CMS on day 7 a total of 10% of the initial culture volume had been supplemented with CMS. Viable cell density (FIG. 25), percent viability (FIG. 26), and integral viable cell density (IVC) (FIG. 27) were determined using a CEDEX automated cell counter on days 0, 3, 5, 7, 10, 13, and 14. Antibody production was determined for each group of cultured cells on day 14 by protein A HPLC (FIG. 28).

Figure 25:
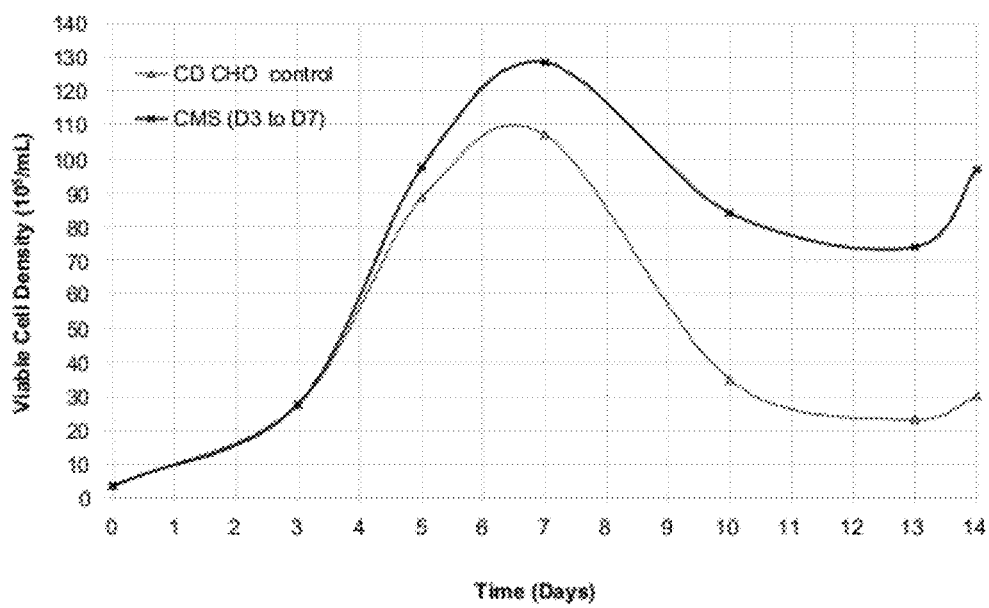
FIG. 25 shows a comparison of viable cell density over time for AB527-expressing cells cultured in media with (culture media supplement (CMS)) and without (CD CHO control) the addition of an embodiment of the CMS.

As shown in FIG. 25, cultured cells provided with 2% CMS from day 3 to day 7 achieved a maximum viable cell density of $12.8 \times 10^6$ cells/mL on day 7. The control cell culture, without CMS, reached a maximum cell density of $10.7 \times 10^6$ cells/mL on day 7. The use of CMS replenishes limiting medium components such as glucose, amino acids and vitamins and helps the culture reach a higher cell density. In both cell culture conditions, cells maintained a good viability (>90%) until day 7 (FIG. 26); however, cultured cells provided CMS from day 3 to day 7 demonstrated a better viability than the control culture after day 7. It is possible that some key nutrients were depleted in the control culture after day 7 while the CMS added back those key nutrients and helped the cell maintain a better viability.

On day 14, total antibody production was assessed for each culture. Cells cultured with CMS reached a maximum antibody titer of 7240 mg/L, much higher than that observed for the control culture (3036 mg/L) (FIG. 28). The higher antibody titer could be a result of a higher specific antibody production rate after the addition of the nutrients. Investigation of the cell growth and antibody production profiles for each growth condition demonstrated that the culture provided CMS achieved a 140% increase in antibody production (table 5). Even though the doubling time was the same for both cultures, the CMS did help cultures achieve a 50% improvement in IVC and another 50% increase in specific antibody production rate. The 50% improvement in IVC was due to a higher maximum cell density achieved in the culture with CMS. Since the final antibody titer is equal to the IVC multiple specific production rate, it suggested that both IVC and specific antibody production rate contributed to the 140% increase in antibody production in the cell culture with CMS. Table 5 summarizes the effects the CMS on AB527-expressing cells.

TABLE 5

Summary of the Effects of CMS on Cell Growth and Antibody Production of AB527-Expressing Cells.

| Culture Conditions | Maximum Viable Cell Density ($10^5$/mL) | Final Antibody Titer (mg/L) | Doubling Time (DT) | Integral of Viable Cell Density (IVC) (cell · day/mL) | Specific Antibody Production Rate (Qp) (mg/$10^9$ cells/day) |
|---|---|---|---|---|---|
| CD-CHO Control | 107.00 | 3036 | 24.17 | 6.85E+7 | 44.08 |
| CMS | 128.40 | 7239.9 | 24.17 | 1.04E+8 | 66.95 |

EXAMPLE 13

Effect of Valeric Acid on AB527-Expressing Cells Grown in GIBCO-CD CHO Complete Medium To determine the effect of valeric acid on cell growth, AB527-expressing cells were cultured in GIBCO-CD-CHO complete medium supplemented with valeric acid to a concentration of 0 mM, 1 mM, 2 mM, 4 mM, or 8 mM. Cells were cultured for 14 days and viable cell density, percent viability, and integral viable cell density were determined using a CEDEX automated cell counter on days 0, 3, 5, 7, 10, 13, and 14. Antibody production was determined for each group of cultured cells on day 14 by protein A HPLC.

Cells cultured without valeric acid achieved the maximum cell density of $10.8 \times 10^6$ cells/mL at day 7; however, cells cultured with valeric acid grew much slower as the concentration of valeric acid increased. For example, cells cultured in 8 mM valeric acid, reached a maximum cell density of $5.4 \times 10^6$ cells/mL at day 7, which is the lowest maximum cell density of all cultures. Cell viability studies demonstrated that cells cultured with valeric acid had lower viability before day 7, with the lowest viability at day 7 (67.4%) observed for cells cultured in 8 mM valeric acid. These results indicate that higher concentration of the valeric acid inhibited cell proliferation. After day 7, the viability of the control culture dropped much quicker; however, this was likely due to consumption of key nutrients since this cell culture had a much higher cell density than those cultured in valeric acid (table 6).

Unexpectedly, however, valeric acid had a positive effect on antibody production. All cells cultured in the presence of valeric acid, with exception of the highest concentration of 8 mM, had higher antibody titers than the control culture at day 14. Cell cultured in 1 mM valeric acid produced the highest antibody titer (4137 mg/L) at day 14, which is 36% higher than that of the control culture (3036 mg/L) (table 6).

Even though the valeric acid inhibited the cell growth, it did not demonstrate the significant negative effect on the integral of viable cell density, except at the highest concentration of 8 mM. The IVC values at day 14 were quite similar for the other four culture conditions. It is likely that the inhibition of valeric acid on the cell proliferation led to a slower consumption of the nutrients, thus avoiding late-stage nutrient-depleted media, which was encountered by the control culture.

In summary, the cell culture can achieve a better antibody production in presence of the valeric acid. The specific antibody production rate ranging from 52 to 58 mg/$10^9$ cells/day was observed in cultures with valeric acid (table 6), which are much higher than the value of 44 mg/$10^9$ cells/day observed for the control culture. Thus, the highest antibody production achieved by cells cultured in 1 mM valeric acid was mainly due to the increases in the specific antibody production (table 6).

TABLE 6

Summary of the Effects of Valeric Acid on Cell Growth and Antibody Production of AB527-Expressing Cells.

| Culture Conditions | Maximum Viable Cell Density ($10^5$/mL) | Final Antibody Titer (mg/L) | Doubling Time (DT) | Integral of Viable Cell Density (IVC) (cells · day/mL) | Specific Antibody Production Rate (Qp) (mg/$10^9$ cells/day) |
|---|---|---|---|---|---|
| CD-CHO Control | 107.00 | 3036 | 24.17 | 6.85E+7 | 44.08 |
| Valeric Acid (1 mM) | 94.60 | 4137.1 | 24.17 | 6.74E+7 | 58.44 |
| Valeric Acid (2 mM) | 81.00 | 3706.7 | 24.17 | 6.55E+7 | 54.45 |
| Valeric Acid (4 mM) | 77.40 | 3600.1 | 24.17 | 6.72E+7 | 52.24 |
| Valeric Acid (8 mM) | 54.40 | 2760.4 | 24.17 | 4.76E+7 | 56.16 |

What is claimed:

1. A recombinant pentameric IgM antibody that specifically binds human GD2 and has a heavy chain CDR1 comprising the amino acid sequence of SEQ ID NO:10, a heavy chain CDR2 comprising the amino acid sequence of SEQ ID NO:11, a heavy chain CDR3 comprising the amino acid sequence of SEQ ID NO:12, a light chain CDR1 comprising the amino acid sequence of SEQ ID NO:26, a light chain CDR2 comprising the amino acid sequence of SEQ ID NO:27, and a light chain CDR3 comprising the amino acid sequence of SEQ ID NO:28, wherein said antibody does not incorporate J-chain.

2. The antibody of claim 1, wherein said antibody comprises a heavy chain variable domain having the amino acid sequence of SEQ ID NO: 16 and a light chain variable domain having the amino acid sequence of SEQ ID NO: 32.

3. The antibody of claim 1, wherein said antibody comprises a heavy chain having the amino acid sequence of SEQ ID NO: 40 and a light chain having the amino acid sequence of SEQ ID NO: 42.

4. The antibody of claim 1, wherein said antibody mediates complement dependent cytotoxicity to a greater degree than an identical antibody that incorporates J-chain.

5. The antibody of claim 1, wherein the antibody exhibits a steady state dissociation constant ($K_d$) for human GD2 of about $4.5 \times 10^{-9}$ molar or less.

6. The antibody of claim 1, wherein the antibody is a human antibody.

* * * * *

SEQUENCE LISTING

<160> NUMBER OF SEQ ID NOS: 60

<210> SEQ ID NO 1
<211> LENGTH: 1767
<212> TYPE: DNA
<213> ORGANISM: Artificial Sequence
<220> FEATURE:
<223> OTHER INFORMATION: Synthetic construct

<400> SEQUENCE: 1

```
atgggatgga gctgtatcat cctcttcttg gtagcaacag ctacaggtgt acacagcgag      60
gtgcagctgg tggagtctgg gggaggcttg gtccagcctg ggggtccct gagactctcc     120
```

-continued

```
tgtgcagcct ctgggttcac cgtcagtggc agctacatga gctgggtccg ccaggctcca      180
gggaagggac tggagtgggt ctcagtcatt tatagcggtg gtagcacata ctacgcagac      240
tccgtgaagg gcagattcac catctccaga gacaattcga agaacaccct gtatcttcaa      300
atgaacagcc tgagagccga ggacacggct gtgtattact gtgcgagaga cctccgcggt      360
tcctatgact actggggcca gggaaccctg gtcatcgtct cctcagggag tgcatccgcc      420
ccaacccttt tcccctcgt ctcctgtgag aattccccgt cggatacgag cagcgtggcc       480
gttggctgcc tcgcacagga cttccttccc gactccatca ctttctcctg gaaatacaag      540
aacaactctg acatcagcag cacccggggc ttcccatcag tcctgagagg gggcaagtac      600
gcagccacct cacaggtgct gctgccttcc aaggacgtca tgcagggcac agacgaacac      660
gtggtgtgca aagtccagca ccccaacggc aacaaagaaa agaacgtgcc tcttccagtg      720
attgctgagc tgcctcccaa agtgagcgtc ttcgtcccac cccgcgacgg cttcttcggc      780 aaccccgca agtccaagct catctgccag gccacgggtt tcagtccccg gcagattcag       840
gtgtcctggc tgcgcgaggg gaagcaggtg gggtctggcg tcaccacgga ccaggtgcag      900
gctgaggcca aagagtctgg gcccacgacc tacaaggtga ccagcacact gaccatcaaa      960
gagagcgact ggctcagcca gagcatgttc acctgccgcg tggatcacag gggcctgacc     1020
ttccagcaga atgcgtcctc catgtgtgtc cccgatcaag acacagccat ccgggtcttc     1080
gccatccccc catcctttgc cagcatcttc ctcaccaagt ccaccaagtt gacctgcctg     1140
gtcacagacc tgaccaccta tgacagcgtg accatctcct ggaccccgca gaatggcgaa     1200
gctgtgaaaa cccacaccaa catctccgag agccaccccca atgccacttt cagcgccgtg     1260
ggtgaggcca gcatctgcga ggatgactgg aattccgggg agaggttcac gtgcaccgtg     1320
acccacacag acctgccctc gccactgaag cagaccatct cccggcccaa ggggtggcc      1380 ctgcacaggc ccgatgtcta cttgctgcca ccagcccggg agcagctgaa cctgcgggag     1440
tcggccacca tcacgtgcct ggtgacgggc ttctctcccg cggacgtctt cgtgcagtgg     1500
atgcagaggg ggcagccctt gtccccggag aagtatgtga ccagcgcccc aatgcctgag     1560
ccccaggccc caggccggta cttcgcccac agcatcctga ccgtgtccga agaggaatgg     1620
aacacggggg agacctacac ctgcgtggtg gcccatgagg ccctgcccaa cagggtcacc     1680
gagaggaccg tggacaagtc caccggtaaa cccaccctgt acaacgtgtc cctggtcatg     1740
tccgacacag ctggcacctg ctactga                                         1767
```

<210> SEQ ID NO 2
<211> LENGTH: 30
<212> TYPE: DNA
<213> ORGANISM: Homo sapiens

<400> SEQUENCE: 2

```
gggttcaccg tcagtggcag ctacatgagc                                         30
```

<210> SEQ ID NO 3
<211> LENGTH: 48
<212> TYPE: DNA
<213> ORGANISM: Homo sapiens

<400> SEQUENCE: 3

```
gtcatttata gcggtggtag cacatactac gcagactccg tgaagggc                     48
```

<210> SEQ ID NO 4
<211> LENGTH: 24

```
<212> TYPE: DNA
<213> ORGANISM: Homo sapiens

<400> SEQUENCE: 4
gacctccgcg gttcctatga ctac                                            24

<210> SEQ ID NO 5
<211> LENGTH: 75
<212> TYPE: DNA
<213> ORGANISM: Homo sapiens

<400> SEQUENCE: 5
gaggtgcagc tggtggagtc tgggggaggc ttggtccagc ctggggggtc cctgagactc      60
tcctgtgcag cctct                                                      75

<210> SEQ ID NO 6
<211> LENGTH: 42
<212> TYPE: DNA
<213> ORGANISM: Homo sapiens

<400> SEQUENCE: 6
tgggtccgcc aggctccagg gaagggactg gagtgggtct ca                         42

<210> SEQ ID NO 7
<211> LENGTH: 96
<212> TYPE: DNA
<213> ORGANISM: Homo sapiens

<400> SEQUENCE: 7
agattcacca tctccagaga caattcgaag aacaccctgt atcttcaaat gaacagcctg      60
agagccgagg acacggctgt gtattactgt gcgaga                                96

<210> SEQ ID NO 8
<211> LENGTH: 315
<212> TYPE: DNA
<213> ORGANISM: Homo sapiens

<400> SEQUENCE: 8
gaggtgcagc tggtggagtc tgggggaggc ttggtccagc ctggggggtc cctgagactc      60
tcctgtgcag cctctgggtt caccgtcagt ggcagctaca tgagctgggt ccgccaggct     120
ccagggaagg gactggagtg gtctcagtc atttatagcg gtggtagcac atactacgca      180
gactccgtga aggcagatt caccatctcc agagacaatt cgaagaacac cctgtatctt     240
caaatgaaca gcctgagagc cgaggacacg gctgtgtatt actgtgcgag agacctccgc     300
ggttcctatg actac                                                     315

<210> SEQ ID NO 9
<211> LENGTH: 588
<212> TYPE: PRT
<213> ORGANISM: Artificial Sequence
<220> FEATURE:
<223> OTHER INFORMATION: Synthetic construct

<400> SEQUENCE: 9

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Val
        35                  40                  45
```

-continued

Ser Gly Ser Tyr Met Ser Trp Val Arg Gln Ala Pro Gly Lys Gly Leu
            50                  55                  60

Glu Trp Val Ser Val Ile Tyr Ser Gly Gly Ser Thr Tyr Tyr Ala Asp
 65                      70                  75                  80

Ser Val Lys Gly Arg Phe Thr Ile Ser Arg Asp Asn Ser Lys Asn Thr
                    85                  90                  95

Leu Tyr Leu Gln Met Asn Ser Leu Arg Ala Glu Asp Thr Ala Val Tyr
                100                 105                 110

Tyr Cys Ala Arg Asp Leu Arg Gly Ser Tyr Asp Tyr Trp Gly Gln Gly
            115                 120                 125

Thr Leu Val Ile Val Ser Ser Ala Ser Ala Pro Thr Leu Phe
            130                 135                 140

Pro Leu Val Ser Cys Glu Asn Ser Pro Ser Asp Thr Ser Ser Val Ala
145                 150                 155                 160

Val Gly Cys Leu Ala Gln Asp Phe Leu Pro Asp Ser Ile Thr Phe Ser
                165                 170                 175

Trp Lys Tyr Lys Asn Asn Ser Asp Ile Ser Ser Thr Arg Gly Phe Pro
                180                 185                 190

Ser Val Leu Arg Gly Gly Lys Tyr Ala Ala Thr Ser Gln Val Leu Leu
            195                 200                 205

Pro Ser Lys Asp Val Met Gln Gly Thr Asp Glu His Val Val Cys Lys
            210                 215                 220

Val Gln His Pro Asn Gly Asn Lys Glu Lys Asn Val Pro Leu Pro Val
225                 230                 235                 240

Ile Ala Glu Leu Pro Pro Lys Val Ser Val Phe Val Pro Pro Arg Asp
                245                 250                 255

Gly Phe Phe Gly Asn Pro Arg Lys Ser Lys Leu Ile Cys Gln Ala Thr
                260                 265                 270

Gly Phe Ser Pro Arg Gln Ile Gln Val Ser Trp Leu Arg Glu Gly Lys
            275                 280                 285

Gln Val Gly Ser Gly Val Thr Thr Asp Gln Val Gln Ala Glu Ala Lys
            290                 295                 300

Glu Ser Gly Pro Thr Thr Tyr Lys Val Thr Ser Thr Leu Thr Ile Lys
305                 310                 315                 320

Glu Ser Asp Trp Leu Ser Gln Ser Met Phe Thr Cys Arg Val Asp His
                325                 330                 335

Arg Gly Leu Thr Phe Gln Gln Asn Ala Ser Ser Met Cys Val Pro Asp
                340                 345                 350

Gln Asp Thr Ala Ile Arg Val Phe Ala Ile Pro Pro Ser Phe Ala Ser
            355                 360                 365

Ile Phe Leu Thr Lys Ser Thr Lys Leu Thr Cys Leu Val Thr Asp Leu
            370                 375                 380

Thr Thr Tyr Asp Ser Val Thr Ile Ser Trp Thr Arg Gln Asn Gly Glu
385                 390                 395                 400

Ala Val Lys Thr His Thr Asn Ile Ser Glu Ser His Pro Asn Ala Thr
                405                 410                 415

Phe Ser Ala Val Gly Glu Ala Ser Ile Cys Glu Asp Asp Trp Asn Ser
            420                 425                 430

Gly Glu Arg Phe Thr Cys Thr Val Thr His Thr Asp Leu Pro Ser Pro
            435                 440                 445

Leu Lys Gln Thr Ile Ser Arg Pro Lys Gly Val Ala Leu His Arg Pro
            450                 455                 460

Asp Val Tyr Leu Leu Pro Pro Ala Arg Glu Gln Leu Asn Leu Arg Glu
465                 470                 475                 480

```
Ser Ala Thr Ile Thr Cys Leu Val Thr Gly Phe Ser Pro Ala Asp Val
            485                 490                 495

Phe Val Gln Trp Met Gln Arg Gly Gln Pro Leu Ser Pro Glu Lys Tyr
        500                 505                 510

Val Thr Ser Ala Pro Met Pro Glu Pro Gln Ala Pro Gly Arg Tyr Phe
        515                 520                 525

Ala His Ser Ile Leu Thr Val Ser Glu Glu Trp Asn Thr Gly Glu
    530                 535                 540

Thr Tyr Thr Cys Val Val Ala His Glu Ala Leu Pro Asn Arg Val Thr
545                 550                 555                 560

Glu Arg Thr Val Asp Lys Ser Thr Gly Lys Pro Thr Leu Tyr Asn Val
                565                 570                 575

Ser Leu Val Met Ser Asp Thr Ala Gly Thr Cys Tyr
            580                 585

<210> SEQ ID NO 10
<211> LENGTH: 10
<212> TYPE: PRT
<213> ORGANISM: Homo sapiens

<400> SEQUENCE: 10

Gly Phe Thr Val Ser Gly Ser Tyr Met Ser
1               5                   10

<210> SEQ ID NO 11
<211> LENGTH: 16
<212> TYPE: PRT
<213> ORGANISM: Homo sapiens

<400> SEQUENCE: 11

Val Ile Tyr Ser Gly Gly Ser Thr Tyr Tyr Ala Asp Ser Val Lys Gly
1               5                   10                  15

<210> SEQ ID NO 12
<211> LENGTH: 8
<212> TYPE: PRT
<213> ORGANISM: Homo sapiens

<400> SEQUENCE: 12

Asp Leu Arg Gly Ser Tyr Asp Tyr
1               5

<210> SEQ ID NO 13
<211> LENGTH: 25
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 14
<211> LENGTH: 14
<212> TYPE: PRT
<213> ORGANISM: Homo sapiens

<400> SEQUENCE: 14

Trp Val Arg Gln Ala Pro Gly Lys Gly Leu Glu Trp Val Ser
1               5                   10
```

<210> SEQ ID NO 15
<211> LENGTH: 32
<212> TYPE: PRT
<213> ORGANISM: Homo sapiens

<400> SEQUENCE: 15

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 16
<211> LENGTH: 105
<212> TYPE: PRT
<213> ORGANISM: Homo sapiens

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Ser
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Arg Gly Ser Tyr Asp Tyr
            100                 105

<210> SEQ ID NO 17
<211> LENGTH: 717
<212> TYPE: DNA
<213> ORGANISM: Artificial Sequence
<220> FEATURE:
<223> OTHER INFORMATION: Synthetic construct

<400> SEQUENCE: 17
atgggatgga gctgtatcat cctcttcttg gtagcaacag ctacaggtgt acacagcgaa      60
attgtgctga ctcagtctcc actctccctg cccgtcaccc ttggacagcc ggcctccatc    120
tcctgcaggt ctagtcaaag cctcgtatac agtgatggaa acacctactt gaattggttt    180
cagcagaggc caggccaatc tccaaggcgc ctaatttata aggtttctaa ccgggactct    240
ggggtcccag acagattcag cggcagtggg tcaggcactg atttcacact gaaaatcagc    300
agggtggagg ctgaggatgt tggggtttat tactgcatgc aagtacaca ctggccgcgg    360 acgttcggcc aagggaccaa ggtggaaatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca caggggaga gtgttaa        717

<210> SEQ ID NO 18
<211> LENGTH: 48

```
<212> TYPE: DNA
<213> ORGANISM: Homo sapiens

<400> SEQUENCE: 18
aggtctagtc aaagcctcgt atacagtgat ggaaacacct acttgaat        48

<210> SEQ ID NO 19
<211> LENGTH: 21
<212> TYPE: DNA
<213> ORGANISM: Homo sapiens

<400> SEQUENCE: 19
aaggtttcta accgggactc t                                      21

<210> SEQ ID NO 20
<211> LENGTH: 27
<212> TYPE: DNA
<213> ORGANISM: Homo sapiens

<400> SEQUENCE: 20
atgcaaggta cacactggcc gcggacg                                27

<210> SEQ ID NO 21
<211> LENGTH: 69
<212> TYPE: DNA
<213> ORGANISM: Homo sapiens

<400> SEQUENCE: 21
gaaattgtgc tgactcagtc tccactctcc ctgcccgtca cccttggaca gccggcctcc    60
atctcctgc                                                            69

<210> SEQ ID NO 22
<211> LENGTH: 45
<212> TYPE: DNA
<213> ORGANISM: Homo sapiens

<400> SEQUENCE: 22
tggtttcagc agaggccagg ccaatctcca aggcgcctaa tttat           45

<210> SEQ ID NO 23
<211> LENGTH: 96
<212> TYPE: DNA
<213> ORGANISM: Homo sapiens

<400> SEQUENCE: 23
ggggtcccag acagattcag cggcagtggg tcaggcactg atttcacact gaaaatcagc    60
agggtggagg ctgaggatgt tggggtttat tactgc                              96

<210> SEQ ID NO 24
<211> LENGTH: 306
<212> TYPE: DNA
<213> ORGANISM: Homo sapiens

<400> SEQUENCE: 24
gaaattgtgc tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
cggacg                                                              306
```

<210> SEQ ID NO 25
<211> LENGTH: 238
<212> TYPE: PRT
<213> ORGANISM: Artificial Sequence
<220> FEATURE:
<223> OTHER INFORMATION: Synthetic construct

<400> SEQUENCE: 25

Met Gly Trp Ser Cys Ile Ile Leu Phe Leu Val Ala Thr Ala Thr Gly
1               5                   10                  15

Val His Ser Glu Ile Val Leu Thr Gln Ser Pro Leu Ser Leu Pro Val
            20                  25                  30

Thr Leu Gly Gln Pro Ala Ser Ile Ser Cys Arg Ser Ser Gln Ser Leu
        35                  40                  45

Val Tyr Ser Asp Gly Asn Thr Tyr Leu Asn Trp Phe Gln Gln Arg Pro
    50                  55                  60

Gly Gln Ser Pro Arg Arg Leu Ile Tyr Lys Val Ser Asn Arg Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Met Gln Gly Thr His Trp Pro Arg Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 26
<211> LENGTH: 16
<212> TYPE: PRT
<213> ORGANISM: Homo sapiens

<400> SEQUENCE: 26

Arg Ser Ser Gln Ser Leu Val Tyr Ser Asp Gly Asn Thr Tyr Leu Asn
1               5                   10                  15

<210> SEQ ID NO 27
<211> LENGTH: 7
<212> TYPE: PRT
<213> ORGANISM: Homo sapiens

<400> SEQUENCE: 27

Lys Val Ser Asn Arg Asp Ser
1               5

<210> SEQ ID NO 28

-continued

```
<211> LENGTH: 9
<212> TYPE: PRT
<213> ORGANISM: Homo sapiens

<400> SEQUENCE: 28

Met Gln Gly Thr His Trp Pro Arg Thr
1               5

<210> SEQ ID NO 29
<211> LENGTH: 23
<212> TYPE: PRT
<213> ORGANISM: Homo sapiens

<400> SEQUENCE: 29

Glu Ile Val Leu Thr Gln Ser Pro Leu Ser Leu Pro Val Thr Leu Gly
1               5                   10                  15

Gln Pro Ala Ser Ile Ser Cys
            20

<210> SEQ ID NO 30
<211> LENGTH: 15
<212> TYPE: PRT
<213> ORGANISM: Homo sapiens

<400> SEQUENCE: 30

Trp Phe Gln Gln Arg Pro Gly Gln Ser Pro Arg Arg Leu Ile Tyr
1               5                   10                  15

<210> SEQ ID NO 31
<211> LENGTH: 32
<212> TYPE: PRT
<213> ORGANISM: Homo sapiens

<400> SEQUENCE: 31

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 32
<211> LENGTH: 102
<212> TYPE: PRT
<213> ORGANISM: Homo sapiens

<400> SEQUENCE: 32

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr
            100

<210> SEQ ID NO 33
<211> LENGTH: 103
```

```
<212> TYPE: DNA
<213> ORGANISM: Artificial Sequence
<220> FEATURE:
<223> OTHER INFORMATION: Oligonucleotide primer

<400> SEQUENCE: 33
gatcggatcc aagcttgccg ccaccatggg atggagctgt atcatcctct tcttggtagc        60
aacagctaca ggtgtacaca gcgaggtgca gctggtggag tct                        103

<210> SEQ ID NO 34
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 34
gggaagctta ccatgaagag gcccaggagt ccccccgggg gtcagggtga tggaggcagg        60

<210> SEQ ID NO 35
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 35
gatcaattgt cagtagcagg tgccagctgt gtcggacatg accag                       45

<210> SEQ ID NO 36
<211> LENGTH: 80
<212> TYPE: DNA
<213> ORGANISM: Artificial Sequence
<220> FEATURE:
<223> OTHER INFORMATION: Oligonucleotide primer

<400> SEQUENCE: 36
gatcggatcc gccgccacca tgggatggag ctgtatcatc ctcttcttgg tagcaacagc        60
tacaggtgta cacagcgaaa                                                    80

<210> SEQ ID NO 37
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 37
gggaagctta ccatgaagag gcccaggagt ccccccgggg gtcagggtga tggaggcagg        60

<210> SEQ ID NO 38
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 38
gatcgaattc ttaacactct cccctgttga ag                                      32

<210> SEQ ID NO 39
<211> LENGTH: 1710
<212> TYPE: DNA
<213> ORGANISM: Homo sapiens

<400> SEQUENCE: 39
```

```
gaggtgcagc tggtggagtc tgggggaggc ttggtccagc ctgggggtc cctgagactc      60
tcctgtgcag cctctgggtt caccgtcagt ggcagctaca tgagctgggt ccgccaggct    120
ccagggaagg gactggagtg gtctcagtc atttatagcg gtggtagcac atactacgca    180
gactccgtga agggcagatt caccatctcc agagacaatt cgaagaacac cctgtatctt    240
caaatgaaca gcctgagagc cgaggacacg gctgtgtatt actgtgcgag agacctccgc    300
ggttcctatg actactgggg ccagggaacc ctggtcatcg tctcctcagg gagtgcatcc    360
gccccaaccc tttccccct cgtctcctgt gagaattccc cgtcggatac gagcagcgtg    420
gccgttggct gcctcgcaca ggacttcctt cccgactcca tcactttctc ctggaaatac    480
aagaacaact ctgacatcag cagcacccgg ggcttcccat cagtcctgag aggggggcaag    540
tacgcagcca cctcacaggt gctgctgcct tccaaggacg tcatgcaggg cacagacgaa    600
cacgtggtgt gcaaagtcca gcaccccaac ggcaacaaag aaaagaacgt gcctcttcca    660
gtgattgctg agctgcctcc caaagtgagc gtcttcgtcc caccccgcga cggcttcttc    720
ggcaacccccc gcaagtccaa gctcatctgc caggccacgg gtttcagtcc ccggcagatt    780
caggtgtcct ggctgcgcga ggggaagcag gtggggtctg gcgtcaccac ggaccaggtg    840
caggctgagg ccaaagagtc tgggcccacg acctacaagg tgaccagcac actgaccatc    900
aaagagagcg actggctcag ccagagcatg ttcacctgcc gcgtggatca cgggggcctg    960
accttccagc agaatgcgtc ctccatgtgt gtccccgatc aagacacagc catccgggtc   1020
ttcgccatcc ccccatcctt tgccagcatc ttcctcacca agtccaccaa gttgacctgc   1080
ctggtcacag acctgaccac ctatgacagc gtgaccatct cctggaccg ccagaatggc   1140
gaagctgtga aacccacac caacatctcc gagagccacc ccaatgccac tttcagcgcc   1200
gtgggtgagg ccagcatctg cgaggatgac tggaattccg gggagaggtt cacgtgcacc   1260
gtgacccaca cagacctgcc ctcgccactg aagcagacca tctcccggcc caaggggggtg   1320
gccctgcaca ggcccgatgt ctacttgctg ccaccagccc gggagcagct gaacctgcgg   1380
gagtcggcca ccatcacgtg cctggtgacg ggcttctctc ccgcggacgt cttcgtgcag   1440
tggatgcaga gggggcagcc cttgtccccg gagaagtatg tgaccagcgc cccaatgcct   1500
gagccccagg ccccaggccg gtacttcgcc cacagcatcc tgaccgtgtc cgaagaggaa   1560
tggaacacgg gggagaccta cacctgcgtg gtggcccatg aggccctgcc caacagggtc   1620
accgagagga ccgtggacaa gtccaccggt aaacccaccc tgtacaacgt gtccctggtc   1680
atgtccgaca cagctggcac tgctactga                                    1710
```

<210> SEQ ID NO 40
<211> LENGTH: 569
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Ser
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu

```
                 65                  70                  75                  80
Gln Met Asn Ser Leu Arg Ala Glu Asp Thr Ala Val Tyr Tyr Cys Ala
                 85                  90                  95

Arg Asp Leu Arg Gly Ser Tyr Asp Tyr Trp Gly Gln Gly Thr Leu Val
                100                 105                 110

Ile Val Ser Ser Gly Ser Ala Ser Ala Pro Thr Leu Phe Pro Leu Val
                115                 120                 125

Ser Cys Glu Asn Ser Pro Ser Asp Thr Ser Val Ala Val Gly Cys
        130                 135                 140

Leu Ala Gln Asp Phe Leu Pro Asp Ser Ile Thr Phe Ser Trp Lys Tyr
145                 150                 155                 160

Lys Asn Asn Ser Asp Ile Ser Ser Thr Arg Gly Phe Pro Ser Val Leu
                165                 170                 175

Arg Gly Gly Lys Tyr Ala Ala Thr Ser Gln Val Leu Leu Pro Ser Lys
                180                 185                 190

Asp Val Met Gln Gly Thr Asp Glu His Val Val Cys Lys Val Gln His
                195                 200                 205

Pro Asn Gly Asn Lys Glu Lys Asn Val Pro Leu Pro Val Ile Ala Glu
        210                 215                 220

Leu Pro Pro Lys Val Ser Val Phe Val Pro Pro Arg Asp Gly Phe Phe
225                 230                 235                 240

Gly Asn Pro Arg Lys Ser Lys Leu Ile Cys Gln Ala Thr Gly Phe Ser
                245                 250                 255

Pro Arg Gln Ile Gln Val Ser Trp Leu Arg Glu Gly Lys Gln Val Gly
                260                 265                 270

Ser Gly Val Thr Thr Asp Gln Val Gln Ala Glu Ala Lys Glu Ser Gly
                275                 280                 285

Pro Thr Thr Tyr Lys Val Thr Ser Thr Leu Thr Ile Lys Glu Ser Asp
        290                 295                 300

Trp Leu Ser Gln Ser Met Phe Thr Cys Arg Val Asp His Arg Gly Leu
305                 310                 315                 320

Thr Phe Gln Gln Asn Ala Ser Ser Met Cys Val Pro Asp Gln Asp Thr
                325                 330                 335

Ala Ile Arg Val Phe Ala Ile Pro Pro Ser Phe Ala Ser Ile Phe Leu
                340                 345                 350

Thr Lys Ser Thr Lys Leu Thr Cys Leu Val Thr Asp Leu Thr Thr Tyr
                355                 360                 365

Asp Ser Val Thr Ile Ser Trp Thr Arg Gln Asn Gly Glu Ala Val Lys
        370                 375                 380

Thr His Thr Asn Ile Ser Glu Ser His Pro Asn Ala Thr Phe Ser Ala
385                 390                 395                 400

Val Gly Glu Ala Ser Ile Cys Glu Asp Asp Trp Asn Ser Gly Glu Arg
                405                 410                 415

Phe Thr Cys Thr Val Thr His Thr Asp Leu Pro Ser Pro Leu Lys Gln
                420                 425                 430

Thr Ile Ser Arg Pro Lys Gly Val Ala Leu His Arg Pro Asp Val Tyr
                435                 440                 445

Leu Leu Pro Pro Ala Arg Glu Gln Leu Asn Leu Arg Glu Ser Ala Thr
        450                 455                 460

Ile Thr Cys Leu Val Thr Gly Phe Ser Pro Ala Asp Val Phe Val Gln
465                 470                 475                 480

Trp Met Gln Arg Gly Gln Pro Leu Ser Pro Glu Lys Tyr Val Thr Ser
                485                 490                 495
```

```
Ala Pro Met Pro Glu Pro Gln Ala Pro Gly Arg Tyr Phe Ala His Ser
            500                 505                 510

Ile Leu Thr Val Ser Glu Glu Trp Asn Thr Gly Glu Thr Tyr Thr
        515                 520                 525

Cys Val Val Ala His Glu Ala Leu Pro Asn Arg Val Thr Glu Arg Thr
530                 535                 540

Val Asp Lys Ser Thr Gly Lys Pro Thr Leu Tyr Asn Val Ser Leu Val
545                 550                 555                 560

Met Ser Asp Thr Ala Gly Thr Cys Tyr
                565

<210> SEQ ID NO 41
<211> LENGTH: 660
<212> TYPE: DNA
<213> ORGANISM: Homo sapiens

<400> SEQUENCE: 41
gaaattgtgc tgactcagtc tccactctcc ctgcccgtca cccttggaca gccggcctcc      60
atctcctgca ggtctagtca aagcctcgta tacagtgatg aaacaccta cttgaattgg     120 tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttggggtt attactgca tgcaaggtac acactggccg     300
cggacgttcg gccaagggac caaggtggaa atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttaa     660

<210> SEQ ID NO 42
<211> LENGTH: 219
<212> TYPE: PRT
<213> ORGANISM: Homo sapiens

<400> SEQUENCE: 42

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

-continued

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 43
<211> LENGTH: 57
<212> TYPE: DNA
<213> ORGANISM: Homo sapiens

<400> SEQUENCE: 43
atgggatgga gctgtatcat cctcttcttg gtagcaacag ctacaggtgt acacagc    57

<210> SEQ ID NO 44
<211> LENGTH: 19
<212> TYPE: PRT
<213> ORGANISM: Homo sapiens

<400> SEQUENCE: 44

Met Gly Trp Ser Cys Ile Ile Leu Phe Leu Val Ala Thr Ala Thr Gly
1               5                   10                  15

Val His Ser

<210> SEQ ID NO 45
<211> LENGTH: 24
<212> TYPE: DNA
<213> ORGANISM: Epstein-Barr Virus

<400> SEQUENCE: 45
agcatgcctg aactaagtcc agtc    24

<210> SEQ ID NO 46
<211> LENGTH: 24
<212> TYPE: DNA
<213> ORGANISM: Epstein-Barr Virus

<400> SEQUENCE: 46
tttactgggt ccctccacat aatc    24

<210> SEQ ID NO 47
<211> LENGTH: 24
<212> TYPE: DNA
<213> ORGANISM: Epstein-Barr Virus

<400> SEQUENCE: 47
ttctactagg aaacggcgag cagg    24

<210> SEQ ID NO 48
<211> LENGTH: 22
<212> TYPE: DNA
<213> ORGANISM: Epstein-Barr Virus

<400> SEQUENCE: 48
ccggggtgct ggcgtctcat aa    22

<210> SEQ ID NO 49

```
<211> LENGTH: 21
<212> TYPE: DNA
<213> ORGANISM: Epstein-Barr Virus

<400> SEQUENCE: 49
ctgattgctg agaacctgct g                                              21

<210> SEQ ID NO 50
<211> LENGTH: 22
<212> TYPE: DNA
<213> ORGANISM: Epstein-Barr Virus

<400> SEQUENCE: 50
ctcccttgag cgtggcgttg at                                             22

<210> SEQ ID NO 51
<211> LENGTH: 21
<212> TYPE: DNA
<213> ORGANISM: Epstein-Barr Virus

<400> SEQUENCE: 51
aggtcgtgtt ccatcctcag g                                              21

<210> SEQ ID NO 52
<211> LENGTH: 22
<212> TYPE: DNA
<213> ORGANISM: Epstein-Barr Virus

<400> SEQUENCE: 52
tgccccagca agccgcagcg ac                                             22

<210> SEQ ID NO 53
<211> LENGTH: 21
<212> TYPE: DNA
<213> ORGANISM: Epstein-Barr Virus

<400> SEQUENCE: 53
gggcagtgtg tcaggagcaa g                                              21

<210> SEQ ID NO 54
<211> LENGTH: 22
<212> TYPE: DNA
<213> ORGANISM: Epstein-Barr Virus

<400> SEQUENCE: 54
actttccgcg cctgcctcat ga                                             22

<210> SEQ ID NO 55
<211> LENGTH: 20
<212> TYPE: DNA
<213> ORGANISM: Epstein-Barr Virus

<400> SEQUENCE: 55
ttcacctgtc ttggtccctg                                                20

<210> SEQ ID NO 56
<211> LENGTH: 20
<212> TYPE: DNA
<213> ORGANISM: Epstein-Barr Virus

<400> SEQUENCE: 56
gtaaaagggt cctaaggaac                                                20

<210> SEQ ID NO 57
```

```
<211> LENGTH: 20
<212> TYPE: DNA
<213> ORGANISM: Homo sapiens

<400> SEQUENCE: 57
cctcaccatt gagaaccaga                                               20

<210> SEQ ID NO 58
<211> LENGTH: 21
<212> TYPE: DNA
<213> ORGANISM: Homo sapiens

<400> SEQUENCE: 58
tgtagcactg tcttcatcac a                                             21

<210> SEQ ID NO 59
<211> LENGTH: 20
<212> TYPE: DNA
<213> ORGANISM: Murine

<400> SEQUENCE: 59
cctccccact gagaaggaac                                               20

<210> SEQ ID NO 60
<211> LENGTH: 20
<212> TYPE: DNA
<213> ORGANISM: Murine

<400> SEQUENCE: 60
tctcaggaac accatcgtct                                               20
```